United States Patent
Kudithipudi et al.

(10) Patent No.: US 12,270,037 B2
(45) Date of Patent: Apr. 8, 2025

(54) COMPOSITIONS AND METHODS FOR PRODUCING TOBACCO PLANTS AND PRODUCTS HAVING ALTERED ALKALOID LEVELS WITH DESIRABLE LEAF QUALITY VIA MANIPULATING LEAF QUALITY GENES

(71) Applicant: ALTRIA CLIENT SERVICES LLC, Richmond, VA (US)

(72) Inventors: Chengalrayan Kudithipudi, Richmond, VA (US); Rajanikanth Govindarajulu, Richmond, VA (US); Nazmul Bhuiyan, Richmond, VA (US); Raja Payyavula, Richmond, VA (US); Yanxin Shen, Richmond, VA (US); Dongmei Xu, Richmond, VA (US)

(73) Assignee: Altria Client Services LLC, Richmond, VA (US)

( * ) Notice: Subject to any disclaimer, the term of this patent is extended or adjusted under 35 U.S.C. 154(b) by 0 days.

(21) Appl. No.: 17/766,786

(22) PCT Filed: Oct. 9, 2020

(86) PCT No.: PCT/US2020/055046
§ 371 (c)(1),
(2) Date: Apr. 6, 2022

(87) PCT Pub. No.: WO2021/072241
PCT Pub. Date: Apr. 15, 2021

(65) Prior Publication Data
US 2024/0067977 A1    Feb. 29, 2024

Related U.S. Application Data

(60) Provisional application No. 62/913,308, filed on Oct. 10, 2019.

(51) Int. Cl.
*C12N 15/82* (2006.01)
*C07K 14/415* (2006.01)
*C12N 15/113* (2010.01)

(52) U.S. Cl.
CPC ........ *C12N 15/8243* (2013.01); *C07K 14/415* (2013.01); *C12N 15/1137* (2013.01); *C12N 15/8242* (2013.01)

(58) Field of Classification Search
None
See application file for complete search history.

(56) References Cited

U.S. PATENT DOCUMENTS

| | | |
|---|---|---|
| 4,516,590 A | 5/1985 | Teng |
| 4,528,993 A | 7/1985 | Sensabaugh, Jr. et al. |
| 4,660,577 A | 4/1987 | Sensabaugh, Jr. et al. |
| 4,732,856 A | 3/1988 | Federoff |
| 4,762,785 A | 8/1988 | Comai |
| 4,848,373 A | 7/1989 | Lenkey |
| 4,945,050 A | 7/1990 | Sanford et al. |
| 4,987,907 A | 1/1991 | Townend |
| 5,004,863 A | 4/1991 | Umbeck |
| 5,013,658 A | 5/1991 | Dooner et al. |
| 5,104,310 A | 4/1992 | Saltin |
| 5,141,131 A | 8/1992 | Miller et al. |
| 5,149,645 A | 9/1992 | Hoekema et al. |
| 5,159,135 A | 10/1992 | Umbeck |
| 5,177,010 A | 1/1993 | Goldman et al. |
| 5,231,019 A | 7/1993 | Paszkowski et al. |
| 5,316,931 A | 5/1994 | Donson et al. |
| 5,372,149 A | 12/1994 | Roth et al. |
| 5,463,174 A | 10/1995 | Moloney et al. |
| 5,464,763 A | 11/1995 | Schilperoort et al. |
| 5,469,976 A | 11/1995 | Burchell et al. |
| 5,491,081 A | 2/1996 | Webb et al. |
| 5,563,055 A | 10/1996 | Townsend et al. |
| 5,589,367 A | 12/1996 | Donson et al. |
| 5,659,026 A | 8/1997 | Baszczynski et al. |
| 5,689,035 A | 11/1997 | Webb |
| 5,789,156 A | 8/1998 | Bujard et al. |
| 5,814,618 A | 9/1998 | Bujard |
| 5,866,785 A | 2/1999 | Donson et al. |
| 5,879,918 A | 3/1999 | Tomes et al. |
| 5,886,244 A | 3/1999 | Tomes et al. |

(Continued)

FOREIGN PATENT DOCUMENTS

| | | |
|---|---|---|
| CN | 106 318 895 A | 1/2017 |
| CN | 109 337 914 A | 2/2019 |

(Continued)

OTHER PUBLICATIONS

Beinecke, et al. The Plant Journal 96.2 (2018): 329-342 (Year: 2018).*
Kano-Murakami, Yuriko, et al. "A rice homeotic gene, OSH1, causes unusual phenotypes in transgenic tobacco." FEBS letters 334.3 (1993): 365-368. (Year: 1993).*
Keskin, Ozlem, et al. "A new, structurally nonredundant, diverse data set of protein-protein interfaces and its implications." Protein Science 13.4 (2004): 1043-1055. (Year: 2004).*
Guo, Haiwei H., Juno Choe, and Lawrence A. Loeb. "Protein tolerance to random amino acid change." Proceedings of the National Academy of Sciences 101.25 (2004): 9205-9210. (Year: 2004).*
Thornton, Janet M., et al. "From structure to function: approaches and limitations." nature structural biology 7.11 (2000): 991-994. (Year: 2000).*

(Continued)

*Primary Examiner* — Charles Logsdon
*Assistant Examiner* — Kelsey L McWilliams
(74) *Attorney, Agent, or Firm* — Arnold & Porter Kaye Scholer LLP

(57) ABSTRACT

The present disclosure provides composition and methods for improving leaf quality of low-alkaloid tobacco plants. Also provided are the identification and genetic engineering of target genes (Leaf Quality Genes) for producing tobacco plants with altered total alkaloid and nicotine levels and commercially acceptable leaf grade, their development via breeding or transgenic approaches, and production of tobacco products from these tobacco plants.

14 Claims, 13 Drawing Sheets

Specification includes a Sequence Listing.

(56) References Cited

U.S. PATENT DOCUMENTS

| | | | |
|---|---|---|---|
| 5,889,190 | A | 3/1999 | Donson et al. |
| 5,889,191 | A | 3/1999 | Turpen |
| 5,932,782 | A | 8/1999 | Bidney |
| 5,981,840 | A | 11/1999 | Zhao et al. |
| 6,072,050 | A | 6/2000 | Bowen et al. |
| 8,124,851 | B2 | 2/2012 | Dewey et al. |
| 8,319,011 | B2 | 11/2012 | Xu et al. |
| 9,187,759 | B2 | 11/2015 | Dewey et al. |
| 9,228,194 | B2 | 1/2016 | Dewey et al. |
| 9,228,195 | B2 | 1/2016 | Dewey et al. |
| 9,247,706 | B2 | 2/2016 | Dewey et al. |
| 10,647,989 | B2 | 5/2020 | Kudithipudi et al. |
| 2004/0118422 | A1 | 6/2004 | Lundin et al. |
| 2005/0178398 | A1 | 8/2005 | Breslin et al. |
| 2006/0191548 | A1 | 8/2006 | Strickland et al. |
| 2007/0240728 | A1 | 10/2007 | Hashimoto et al. |
| 2008/0120737 | A1 | 5/2008 | Hashimoto et al. |
| 2015/0173319 | A1 | 2/2015 | Frederick et al. |
| 2017/0233756 | A1 | 8/2017 | Begemann et al. |
| 2018/0119163 | A1 | 5/2018 | Kudithipudi et al. |
| 2019/0271000 | A1 | 9/2019 | Fernando et al. |

FOREIGN PATENT DOCUMENTS

| | | |
|---|---|---|
| WO | WO 2004/041006 A1 | 5/2004 |
| WO | WO 2011/027315 A1 | 3/2011 |
| WO | WO 2018/067985 A1 | 4/2018 |
| WO | WO 2018/237107 A1 | 12/2018 |
| WO | WO 2019/140297 A1 | 7/2019 |

OTHER PUBLICATIONS

GenBank Accession XM_016582276.1 "Predicted: Nicotiana tabacum probable WRKY transcription factor 43 (LOC107763775), mRNA" dated May 3, 2016 https://www.ncbi.nlm.nih.gov/nucleotide/XM_016582276.1?report=genbank&log$=nuclalign&blast_rank=1&RID=6CX8BD63013 (Year: 2016).*

Beinecke et al., "The FT/FD-dependent initiation of flowering under long-day conditions n the day-neutral species Nicotiana tabacum originates from the facultative short-day ancestor Nicotiana tomentosiformis," The Plant Journal 96(2), pp. 329-342 (2018).

Database EMBL Accession No. KY306459 (2018).

Database NCBI Accession No. XM_106624437 (2016).

Hibi et al., "Gene Expresion in Tobacco Low-Nicotine Mutants," The Plant Cell 6(5), pp. 723-735 (1994).

Chapters 4B and 4C of Tobacco, Production, Chemistry and Technology, Davis & Nielsen, eds., Blackwell Publishing, pp. 70-103, (1999) (Oxford, UK).

Christensen et al., "Sequence analysis and transcriptional regulation by heat shock of polyubiquitin transcripts from maize," Plant Molecular Biology, 12, pp. 619-632 (Jun. 1989) (electronic publication), available online: https://doi.org/10.1007/BF00044153.

"CORESTA Recommended Method No. 7: Determination of Nicotine in the Mainstream Smoke of Cigarettes by Gas Chromatographic Analysis," pp. 1-5, (1987) (updated Aug. 1991) Paris, France.

Database EMBL Accession No. KY306458, "Nicotiana tabacum FD1 (FD1) mRNA, complete cds," created Sep. 11, 2018, 2 pages.

Database EMBL Accession No. KY306459, "Nicotiana tabacum FD2-like (FD2) mRNA, complete sequence," created Sep. 11, 2018, 2 pages.

Database NCBI Accession No. XM_016624437, "Predicted: Nicotiana tabacum protein FD-like (LOC107801153), mRNA," published May 3, 2016, 2 pages.

Hildering et al., "Chimeric structure of tomato plants after seed treatment with EMS and X-rays." The Use of Induced Mutations in Plant Breeding (Supplement to Radiation Botany), vol. 5, Pergamon Press Ltd., pp. 317-320, with cover page (1965) (London, UK).

Miller "Memorandum: Proposed Burley Tobacco Grade Index," Legacy Tobacco Document Library, the University of Tennessee Agricultural Experiment Station (Bates Document #523267826-523267833) (Jul. 1988) (Knoxville, USA).

Search Report issued in Chinese Patent Application No. 202080085804X, dated Nov. 29, 2023, 4 pages with machine translation.

Bowman et al., "Revised North Carolina grade index for flue-cured tobacco," Tobacco Science, 32: 39-40(1988).

Centers for Disease Control and Prevention's "Protocol for Analysis of Nicotine, Total Moisture and pH in Smokeless Tobacco Products," Federal Register vol. 64, No. 55 Mar. 23, 1999.

Cermak et al., "Efficient design and assembly of custom TALEN and other TAL effector-based constructs for DNA targeting," Nucleic Acids Research, 39(12): e82 (2011).

Chen et al., "Arabidopsis WRKY45 Interacts with the DELLA Protein RGL1 to Positively Regulate Age-Triggered Leaf Senescence," Molecular Plant, 10(9): 1174-1189 (2017).

Christensen et al., "Maize polyubiquitin genes: structure, thermal perturbation of expression and transcript splicing, and promoter activity following transfer to protoplasts by electroporation," Plant Molecular Biology, 12: 619-632 (1989).

Christensen et al., "Maize polyubiquitin genes: structure, thermal perturbation of expression and transcript splicing, and promoter activity following transfer to protoplasts by electroporation," Plant Molecular Biology, 18: 675-689 (1992).

Christou et al., "Stable Transformation of Soybean Callus by DNA-coated Gold Particles," Plant Physiology, 87: 671-674 (1988).

Collins et al., "Determination of nicotine alkaloids in tobacco using the Autoanalyzer," Tobacco Science, 13: 79-81 (1969).

CORESTA Method No. 62, "Determination of Nicotine in Tobacco and Tobacco Products by Gas Chromatographic Analysis," published Feb. 2005, updated Apr. 2020.

Crossway et al., "Micromanipulation Techniques in Plant Biotechnology," Biotechniques, 4(4): 320-334 (1986).

Davis, "A combined automated procedure for the determination of reducing sugars and nicotine alkaloids in tobacco products using a new reducing sugar method," Tobacco Science, 20: 139-144 (1976).

De Wet et al., "Exogenous gene transfer in maize (Zea mays) using DNA-treated pollen," in The Experimental Manipulation of Ovule Tissues, Chapman ed., Longman, New York, pp. 197-209 (1985).

Dewey et al., "Molecular genetics of alkaloid biosynthesis in Nicotiana tabacum," Phytochemistry, 94 10-27 (2013).

D'Halluin et al., "Transgenic maize plants by tissue electroporation," The Plant Cell, 4(12): 1495-1505 (1992).

Doyle et al., "TAL Effector-Nucleotide Targeter (TALE-NT) 2.0: tools for TAL effector design and target prediction," Nucleic Acids Research, 40(W1): W117-W122 (2012).

Estruch et al., "Transgenic plants: An emerging approach to pest control," Nature Biotechnology, 15: 137 (1997).

Fedoroff et al., "Cloning of the bronze locus in maize by a simple and generalizable procedure using the transposable controlling element Activator (Ac)," Proceedings of the National Academy of Sciences of the USA, 81(12): 3825-3829 (1984).

Finer et al., "Transformation of Soybean via particle bombardment of Embryogenic Suspension Culture Tissue," In Vitro Cellular & Developmental Biology—Plant, 27: 175-182 (1991).

Gaj et al., "ZFN, TALEN, and CRISPR/Cas-based methods for genome engineering," Trends in Biotechnology, 31(7): 397-405 (2013).

Gatz et al., "Regulation of a modified CaMV 35S promoter by the Tn10-encoded Tet repressor in transgenic tobacco," Molecular and General Genetics MGG, 227: 229-237 (1991).

Hibi et al., "Putrescine N-Methyltransferase in Cultured Roots of Hyoscyamus albus 1: n-Butylamine as a Potent Inhibitor of the Transferase both in Vitro and in Vivo," Plant Physiology, 100(2): 826-835 (1992).

Hoekema et al., "A binary plant vector strategy based on separation of vir- and T-region of the Agrobacterium tumefaciens Ti-plasmid," Nature, 303(12): 179-180 (1983).

Horsch et al., "A Simple and General Method for Transferring Genes into Plants," Science, 227(4691): 1229-1231 (1985).

International Convention for the Protection of New Varieties of Plants (Dec. 2, 1961, as revised at Geneva on Nov. 10, 1972, on Oct. 23, 1978, and on Mar. 19, 1991.

(56) References Cited

OTHER PUBLICATIONS

Kaeppler et al., "Silicon carbide fiber-mediated DNA delivery into plant cells," *Plant Cell Reports*, 9: 415-418 (1990).
Kaeppler et al., "Silicon carbide fiber-mediated stable transformation of plant cells," *Theoretical and Applied Genetics*, 84: 560-566 (1992).
Kajikawa et al., "Genomic Insights into the Evolution of the Nicotine Biosynthesis Pathway in Tobacco," *Plant Physiology*, 174(2): 999-1011 (2017).
Last et al., "pEmu: an improved promoter for gene expression in cereal cells," *Theoretical andApplied Genetics*, 81: 581-588 (1991).
Mayo et al., "Genetic transformation of tobacco NT1 cells with Agrobacterium tumefaciens,", *Nature Protocol*, 1(3): 1105-1111 (2006).
McCabe et al., "Stable Transformation of Soybean (*Glycine max*) by Particle Acceleration," *Bio/Technology*, 6: 923-926 (1988).
McCallum et al., "Targeted screening for induced mutations," *Nature Biotechnology*, 18: 455-457 (2000).
McNellis et al., "Glucocorticoid-inducible expression of a bacterial a virulence gene in transgenic *Arabidopsis* induces hypersensitive cell death," *The Plant Journal*, 14(2): 247-257 (1998).
Miller et al., "A grade index for type 22 and 23 fire-cured tobacco," *Tobacco International*, 192(22): 55-57 (1990).
Morita et al., "Vacuolar transport of nicotine is mediated by a multidrug and toxic compound extrusion (MATE) transporter in *Nicotiana tabacum*," *Proceeding of the National Academy of Science of the USA*, 106(7): 2447-2452 (2009).
Odell et al., "Identification of DNA sequences required for activity of the cauliflower mosaic virus 358 promoter," *Nature*, 313: 810-812 (1985).
Official Standard Grades for Burley Tobacco (U.S. Type 31 and Foreign Type 93), effective Nov. 5, 1990 (55 F.R. 40645).
Official Standard Grades for Flue-Cured Tobacco (U.S. Types 11, 12, 13, 14 and Foreign Type 92), effective Mar. 27, 1989 (54 F.R. 7925).
Official Standard Grades for Georgia and Florida Shade-Grown Cigar-Wrapper Tobacco (U.S. Type 62), Effective Apr. 1971.
Official Standard Grades for Ohio Cigar-Leaf Tobacco (U.S. Types 42, 43, and 44), effective Dec. 8, 1963 (28 F.R. 11719 and 28 F.R. 11926).
Official Standard Grades for Pennsylvania Seedleaf Tobacco (U.S. Type 41), effective Jan. 8, 1965 (29 F.R. 16854).
Official Standard Grades for Wisconsin Cigar-Binder Tobacco (U.S. Types 54 and 55), effective Nov. 20, 1969 (34 F.R. 17061).
Paszkowski et al., "Direct gene transfer to plants," *The EMBO Journal*, 3: 2717-2722 (1984).
Porta et al., "Use of Viral replicons for the expression of genes in plants," *Molecular Biotechnology*, 5: 209-221 (1996).
Riggs et al., "Stable transformation of tobacco by electroporation: evidence for plasmid concatenation," *Proceeding of the National Academy of Science of the USA*, 83(15): 5602-5606 (1986).
Schena et al., "A steroid-inducible gene expression system for plant cells," *Proceeding ofhe National Academy of Science of the USA*, 88(23): 10421-10425 (1991).
Shillito et al., "[19] Direct gene transfer to protoplasts of dicotyledonous and monocotyledonous plants by a number of methods, including electroporation," *Methods in Enzymology*, 153: 313-336 (1987).
Shoji et al., "Clustered Transcription Factor Genes Regulate Nicotine Biosynthesis in Tobacco," *The Plant Cell*, 22(10): 3390-3409 (2010).
Singh et al., "Cytological characterization of transgenic soybean," *Theoretical and Applied Genetics*, 96: 319-324 (1998).
Tomes et al., "Direct DNA Transfer into Intact Plant Cells via Microprojectile Bombardment," in *Plant Cell, Tissue, and Organ Culture Fundamental Methods*, Garnborg and Phillips ed., Springer-Verlag, Berlin (1995).
Tso, "Chapter 1: Seed to Smoke," in *Tobacco, Production, Chemistry and Technology*, Davis and Nielsen, ed., Blackwell Publishing, Oxford (1999).
Velten et al., "Isolation of a dual plant promoter fragment from the Ti plasmid of Agrobacterium tumefaciens," *The EMBO Journal*, 3: 2723-2730 (1984).
Verkerk, "Chimerism of the tomato plant after seed irradiation with fast neutrons," *Netherland Journal of Agricultural Science*, 19(4): 197-203 (1971).
Weising et al., "Foreign Genes in Plants: Transfer, Structure, Expression, and Application," *Annual Review of Genetics*, 22: 421-477 (1988).
Wernsman et al., "Chapter Seventeen: Tobacco" in *Principles Cultivar Development: Crop Species*, Fehr ed., MacMillan Publishing Go., Inc., New York (1987).
Boutros et al., "Genome-wide RNAi analysis of growth and Viability in *Drosophila* cells," *Science*, 303:832-835 (Feb. 2004).
Caldwell et al., "A structured mutant population for forward and reverse genetics in Barley (*Hordeum vulgare* L.)," *Plant Journal*, 40:143-150 (Aug. 2004).
Corral-Corral et al., "Systematic Identification of Machine-Learning Models Aimed to Classify Critical Residues for Protein Function from Protein Structure," *Molecules*, 22(10):1673, 17 pages (Oct. 2017).
Dietzl et al., "A genome-wide transgenic RNAi library for conditional gene inactivation in *Drosophila*," *Nature*, 448:151-156 (Jul. 2007).
Goehring et al., "Screening and large-scale expression of membrane proteins in mammalian cells for structural studies," *Nat. Protoc.*, 9:2574-2585 (Oct. 2014).
Greene et al., "Spectrum of chemically induced mutations from a large-scale reverse-genetic screen in *Arabidopsis*," *Genetics*, 164:731-740 (Jun. 2003).
Kelley et al., "The Phyre2 web portal for protein modeling, prediction and analysis," *Nature Protocols*, 10(6):845-858 (May 2015).
Kumar et al., "Predicting the effects of coding non-synonymous variants on protein function using the SIFT algorithm," *Nature Protocols*, 4(8):1073-1082 (Jun. 2009).
Lee et al., "A systematic RNAi screen identifies a critical role for mitochondria in *C. elegans* longevity," *Nature Genetics*, 33:40-48 (Jan. 2003).
Rushton et al., "WRKY transcription factors," *Trends in Plant Science*, 15(5):247-258,13 pages (Mar. 2010).
Schwarz et al., "MutationTaster2: mutation prediction for the deep-sequencing age," *Nature Methods*, 11(4):361-362 (Apr. 2014).
Sessions et al., "A High-Throughput *Arabidopsis* Reverse Genetics Screen," *Plant Cell*, 14:2985-2994 (Dec. 2002).
Sim et al., "SIFT web server: predicting effects of amino acid substitutions on proteins," *Nucleic Acids Research*, 40:W452-457 (Jun. 2012).

\* cited by examiner

COMPOSITIONS AND METHODS FOR PRODUCING TOBACCO PLANTS AND PRODUCTS HAVING ALTERED ALKALOID LEVELS WITH DESIRABLE LEAF QUALITY VIA MANIPULATING LEAF QUALITY GENES

SEQUENCE LISTING

This application is the U.S. National Stage of International Application No. PCT/US2020/055046, filed Oct. 9, 2020, which claims the benefit of U.S. Provisional Application No. 62/913,308, filed Oct. 10, 2019, both of which are incorporated by reference in their entirety herein. A sequence listing contained in the file named "P34750US01 SL.txt" which is 65,220 bytes (measured in MS-Windows®) and created on Apr. 5, 2022, is filed electronically herewith and incorporated by reference in its entirety herein.

FIELD

The present disclosure includes tobacco plants having altered total alkaloid and nicotine levels and commercially acceptable leaf grade, their development via breeding or transgenic approaches, and production of tobacco products from these tobacco plants.

BACKGROUND

Nicotine is the main alkaloid accumulating in tobacco leaves. Nicotine and other minor alkaloids (e.g., nornicotine, anabasine, and anatabine) are also precursors to tobacco-specific nitrosamines (TSNA). Demands exist for development of tobacco cultivars with lower levels of nicotine.

In commercial tobacco cultivars, nicotine represents 90-95% of the total alkaloid pool or 2-5% of total leaf dry weight. Nicotine is synthesized in the roots, and translocated through the xylem to aerial parts of the plant where it accumulates in the leaves and is exuded by trichomes in response to insect herbivory. Nicotine biosynthesis is influenced by genetic factors, plant development, biotic and abiotic stresses, phytohormonal signals and agronomic management practices such as topping and suckering. The genetic regulation of nicotine biosynthesis correlates to two independent loci, Nic1 and Nic2, which have a synergistic effect on nicotine levels, but the effect of Nic1 is ~2.4 times stronger than that of Nic2. Both loci also influence the expression of numerous other genes unrelated to the nicotine biosynthesis pathway. Transcriptional analysis has shown that the Nic2 locus is a gene cluster that encodes at least seven ethylene response transcription factors (ERFs).

Homozygous mutations of either one or both loci can be used to create near-isogenic Burley 21 lines with reduced alkaloid levels, i.e. a high-intermediate (HI) variety with the genotype nic2, a low-intermediate (LI) variety with the genotype nic1, and a low-alkaloid (LA) variety with the genotype nic1nic2. LA Burley 21 plants contain only ~5.7% of the total alkaloid levels found in the normal-alkaloid (NA) wild-type variety. In LA plants, the synergistic effect of the nic1 and nic2 mutations also causes an unfavorable leaf phenotype characterized by lower yields, delayed ripening and senescence, higher susceptibility to insect herbivory, and poor end-product quality after curing.

There is a need to identify genes that restore unfavorable leaf phenotypes in the LA variety of tobacco plants, and to develop tobacco plants and products that contain altered nicotine levels (e.g., reduced nicotine) while maintaining (if not making superior) tobacco leaf quality.

SUMMARY

In an aspect, the present disclosure provides a tobacco plant, or part thereof, comprising a mutation in a Leaf Quality Gene (LQG) or a transgene targeting a LQG gene.

In an aspect, the present disclosure provides a tobacco plant, or part thereof, comprising a genetic modification upregulating the expression or activity of a gene encoding a nucleic acid sequence having at least 90% identity or similarity to a nucleic acid sequence selected from the group consisting of SEQ ID NOs: 1-15. In another aspect, such tobacco plant is in a low-alkaloid variety background, where the tobacco plant produces a leaf, when cured, having a USDA grade index value higher than that of a comparable leaf of a control plant when grown and cured in similar conditions, where the control plant shares an essentially identical genetic background with the tobacco plant except the genetic modification.

In another aspect, the present disclosure provides a tobacco plant, or part thereof, comprising a recombinant nucleic acid construct comprising a heterologous promoter operably linked to a polynucleotide having at least 90% identity or similarity to a nucleic acid sequence selected from the group consisting of SEQ ID NOs: 1-15.

In an aspect, the present disclosure provides a tobacco plant, or part thereof, comprising a genetic modification upregulating the expression or activity of a gene encoding a polypeptide having at least 90% identity or similarity to an amino acid sequence selected from the group consisting of SEQ ID NOs: 18-32. In another aspect, such tobacco plant is in a low-alkaloid variety background, where the tobacco plant produces a leaf, when cured, having a USDA grade index value higher than that of a comparable leaf of a control plant when grown and cured in similar conditions, where the control plant shares an essentially identical genetic background with the tobacco plant except the genetic modification.

In another aspect, the present disclosure provides a tobacco plant, or part thereof, comprising a recombinant nucleic acid construct comprising a heterologous promoter operably linked to a polynucleotide encoding a polypeptide having at least 90% identity or similarity to an amino acid sequence selected from the group consisting of SEQ ID NOs: 18-32.

In an aspect, the present disclosure provides a tobacco plant, or part thereof, comprising a genetic modification downregulating the expression or activity of a gene encoding a nucleic acid sequence having at least 90% identity or similarity to a nucleic acid sequence selected from the group consisting of SEQ ID NOs: 16-17. In another aspect, such tobacco plant is in a low-alkaloid variety background, where the tobacco plant produces a leaf, when cured, having a USDA grade index value higher than that of a comparable leaf of a control plant when grown and cured in similar conditions, where the control plant shares an essentially identical genetic background with the tobacco plant except the genetic modification.

In another aspect, the present disclosure provides a tobacco plant, or part thereof, comprising a non-natural mutation in a polynucleotide having at least 90% identity or similarity to a nucleic acid sequence selected from the group consisting of SEQ ID NOs: 16-17.

In an aspect, the present disclosure provides a tobacco plant, or part thereof, comprising a recombinant nucleic acid construct comprising a heterologous promoter operably linked to a polynucleotide that encodes a non-coding RNA molecule, where the non-coding RNA molecule is capable of binding to an mRNA having at least 90% identity or similarity to a nucleic acid sequence selected from the group consisting of SEQ ID NOs: 16-17, where the non-coding RNA molecule suppresses the level or translation of the mRNA.

In another aspect, the present disclosure provides a tobacco plant, or part thereof, comprising a genetic modification downregulating the expression or activity of a gene encoding a polypeptide having at least 90% identity or similarity to an amino acid sequence selected from the group consisting of SEQ ID NOs: 33-34. In another aspect, such tobacco plant is in a low-alkaloid variety background, where the tobacco plant produces a leaf, when cured, having a USDA grade index value higher than that of a comparable leaf of a control plant when grown and cured in similar conditions, where the control plant shares an essentially identical genetic background with the tobacco plant except the genetic modification.

In an aspect, the present disclosure provides a tobacco plant, or part thereof, comprising a non-natural mutation in a polynucleotide having a nucleic acid sequence encoding a polypeptide having at least 90% identity or similarity to an amino acid sequence selected from the group consisting of SEQ ID NOs: 33-34.

In another aspect, the present disclosure provides a tobacco plant, or part thereof, comprising a recombinant nucleic acid construct comprising a heterologous promoter operably linked to a polynucleotide that encodes a non-coding RNA molecule, where the non-coding RNA molecule is capable of binding to an RNA encoding a polypeptide having at least 90% identity or similarity to an amino acid sequence selected from the group consisting of SEQ ID NOs: 33-34, where the non-coding RNA molecule suppresses the expression of the polypeptide.

In an aspect, the present disclosure provides a population of the tobacco plants described here, cured tobacco material from the tobacco plant described here, and reconstituted tobacco, a tobacco blend and a tobacco product made from the cured tobacco material In an aspect, the present disclosure provides a method for improving leaf quality in a reduced-alkaloid tobacco plant, the method comprising: (a) growing a reduced-alkaloid tobacco plant; (b) upregulating the expression or activity of a gene encoding (i) a nucleic acid sequence having at least 90% identity or similarity to a sequence selected from the group consisting of SEQ ID NOs: 1-15, or (ii) a polypeptide sequence having at least 90% identity or similarity to a sequence selected from the group consisting of SEQ ID NOs: 18-32; and (b) harvesting leaves or seeds from the tobacco plant.

In an aspect, the present disclosure provides a method for improving leaf quality in a reduced-alkaloid tobacco plant, the method comprising: (a) growing a reduced-alkaloid tobacco plant; (b) downregulating the expression or activity of a gene encoding (i) a nucleic acid sequence having at least 90% identity or similarity to a sequence selected from the group consisting of SEQ ID NOs: 16-17, or (ii) a polypeptide sequence having at least 90% identity or similarity to a sequence selected from the group consisting of SEQ ID NOs: 33-34; and (b) harvesting leaves or seeds from the tobacco plant.

BRIEF DESCRIPTION OF THE SEQUENCES

Figure 1A:
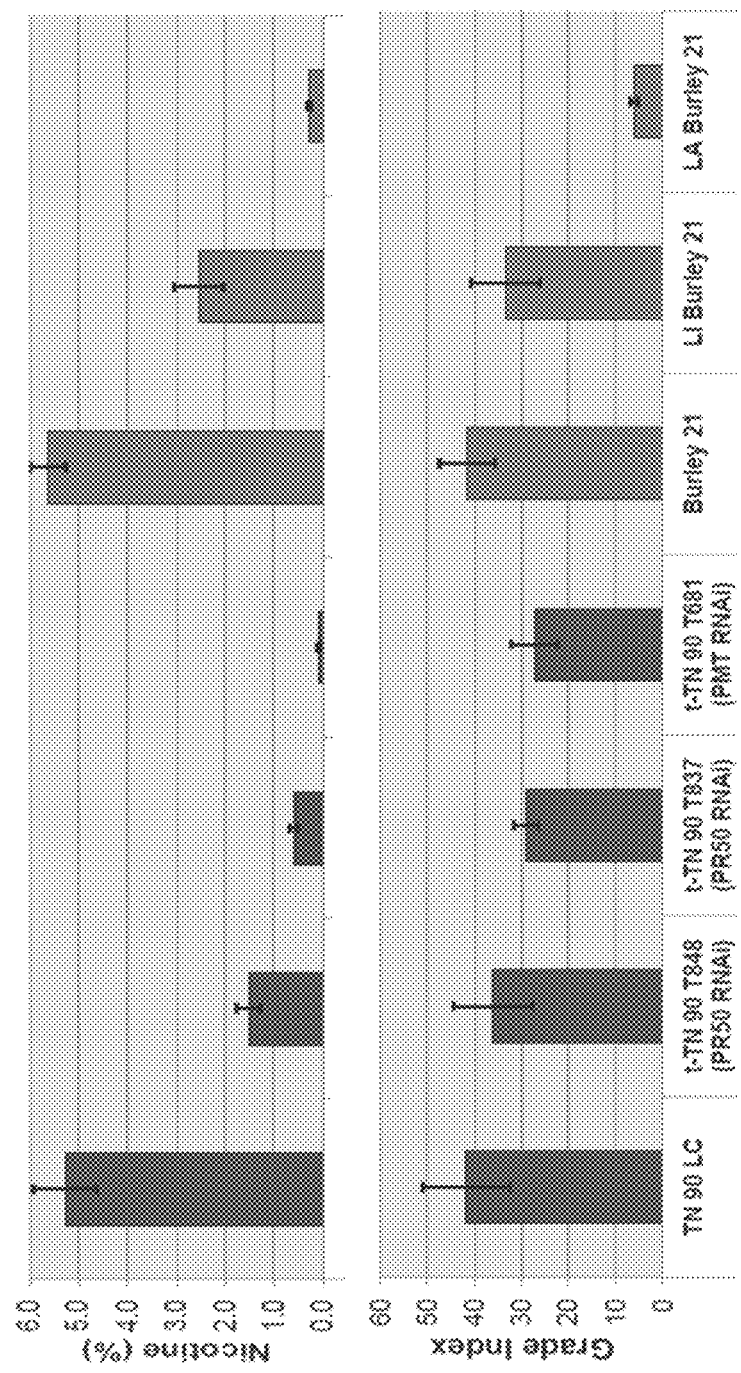
FIG. 1A depicts nicotine levels and leaf grade index of various burley varieties.

SEQ ID Nos: 1 to 17 set forth cDNA sequences of exemplary tobacco target genes for improving leaf quality.

SEQ ID Nos: 18 to 34 set forth amino acid sequences encoded by exemplary tobacco target genes for improving leaf quality.

Various sequences may include "N" in nucleotide sequences or "X" in amino acid sequences. "N" can be any nucleotide, e.g., A, T, G, C, or a deletion or insertion of one or more nucleotides. In some instant, a string of "N" are shown. The number of "N" does not necessarily correlate with the actual number of undetermined nucleotides at that position. The actual nucleotide sequences can be longer or shorter than the shown segment of "N". Similarly, "X" can be any amino acid residue or a deletion or insertion of one or more amino acids. Again, the number of "X" does not necessarily correlate with the actual number of undetermined amino acids at that position. The actual amino acid sequences can be longer or shorter than the shown segment of "X". Notwithstanding the use of A, T, G, C (compared to A, U, G, C) in describing any SEQ ID in the sequence listing, that SEQ ID can also refer to a RNA sequence, depending on the context in which the SEQ ID is mentioned.

DETAILED DESCRIPTION

Unless defined otherwise, technical and scientific terms used herein have the same meaning as commonly understood by one of ordinary skill in the art. One skilled in the art will recognize many methods can be used in the practice of the present disclosure. Indeed, the present disclosure is in no way limited to the methods and materials described. Where a term is provided in the singular, the inventors also contemplate aspects of the disclosure described by the plural of that term, and vice versa. Where there are discrepancies in terms and definitions used in references that are incorporated by reference, the terms used in this application shall have the definitions given herein. Other technical terms used have their ordinary meaning in the art in which they are used, as exemplified by various art-specific dictionaries, for example, "The American Heritage® Science Dictionary" (Editors of the American Heritage Dictionaries, 2011, Houghton Mifflin Harcourt, Boston and New York), the "McGraw-Hill Dictionary of Scientific and Technical Terms" (6th edition, 2002, McGraw-Hill, New York), or the "Oxford Dictionary of Biology" (6th edition, 2008, Oxford University Press, Oxford and New York).

Any references cited herein, including, e.g., all patents and publications are incorporated by reference in their entirety.

When a grouping of alternatives is presented, any and all combinations of the members that make up that grouping of alternatives is specifically envisioned. For example, if an item is selected from a group consisting of A, B, C, and D, the inventors specifically envision each alternative individually (e.g., A alone, B alone, etc.), as well as combinations such as A, B, and D; A and C; B and C; etc. The term "and/or" when used in a list of two or more items means any one of the listed items by itself or in combination with any one or more of the other listed items. For example, the expression "A and/or B" is intended to mean either or both of A and B—i.e., A alone, B alone, or A and B in combination. The expression "A, B and/or C" is intended to mean A alone, B alone, C alone, A and B in combination, A and C in combination, B and C in combination, or A, B, and C in combination.

When a range of numbers is provided herein, the range is understood to inclusive of the edges of the range as well as any number between the defined edges of the range. For example, "between 1 and 10" includes any number between 1 and 10, as well as the number 1 and the number 10.

As used herein, the singular form "a," "an," and "the" include plural references unless the context clearly dictates otherwise. For example, the term "a compound" or "at least one compound" may include a plurality of compounds, including mixtures thereof.

The term "about" is used herein to mean approximately, roughly, around, or in the region of. When the term "about" is used in conjunction with a numerical range, it modifies that range by extending the boundaries above and below the numerical values set forth, and is understood to mean plus or minus 10%. For example, "about 100" would include from 90 to 110.

To avoid any doubt, used herein, terms or phrases such as "about", "at least", "at least about", "at most", "less than", "greater than", "within" or alike, when followed by a series of list of numbers of percentages, such terms or phrases are deemed to modify each and every number of percentage in the series or list, regardless whether the adverb, preposition, or other modifier phrase is reproduced prior to each and every member.

As used herein, a "Leaf Quality Gene" (LQG) refers to a gene playing a role in tobacco leaf quality, in particular having a role in modulating leaf quality in a low-alkaloid variety. Exemplary LQGs can be found in Tables 9 and 10.

As used herein, a "low alkaloid variety" (also referred to as "LA variety") of tobacco refers to tobacco variety comprising one or more genetic modifications reducing the total alkaloids (measured via dry weight) to a level less than 25% of the total alkaloid level in a control tobacco variety of a substantially similar genetic background except for the one or more genetic modifications. As a non-limiting example, KY171 can serve as a control for a low-alkaloid variety LA KY171. Without being limiting, low-alkaloid tobacco varieties include LA Burley 21, LAFC53, LN B&W, and LN KY171. Similarly, a "low nicotine variety" (also referred to as "LN variety") of tobacco refers to tobacco variety comprising one or more genetic modifications reducing nicotine (measured via dry weight) to a level less than 25% of the nicotine level in a control tobacco variety of a substantially similar genetic background except for the one or more genetic modifications.

As used herein, a "genetic modification" refers to a change in the genetic makeup of a plant or plant genome. A genetic modification can be introduced by methods including, but not limited to, mutagenesis, genome editing, genetic transformation, or a combination thereof.

As used herein, a "LQG genetic modification" refers to a genetic modification relates to a LQG gene, including either a mutation (e.g., a non-natural mutation) in a LQG gene (e.g., as in a "LQG mutant") or a transgene targeting a LQG gene (e.g., as in a "LQG transgene"). As used here, "targeting" can be either directly upregulating or directly downregulating the expression or activity of a gene. As used here, "directly", in the context of a transgene impacting the expression or activity of a gene, refers to the impact being exerted over the gene via a physical contact or chemical interaction between the gene (e.g., a promoter region) or a product encoded therein (e.g., a mRNA molecule) and a product encoded by the transgene (e.g., a small non-coding RNA molecule or a protein).

As used herein, a "mutation" refers to an inheritable genetic modification introduced into a gene to alter the expression or activity of a product encoded by a reference sequence of the gene. Such a modification can be in any sequence region of a gene, for example, in a promoter, 5' UTR, exon, intron, 3' UTR, or terminator region. In an aspect, a mutation reduces, inhibits, or eliminates the expression or activity of a gene product. In another aspect, a mutation increases, elevates, strengthens, or augments the expression or activity of a gene product. In an aspect, mutations are not natural polymorphisms that exist in a particular tobacco variety or cultivar. It will be appreciated that, when identifying a mutation, the reference sequence should be from the same tobacco variety or background. For example, if a modified tobacco plant comprising a mutation is from the variety TN90, then the corresponding reference sequence should be the endogenous TN90 sequence, not a homologous sequence from a different tobacco variety (e.g., K326). In an aspect, a mutation is a "non-natural" or "non-naturally occurring" mutation. As used herein, a "non-natural" or "non-naturally occurring" mutation refers to a mutation that is not, and does not correspond to, a spontaneous mutation generated without human intervention. Non-limiting examples of human intervention include mutagenesis (e.g., chemical mutagenesis, ionizing radiation mutagenesis) and targeted genetic modifications (e.g., CRISPR-based methods, TALEN-based methods, zinc finger-based methods). Non-natural mutations and non-naturally occurring mutations do not include spontaneous mutations that arise naturally (e.g., via aberrant DNA replication in a germ line of a plant.

As used herein, a tobacco plant can be from any plant from the *Nicotiana* genus including, but not limited to *Nicotiana tabacum, Nicotiana amplexicaulis* PI 271989; *Nicotiana benthamiana* PI 555478; *Nicotiana bigelovii* PI 555485; *Nicotiana debneyi; Nicotiana excelsior* PI 224063;

*Nicotiana glutinosa* PI 555507; *Nicotiana goodspeedii* PI 241012; *Nicotiana gossei* PI 230953; *Nicotiana hesperis* PI 271991; *Nicotiana knightiana* PI 555527; *Nicotiana maritima* PI 555535; *Nicotiana megalosiphon* PI 555536; *Nicotiana nudicaulis* PI 555540; *Nicotiana paniculata* PI 555545; *Nicotiana plumbaginifolia* PI 555548; *Nicotiana repanda* PI 555552; *Nicotiana rustica*; *Nicotiana suaveolens* PI 230960; *Nicotiana sylvestris* PI 555569; *Nicotiana tomentosa* PI 266379; *Nicotiana tomentosiformis*; and *Nicotiana trigonophylla* PI 555572. In an aspect, a tobacco plant described here is a *Nicotiana tabacum* plant.

In an aspect, the present disclosure provides a tobacco plant, or part thereof, comprising a genetic modification upregulating or downregulating the expression or activity of a LQG gene. As used herein, the upregulation or downregulation of a gene by a genetic modification is determined by comparing a plant having the genetic modification with a corresponding control plant not having the genetic modification.

LQG Upregulation

In an aspect, the present disclosure provides a tobacco plant, or part thereof, comprising a genetic modification upregulating the expression or activity of a gene encoding a nucleic acid sequence having at least 70%, at least 80%, at least 90%, at least 95%, at least 97%, at least 99%, or 100% identity or similarity to a nucleic acid sequence selected from the group consisting of SEQ ID NOs: 1-15. In another aspect, the present disclosure provides a tobacco plant, or part thereof, comprising a recombinant nucleic acid construct comprising a heterologous promoter operably linked to a polynucleotide having at least 70%, at least 80%, at least 90%, at least 95%, at least 97%, at least 99%, or 100% identity or similarity to a nucleic acid sequence selected from the group consisting of SEQ ID NOs: 1-15. In another aspect, a tobacco plant described here is in a low-alkaloid variety background, where the tobacco plant produces a leaf, when cured, having a USDA grade index value higher than that of a comparable leaf of a control low-alkaloid plant when grown and cured in similar conditions, where the control low-alkaloid plant shares an essentially identical genetic background with the tobacco plant except the genetic modification. In an aspect, a higher USDA grade index value is at least 200%, 150%, 100%, 90%, 80%, 70%, 60%, 50%, 40%, 30%, 20%, 17.5%, 15%, 12.5%, 10%, 7.5%, or 5% higher than the USDA grade index value of a comparable leaf from a control plant.

In an aspect, the present disclosure provides a tobacco plant, or part thereof, comprising a genetic modification upregulating the expression or activity of a gene encoding a polypeptide having at least 70%, at least 80%, at least 90%, at least 95%, at least 97%, at least 99%, or 100% identity or similarity to an amino acid sequence selected from the group consisting of SEQ ID NOs: 18-32. In another aspect, the present disclosure provides a tobacco plant, or part thereof, comprising a recombinant nucleic acid construct comprising a heterologous promoter operably linked to a polynucleotide encoding a polypeptide having at least 70%, at least 80%, at least 90%, at least 95%, at least 97%, at least 99%, or 100% identity or similarity to an amino acid sequence selected from the group consisting of SEQ ID NOs: 18-32. In another aspect, a tobacco plant described here is in a low-alkaloid variety background, where the tobacco plant produces a leaf, when cured, having a USDA grade index value higher than that of a comparable leaf of a control low-alkaloid plant when grown and cured in similar conditions, where the control low-alkaloid plant shares an essentially identical genetic background with the tobacco plant except the genetic modification. In an aspect, a higher USDA grade index value is at least 200%, 150%, 100%, 90%, 80%, 70%, 60%, 50%, 40%, 30%, 20%, 17.5%, 15%, 12.5%, 10%, 7.5%, or 5% higher than the USDA grade index value of a comparable leaf from a control plant.

LQG Downregulation

In an aspect, the present disclosure provides a tobacco plant, or part thereof, comprising a genetic modification downregulating the expression or activity of a gene encoding a nucleic acid sequence having at least 70%, at least 80%, at least 90%, at least 95%, at least 97%, at least 99%, or 100% identity or similarity to a nucleic acid sequence selected from the group consisting of SEQ ID NOs: 16-17. In another aspect, such tobacco plant is in a low-alkaloid variety background, where the tobacco plant produces a leaf, when cured, having a USDA grade index value higher than that of a comparable leaf of a control low-alkaloid plant when grown and cured in similar conditions, where the control low-alkaloid plant shares an essentially identical genetic background with the tobacco plant except the genetic modification. In an aspect, a higher USDA grade index value is at least 200%, 150%, 100%, 90%, 80%, 70%, 60%, 50%, 40%, 30%, 20%, 17.5%, 15%, 12.5%, 10%, 7.5%, or 5% higher than the USDA grade index value of a comparable leaf from a control plant.

In another aspect, the present disclosure provides a tobacco plant, or part thereof, comprising a non-natural mutation in a polynucleotide having at least 70%, at least 80%, at least 90%, at least 95%, at least 97%, at least 99%, or 100% identity or similarity to a nucleic acid sequence selected from the group consisting of SEQ ID NOs: 16-17.

In an aspect, the present disclosure provides a tobacco plant, or part thereof, comprising a recombinant nucleic acid construct comprising a heterologous promoter operably linked to a polynucleotide that encodes a non-coding RNA molecule, where the non-coding RNA molecule is capable of binding to an mRNA having at least 70%, at least 80%, at least 90%, at least 95%, at least 97%, at least 99%, or 100% identity or similarity to a nucleic acid sequence selected from the group consisting of SEQ ID NOs: 16-17, where the non-coding RNA molecule suppresses the level or translation of the mRNA.

In another aspect, the present disclosure provides a tobacco plant, or part thereof, comprising a genetic modification downregulating the expression or activity of a gene encoding a polypeptide having at least 70%, at least 80%, at least 90%, at least 95%, at least 97%, at least 99%, or 100% identity or similarity to an amino acid sequence selected from the group consisting of SEQ ID NOs: 33-34. In another aspect, such tobacco plant is in a low-alkaloid variety background, where the tobacco plant produces a leaf, when cured, having a USDA grade index value higher than that of a comparable leaf of a control low-alkaloid plant when grown and cured in similar conditions, where the control low-alkaloid plant shares an essentially identical genetic background with the tobacco plant except the genetic modification. In an aspect, a higher USDA grade index value is at least 200%, 150%, 100%, 90%, 80%, 70%, 60%, 50%, 40%, 30%, 20%, 17.5%, 15%, 12.5%, 10%, 7.5%, or 5% higher than the USDA grade index value of a comparable leaf from a control plant.

In an aspect, the present disclosure provides a tobacco plant, or part thereof, comprising a non-natural mutation in a polynucleotide having a nucleic acid sequence encoding a polypeptide having at least 70%, at least 80%, at least 90%, at least 95%, at least 97%, at least 99%, or 100% identity or similarity to an amino acid sequence selected from the group consisting of SEQ ID NOs: 33-34.

In another aspect, the present disclosure provides a tobacco plant, or part thereof, comprising a recombinant nucleic acid construct comprising a heterologous promoter operably linked to a polynucleotide that encodes a non-coding RNA molecule, where the non-coding RNA molecule is capable of binding to an RNA encoding a polypeptide having at least 70%, at least 80%, at least 90%, at least 95%, at least 97%, at least 99%, or 100% identity or similarity to an amino acid sequence selected from the group consisting of SEQ ID NOs: 33-34, where the non-coding RNA molecule suppresses the expression of the polypeptide.

Low-Alkaloid Tobacco Background

In one aspect, a tobacco plant comprising a LQG mutation or transgene can further comprise a mutation or a transgene conferring a reduced level of nicotine. In an aspect, a tobacco plant is from a low-alkaloid variety. In one aspect, tobacco plants of the present disclosure comprise a nic1 mutation, a nic2 mutation, or both. In an aspect, tobacco plants comprise nicotine at a level below 1%, below 2%, below 5%, below 8%, below 10%, below 12%, below 15%, below 20%, below 25%, below 30%, below 40%, below 50%, below 60%, below 70%, or below 80% of the nicotine level of a control plant when grown in similar growth conditions, where the control plant shares an essentially identical genetic background with the tobacco plant except a low-nicotine conferring mutation or transgene. In another aspect, tobacco plants comprise nicotine or total alkaloids at a level below 1%, below 2%, below 5%, below 8%, below 10%, below 12%, below 15%, below 20%, below 25%, below 30%, below 40%, below 50%, below 60%, below 70%, or below 80% of the nicotine or total alkaloids level of the control plant when grown in similar growth conditions. In another aspect, tobacco plants comprise a total alkaloid level selected from the group consisting of less than 3%, less than 2.75%, less than 2.5%, less than 2.25%, less than 2.0%, less than 1.75%, less than 1.5%, less than 1.25%, less than 1%, less than 0.9%, less than 0.8%, less than 0.7%, less than 0.6%, less than 0.5%, less than 0.4%, less than 0.3%, less than 0.2%, less than 0.1%, and less than 0.05% of the nicotine level of a control plant when grown in similar growth conditions, where the control plant shares an essentially identical genetic background with the tobacco plant except a low-nicotine conferring mutation or transgene. In another aspect, tobacco plants comprise a nicotine or total alkaloid level selected from the group consisting of less than 3%, less than 2.75%, less than 2.5%, less than 2.25%, less than 2.0%, less than 1.75%, less than 1.5%, less than 1.25%, less than 1%, less than 0.9%, less than 0.8%, less than 0.7%, less than 0.6%, less than 0.5%, less than 0.4%, less than 0.3%, less than 0.2%, less than 0.1%, and less than 0.05% of the nicotine or total alkaloids level of the control plant when grown in similar growth conditions.

In an aspect, a tobacco plant comprising a LQG mutation or transgene further comprises a transgene or mutation directly suppressing the expression or activity of one or more, two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, twenty or more, or all twenty-one genes or loci encoding a protein selected from the group consisting of aspartate oxidase, agmatine deiminase (AIC), arginase, diamine oxidase, arginine decarboxylase (ADC), methylputrescine oxidase (MPO), NADH dehydrogenase, ornithine decarboxylase (ODC), phosphoribosylanthranilate isomerase (PRAI), putrescine N-methyltransferase (PMT), quinolate phosphoribosyl transferase (QPT), S-adenosyl-methionine synthetase (SAMS), A622, NBB1, BBL, MYC2, Nic1_ERF, Nic2_ERF, ethylene response factor (ERF) transcription factor, nicotine uptake permease (NUP), and MATE transporter. See Dewey and Xie, Molecular genetics of alkaloid biosynthesis in *Nicotiana tabacum*, Phytochemistry 94 (2013) 10-27.

In an aspect, a tobacco plant comprising a LQG mutation or transgene further comprises a mutation in an ERF gene of Nic2 locus (Nic2 ERF). In an aspect, a tobacco plant comprising a LQG mutation or transgene further comprises one or more mutations in one or more, two or more, three or more, four or more, five or more, six or more, seven or more, eight or more, nine or more, or all ten genes selected from the group consisting of ERF32, ERF34, ERF39, ERF189, ERF115, ERF221, ERF704, ERF179, ERF17, and ERF168. See Shoji et al., *Plant Cell*, (10):3390-409 (2010); and Kajikawa et al., *Plant physiol*. 2017, 174:999-1011. In one aspect, a tobacco plant further comprises one or more mutations in ERF189, ERF115, or both. In an aspect, a tobacco plant comprising a LQG mutation or transgene further comprises one or more transgenes targeting and suppressing a gene encoding one or more, two or more, three or more, four or more, five or more, six or more, seven or more, eight or more, nine or more, or all ten proteins selected from the group consisting of ERF32, ERF34, ERF39, ERF189, ERF115, ERF221, ERF704, ERF179, ERF77, and ERF168.

In an aspect, a tobacco plant comprising a LQG mutation or transgene further comprises a mutation in an ERF gene of Nic1 locus (Nic1 ERF) (or Nic1b locus as in PCT/US2019/013345 filed on Jan. 11, 2019, published as WO/2019/140297). See also WO/2018/237107. In an aspect, a tobacco comprising a LQG mutation or transgene further comprises one or more mutations in two or more, three or more, four or more, five or more, six or more, or seven or more genes selected from the group consisting of ERF101, ERF110, ERFnew, ERF199, ERF19, ERF130, ERF16, ERF29, ERF210, and ERF91L2. See WO/2019/140297 and Kajikawa et al., *Plant physiol*. 2017, 174:999-1011. In an aspect, a tobacco plant comprising a LQG mutation or transgene further comprises one or more mutations in one or more, two or more, three or more, four or more, five or more, or all six genes selected from the group consisting of ERFnew, ERF199, ERF19, ERF29, ERF210, and ERF91L2. In an aspect, a tobacco plant comprising a LQG mutation or transgene further comprises one or more transgenes targeting and suppressing a gene encoding one or more, two or more, three or more, four or more, five or more, six or more, or seven or more genes selected from the group consisting of ERF01, ERF110, ERFnew, ERF199, ERF19, ERF130, ERF16, ERF29, ERF210, and ERF91L2.

In an aspect, tobacco plants provided herein comprise a first genome modification comprising a mutation in a gene or locus encoding a protein selected from the group consisting of aspartate oxidase, agmatine deiminase (AIC), arginase, diamine oxidase, arginine decarboxylase (ADC), methylputrescine oxidase (MPO), NADH dehydrogenase, ornithine decarboxylase (ODC), phosphoribosylanthranilate isomerase (PRAI), putrescine N-methyltransferase (PMT), quinolate phosphoribosyl transferase (QPT), and S-adenosyl-methionine synthetase (SAMS), A622, NBB1, BBL, MYC2, Nic1_ERF, Nic2_ERF, ethylene response factor (ERF) transcription factor, nicotine uptake permease (NUP), and MATE transporter, and further comprises a second genetic modification targeting one or more LQG genes. In one aspect, tobacco plants provided herein comprise a first genome modification comprises a transgene targeting and suppressing a gene or locus encoding a protein selected from the group consisting of aspartate oxidase, agmatine deiminase (AIC), arginase, diamine oxidase, arginine decarboxylase (ADC), methylputrescine oxidase (MPO), NADH dehydrogenase, ornithine decarboxylase (ODC), phosphoribosylanthranilate isomerase (PRAI), putrescine N-methyltransferase (PMT), quinolate phosphoribosyl transferase (QPT), and S-adenosyl-methionine synthetase (SAMS), A622, NBB1, BBL, MYC2, Nic1, Nic2, ethylene response factor (ERF) transcription factor, nicotine uptake permease (NUP), and MATE transporter, and further comprises a second genetic modification targeting one or more LQG genes.

Leaf Quality/Grading

In an aspect, the present disclosure provides a tobacco plant, or part thereof, comprising a LQG genetic modification in a low-alkaloid variety background with commercially acceptable leaf quality. The present disclosure also provides LQG mutant or transgenic tobacco plants having altered nicotine levels without negative impacts over other tobacco traits, e.g., leaf grade index value. In an aspect, a low-nicotine or nicotine-free LQG mutant or transgenic tobacco variety provides cured tobacco of commercially acceptable grade.

Tobacco grades are evaluated based on factors including, but not limited to, the leaf stalk position, leaf size, leaf color, leaf uniformity and integrity, ripeness, texture, elasticity, sheen (related with the intensity and the depth of coloration of the leaf as well as the shine), hygroscopicity (the faculty of the tobacco leaves to absorb and to retain the ambient moisture), and green nuance or cast. Leaf grade can be determined, for example, using an Official Standard Grade published by the Agricultural Marketing Service of the US Department of Agriculture (7 U.S.C. § 511). See, e.g., Official Standard Grades for Burley Tobacco (U.S. Type 31 and Foreign Type 93), effective Nov. 5, 1990 (55 F.R. 40645); Official Standard Grades for Flue-Cured Tobacco (U.S. Types 11, 12, 13, 14 and Foreign Type 92), effective Mar. 27, 1989 (54 F.R. 7925); Official Standard Grades for Pennsylvania Seedleaf Tobacco (U.S. Type 41), effective Jan. 8, 1965 (29 F.R. 16854); Official Standard Grades for Ohio Cigar-Leaf Tobacco (U.S. Types 42, 43, and 44), effective Dec. 8, 1963 (28 F.R. 11719 and 28 F.R. 11926); Official Standard Grades for Wisconsin Cigar-Binder Tobacco (U.S. Types 54 and 55), effective Nov. 20, 1969 (34 F.R. 17061); Official Standard Grades for Wisconsin Cigar-Binder Tobacco (U.S. Types 54 and 55), effective Nov. 20, 1969 (34 F.R. 17061); Official Standard Grades for Georgia and Florida Shade-Grown Cigar-Wrapper Tobacco (U.S. Type 62), Effective April 1971. A USDA grade index value can be determined according to an industry accepted grade index. See, e.g., Bowman et al, Tobacco Science, 32:39-40 (1988); Legacy Tobacco Document Library (Bates Document #523267826-523267833, Jul. 1, 1988, Memorandum on the Proposed Burley Tobacco Grade Index); and Miller et al., 1990, *Tobacco Intern.*, 192:55-57 (all foregoing references are incorporated by inference in their entirety). Unless specified otherwise, a USDA grade index is a 0-100 numerical representation of federal grade received and is a weighted average of all stalk positions. A higher grade index indicates higher quality. Alternatively, leaf grade can be determined via hyper-spectral imaging. See e.g., WO 2011/027315 (published on Mar. 10, 2011, and incorporated by inference in its entirety).

In an aspect, LQG mutant or transgenic tobacco plants described here are capable of producing leaves, when cured, having a USDA grade index value selected from the group consisting of 55 or more, 60 or more, 65 or more, 70 or more, 75 or more, 80 or more, 85 or more, 90 or more, and 95 or more. In another aspect, tobacco plants are capable of producing leaves, when cured, having a USDA grade index value comparable to that of a control plant when grown and cured in similar conditions, where the control plant shares an essentially identical genetic background with the tobacco plant except a low-nicotine conferring mutation or transgene. In a further aspect, tobacco plants are capable of producing leaves, when cured, having a USDA grade index value of at least about 65%, at least about 70%, at least about 75%, at least about 80%, at least about 85%, at least about 90%, at least about 95%, or at least about 98% of the USDA grade index value of a control plant when grown in similar conditions, where the control plant shares an essentially identical genetic background with the tobacco plant except a low-nicotine conferring mutation or transgene. In a further aspect, tobacco plants are capable of producing leaves, when cured, having a USDA grade index value of between 65% and 130%, between 70% and 130%, between 75% and 130%, between 80% and 130%, between 85% and 130%, between 90% and 130%, between 95% and 130%, between 100% and 130%, between 105% and 130%, between 110% and 130%, between 115% and 130%, or between 120% and 130% of the USDA grade index value of the control plant. In a further aspect, tobacco plants are capable of producing leaves, when cured, having a USDA grade index value of between 70% and 125%, between 75% and 120%, between 80% and 115%, between 85% and 110%, or between 90% and 100% of the USDA grade index value of the control plant.

In another aspect, LQG mutant or transgenic tobacco plants described here are capable of producing leaves, when cured, having a USDA grade index value selected from the group consisting of 55 or more, 60 or more, 65 or more, 70 or more, 75 or more, 80 or more, 85 or more, 90 or more, and 95 or more. In another aspect, tobacco plants are capable of producing leaves, when cured, having a USDA grade index value selected from the group consisting of between 50 and 95, between 55 and 95, between 60 and 95, between 65 and 95, between 70 and 95, between 75 and 95, between 80 and 95, between 85 and 95, between 90 and 95, between 55 and 90, between 60 and 85, between 65 and 80, between 70 and 75, between 50 and 55, between 55 and 60, between 60 and 65, between 65 and 70, between 70 and 75, between 75 and 80, between 80 and 85, between 85 and 90, and between 90 and 95. In a further aspect, tobacco plants are capable of producing leaves, when cured, having a USDA grade index value of at least about 65%, at least about 70%, at least about 75%, at least about 80%, at least about 85%, at least about 90%, at least about 95%, or at least about 98% of the USDA grade index value of the control plant. In a further aspect, tobacco plants are capable of producing leaves, when cured, having a USDA grade index value of between 65% and 130%, between 70% and 130%, between 75% and 130%, between 80% and 130%, between 85% and 130%, between 90% and 130%, between 95% and 130%, between 100% and 130%, between 105% and 130%, between 110% and 130%, between 115% and 130%, or between 120% and 130% of the USDA grade index value of the control plant. In a further aspect, tobacco plants are capable of producing leaves, when cured, having a USDA grade index value of between 70% and 125%, between 75% and 120%, between 80% and 115%, between 85% and 110%, or between 90% and 100% of the USDA grade index value of the control plant.

In an aspect, the present disclosure further provides a LQG mutant or transgenic tobacco plant, or part thereof, comprising a nicotine or total alkaloid level selected from the group consisting of less than 3%, less than 2.75%, less than 2.5%, less than 2.25%, less than 2.0%, less than 1.75%, less than 1.5%, less than 1.25%, less than 1%, less than 0.9%, less than 0.8%, less than 0.7%, less than 0.6%, less than 0.5%, less than 0.4%, less than 0.3%, less than 0.2%, less than 0.1%, and less than 0.05%, where the tobacco plants are capable of producing leaves, when cured, having a USDA grade index value of 50 or more 55 or more, 60 or more, 65 or more, 70 or more, 75 or more, 80 or more, 85 or more, 90 or more, and 95 or more. In another aspect, such LQG mutant or transgenic tobacco plants comprise a nicotine level of less than 2.0% and are capable of producing leaves, when cured, having a USDA grade index value of 70 or more. In a further aspect, such LQG mutant or transgenic tobacco plants comprise a nicotine level of less than 1.0% and are capable of producing leaves, when cured, having a USDA grade index value of 70 or more.

In an aspect, the present disclosure also provides a LQG mutant or transgenic tobacco plant, or part thereof, comprising a non-transgenic mutation, where the non-transgenic mutation reduces the nicotine or total alkaloid level of the tobacco plant to below 1%, below 2%, below 5%, below 8%, below 10%, below 12%, below 15%, below 20%, below 25%, below 30%, below 40%, below 50%, below 60%, below 70%, or below 80% of the nicotine level of a control plant when grown in similar growth conditions, where the tobacco plant is capable of producing leaves, when cured, having a USDA grade index value comparable to the USDA grade index value of the control plant, and where the control plant shares an essentially identical genetic background with the tobacco plant except the non-transgenic mutation.

LA Leaf Phenotype Improvement

LA Burley 21 (also referenced as LA BU21) is a low total alkaloid tobacco line produced by incorporation of a low alkaloid gene(s) from a Cuban cigar variety into Burley 21 through several backcrosses. It has approximately 0.2% total alkaloids (dry weight) compared to the about 3.5% (dry weight) of its parent, Burley 21. LA BU21 has a leaf grade well below commercially acceptable standards. LA BU21 also exhibits other unfavorable leaf phenotypes characterized by lower yields, delayed ripening and senescence, higher susceptibility to insect herbivory, and poor end-product quality after curing. LA BU21 leaves further exhibit traits such as higher polyamine content, higher chlorophyll content and more mesophyll cells per unit leaf area. See US2019/0271000 for more characterization of LA BU21 leaf phenotypes.

In an aspect, a LQG mutation or transgene described here is capable of improving one or more aspects of LA BU21 leaf quality. In an aspect, the present disclosure provides tobacco plants, or part thereof, comprising a low nicotine or low alkaloid-conferring mutation or transgene and capable of producing a leaf comprising a comparable level of one or more polyamines relative to a comparable leaf of a control plant not comprising the same mutation or transgene. In one aspect, a comparable level of one or more polyamines is within 20%, 17.5%, 15%, 12.5%, 10%, 7.5%, 5%, 2.5%, or 1% of the level in a comparable leaf of a control plant not comprising the same mutation or transgene. In an aspect, a comparable level of one or more polyamines is between 0.5% and 1%, between 1% and 2%, between 2% and 3%, between 3% and 4%, between 4% and 5%, between 5% and 6%, between 6% and 7%, between 7% and 8%, between 8% and 9%, between 9% and 10%, between 11% and 12%, between 12% and 13%, between 13% and 14%, between 14% and 15%, between 15% and 16%, between 16% and 17%, between 17% and 18%, between 18% and 19%, or between 19% and 20% of the level in a comparable leaf of a control plant not comprising the same mutation or transgene. In a further aspect, a comparable level of one or more polyamines is between 0.5% and 5%, between 5% and 10%, or between 10% and 20% of the level in a comparable leaf of a control plant not comprising the same mutation or transgene.

In an aspect, the present disclosure provides LQG mutant or transgenic tobacco plants, or part thereof, comprising a low nicotine or low alkaloid-conferring mutation or transgene and capable of producing a leaf comprising a comparable chlorophyll level relative to a comparable leaf of a control plant not comprising the same mutation or transgene. In one aspect, a comparable chlorophyll level is within 20%, 17.5%, 15%, 12.5%, 10%, 7.5%, 5%, 2.5%, or 1% of the level in a comparable leaf of a control plant not comprising the same mutation or transgene. In an aspect, a comparable chlorophyll level is between 0.5% and 1%, between 1% and 2%, between 2% and 3%, between 3% and 4%, between 4% and 5%, between 5% and 6%, between 6% and 7%, between 7% and 8%, between 8% and 9%, between 9% and 10%, between 11% and 12%, between 12% and 13%, between 13% and 14%, between 14% and 15%, between 15% and 16%, between 16% and 17%, between 17% and 18%, between 18% and 19%, or between 19% and 20% of the level in a comparable leaf of a control plant not comprising the same mutation or transgene. In a further aspect, a comparable chlorophyll level is between 0.5% and 5%, between 5% and 10%, or between 10% and 20% of the level in a comparable leaf of a control plant not comprising the same mutation or transgene.

In an aspect, the present disclosure provides LQG mutant or transgenic tobacco plants, or part thereof, comprising a low nicotine or low alkaloid-conferring mutation or transgene and capable of producing a leaf comprising a comparable number of mesophyll cell per unit of leaf area relative to a comparable leaf of a control plant not comprising the same mutation or transgene. In one aspect, a comparable number of mesophyll cell per unit of leaf area is within 20%, 17.5%, 15%, 12.5%, 10%, 7.5%, 5%, 2.5%, or 1% of the level in a comparable leaf of a control plant not comprising the same mutation or transgene. In an aspect, a comparable number of mesophyll cell per unit of leaf area is between 0.5% and 1%, between 1% and 2%, between 2% and 3%, between 3% and 4%, between 4% and 5%, between 5% and 6%, between 6% and 7%, between 7% and 8%, between 8% and 9%, between 9% and 10%, between 11% and 12%, between 12% and 13%, between 13% and 14%, between 14% and 15%, between 15% and 16%, between 16% and 17%, between 17% and 18%, between 18% and 19%, or between 19% and 20% of the level in a comparable leaf of a control plant not comprising the same mutation or transgene. In a further aspect, a comparable number of mesophyll cell per unit of leaf area is between 0.5% and 5%, between 5% and 10%, or between 10% and 20% of the level in a comparable leaf of a control plant not comprising the same mutation or transgene.

In an aspect, the present disclosure provides LQG mutant or transgenic tobacco plants, or part thereof, comprising a low nicotine or low alkaloid-conferring mutation or transgene and capable of producing a leaf comprising a comparable epidermal cell size relative to a comparable leaf of a control plant not comprising the same mutation or transgene. In one aspect, a comparable epidermal cell size is within 20%, 17.5%, 15%, 12.5%, 10%, 7.5%, 5%, 2.5%, or 1% of the level in a comparable leaf of a control plant not comprising the same mutation or transgene. In an aspect, a comparable epidermal cell size is between 0.5% and 1%, between 1% and 2%, between 2% and 3%, between 3% and 4%, between 4% and 5%, between 5% and 6%, between 6% and 7%, between 7% and 8%, between 8% and 9%, between 9% and 10%, between 11% and 12%, between 12% and 13%, between 13% and 14%, between 14% and 15%, between 15% and 16%, between 16% and 17%, between 17% and 18%, between 18% and 19%, or between 19% and 20% of the level in a comparable leaf of a control plant not comprising the same mutation or transgene. In a further aspect, a comparable epidermal cell size is between 0.5% and 5%, between 5% and 10%, or between 10% and 20% of the level in a comparable leaf of a control plant not comprising the same mutation or transgene.

In an aspect, the present disclosure provides LQG mutant or transgenic tobacco plants, or part thereof, comprising a low nicotine or low alkaloid-conferring mutation or transgene and capable of producing a leaf comprising a comparable leaf yield relative to a comparable leaf of a control plant not comprising the same mutation or transgene. In one aspect, a comparable leaf yield is within 20%, 17.5%, 15%, 12.5%, 10%, 7.5%, 5%, 2.5%, or 1% of the level in a comparable leaf of a control plant not comprising the same mutation or transgene. In an aspect, a comparable leaf yield is between 0.5% and 1%, between 1% and 2%, between 2% and 3%, between 3% and 4%, between 4% and 5%, between 5% and 6%, between 6% and 7%, between 7% and 8%, between 8% and 9%, between 9% and 10%, between 11% and 12%, between 12% and 13%, between 13% and 14%, between 14% and 15%, between 15% and 16%, between 16% and 17%, between 17% and 18%, between 18% and 19%, or between 19% and 20% of the level in a comparable leaf of a control plant not comprising the same mutation or transgene. In a further aspect, a comparable leaf yield is between 0.5% and 5%, between 5% and 10%, or between 10% and 20% of the level in a comparable leaf of a control plant not comprising the same mutation or transgene.

In an aspect, the present disclosure provides LQG mutant or transgenic tobacco plants, or part thereof, comprising a low nicotine or low alkaloid-conferring mutation or transgene and exhibiting a comparable insect herbivory susceptibility relative to a comparable leaf of a control plant not comprising the same mutation or transgene. In one aspect, a comparable insect herbivory susceptibility is within 20%, 17.5%, 15%, 12.5%, 10%, 7.5%, 5%, 2.5%, or 1% of the level in a comparable leaf of a control plant not comprising the same mutation or transgene. In an aspect, a comparable insect herbivory susceptibility is between 0.5% and 1%, between 1% and 2%, between 2% and 3%, between 3% and 4%, between 4% and 5%, between 5% and 6%, between 6% and 7%, between 7% and 8%, between 8% and 9%, between 9% and 10%, between 11% and 12%, between 12% and 13%, between 13% and 14%, between 14% and 15%, between 15% and 16%, between 16% and 17%, between 17% and 18%, between 18% and 19%, or between 19% and 20% of the level in a comparable leaf of a control plant not comprising the same mutation or transgene. In a further aspect, a comparable insect herbivory susceptibility is between 0.5% and 5%, between 5% and 10%, or between 10% and 20% of the level in a comparable leaf of a control plant not comprising the same mutation or transgene.

Insect herbivory susceptibility level can be assayed by methods known in the art, for example, in an insect feeding assay. In short, a quarter inch layer of 0.7% agar in water is added to a 100 mm Petri dish and allowed to solidify. Leaf discs are cut from the petri dish lid, placed in the plates and pushed gently into the agar. Leaf discs are taken from plants at the 4-5 leaf stage. Discs were taken from lamina only to exclude major midribs. A single disc is taken from each of the four largest leaves of the plant generating 4 replicates per plant. Four plants are sampled for a total of 16 biological replicates test line. A single budworm (e.g., *Heliothis* sp., *Helicoverpa* sp.) at the second instar stage is added to the leaf and allowed to feed for 48 hours at ambient temperature. After 48 hours the budworm larvae are weighed and final larval weights are recorded.

In an aspect, a tobacco plant, or part thereof, comprises relative to a control tobacco plant: a first genome modification providing a lower level of nicotine or total alkaloid, and a second genome modification providing a comparable level of one or more traits selected from the group consisting of total leaf polyamine level, total root polyamine level, total leaf chlorophyll level, mesophyll cell number per leaf area unit, and leaf epidermal cell size; and where the control plant does not have both the first and the second genome modifications. In one aspect, a tobacco plant, or part thereof, comprises relative to a control tobacco plant: a first genome modification providing a lower level of nicotine or total alkaloid, and a second genome modification providing a comparable level of total leaf polyamine level, where the control plant does not have both the first and the second genome modifications. In an aspect, a tobacco plant, or part thereof, comprises relative to a control tobacco plant: a first genome modification providing a lower level of nicotine or total alkaloid, and a second genome modification providing a comparable level of total root polyamine level, where the control plant does not have both the first and the second genome modifications. In one aspect, a tobacco plant, or part thereof, comprises relative to a control tobacco plant: a first genome modification providing a lower level of nicotine or total alkaloid, and a second genome modification providing a comparable level of total leaf chlorophyll level, where the control plant does not have both the first and the second genome modifications. In an aspect, a tobacco plant, or part thereof, comprises relative to a control tobacco plant: a first genome modification providing a lower level of nicotine or total alkaloid, and a second genome modification providing a comparable level of mesophyll cell number per leaf area unit, where the control plant does not have both the first and the second genome modifications. In one aspect, a tobacco plant, or part thereof, comprises relative to a control tobacco plant: a first genome modification providing a lower level of nicotine or total alkaloid, and a second genome modification providing a comparable level of leaf epidermal cell size, where the control plant does not have both the first and the second genome modifications. In an aspect, a second genome modification is in or targeting a LQG gene.

In an aspect, a first genome modification, a second genome modification, or both comprise a transgene, a mutation, or both. In one aspect, a genome modification, a second genome modification, or both comprise a transgene. In an aspect, a first genome modification, a second genome modification, or both comprise a mutation. In one aspect, a first genome modification, a second genome modification, or both are not transgene-based. In an aspect, a first genome modification, a second genome modification, or both are not mutation-based.

In an aspect, tobacco plants provided herein comprise a reduced amount of total conjugated polyamines in leaves relative to the control tobacco plant. In one aspect, tobacco plants provided herein comprise a reduced amount of total conjugated polyamines in roots relative to the control tobacco plant. Used here, conjugated polyamines include, but are not limited to, soluble conjugated polyamines such as phenolamides containing a backbone consisting of a free polyamine (e.g., putrescine, spermine, and/or spermidine) conjugated with one or more phenylpropanoids such as ferulic, caffeic and courmaric acids. Conjugated polyamines also include, but are not limited to, insoluble conjugated polyamines incorporated into structural polymers such as lignin. In an aspect, tobacco plants provided herein comprise a reduced amount of total free polyamines (e.g., putrescine, spermine, and spermidine) in leaves relative to the control tobacco plant. In one aspect, tobacco plants provided herein comprise a reduced amount of total conjugated polyamines in roots relative to the control tobacco plant. In an aspect, tobacco plants provided herein comprise a reduced amount of total conjugated form of one or more polyamines selected from the group consisting of putrescine, spermidine and spermine in leaves relative to the control tobacco plant. In one aspect, tobacco plants provided herein comprise a reduced amount of total conjugated form of one or more polyamines selected from the group consisting of putrescine, spermidine and spermine in roots relative to the control tobacco plant. In an aspect, tobacco plants provided herein comprise a reduced amount of total free form of one or more polyamines selected from the group consisting of putrescine, spermidine and spermine in leaves relative to the control tobacco plant. In one aspect, tobacco plants provided herein comprise a reduced amount of total conjugated form of one or more polyamines selected from the group consisting of putrescine, spermidine and spermine in roots relative to the control tobacco plant.

In an aspect, a characteristic or a trait of a tobacco plant described here are measured at a time selected from the group consisting of immediately before flowering, at topping, 1 week-post-topping (WPT), 2 WPT, 3 WPT, 4 WPT, 5 WPT, 6 WPT, 7 WPT, 8 WPT, and at harvest. In one aspect, tobacco plants provided herein comprising a first and a second genome modification are capable of producing a leaf with a leaf grade comparable to that of a leaf from a control plant. In an aspect, tobacco plants provided herein comprising a first and a second genome modification have a total leaf yield comparable to a control plant.

Chemical Measurements

"Alkaloids" are complex, nitrogen-containing compounds that naturally occur in plants, and have pharmacological effects in humans and animals. "Nicotine" is the primary natural alkaloid in commercialized cigarette tobacco and accounts for about 90 percent of the alkaloid content in *Nicotiana tabacum*. Other major alkaloids in tobacco include cotinine, nornicotine, myosmine, nicotyrine, anabasine and anatabine. Minor tobacco alkaloids include nicotine-n-oxide, N-methyl anatabine, N-methyl anabasine, pseudooxynicotine, 2,3 dipyridyl and others.

In an aspect, a LQG mutant or transgenic tobacco plant provided herein comprises a genetic modification providing a lower level of one or more alkaloids selected from the group consisting of cotinine, nornicotine, myosmine, nicotyrine, anabasine and anatabine, compared to a control tobacco plant without the genetic modification, when grown in similar growth conditions. In an aspect, a lower alkaloid or nicotine level refers to an alkaloid or nicotine level of below 1%, below 2%, below 5%, below 8%, below 10%, below 12%, below 15%, below 20%, below 25%, below 30%, below 40%, below 50%, below 60%, below 70%, or below 80% of the alkaloid or nicotine level of a control tobacco plant. In another aspect, a lower alkaloid or nicotine level refers to an alkaloid or nicotine level of about between 0.5% and 1%, between 1% and 2%, between 2% and 3%, between 3% and 4%, between 4% and 5%, between 5% and 6%, between 6% and 7%, between 7% and 8%, between 8% and 9%, between 9% and 10%, between 11% and 12%, between 12% and 13%, between 13% and 14%, between 14% and 15%, between 15% and 16%, between 16% and 17%, between 17% and 18%, between 18% and 19%, between 19% and 20%, between 21% and 22%, between 22% and 23%, between 23% and 24%, between 24% and 25%, between 25% and 26%, between 26% and 27%, between 27% and 28%, between 28% and 29%, or between 29% and 30% of the alkaloid or nicotine level of a control tobacco plant. In a further aspect, a lower alkaloid or nicotine level refers to an alkaloid or nicotine level of about between 0.5% and 5%, between 5% and 10%, between 10% and 20%, between 20% and 30% of the alkaloid or nicotine level of a control tobacco plant.

In an aspect, a LQG mutant or transgenic tobacco plant provided herein comprises an average nicotine or total alkaloid level selected from the group consisting of about 0.01%, 0.02%, 0.05%, 0.75%, 0.1%, 0.15%, 0.2%, 0.3%, 0.35%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2%, 2.1%, 2.2%, 2.3%, 2.4%, 2.5%, 2.6%, 2.7%, 2.8%, 2.9%, 3%, 3.1%, 3.2%, 3.3% 3.4% 3.5% 3.6%, 3.7% 3.8%, 3.9%, 4%, 5%, 6%, 7%, 8%, and 9% on a dry weight basis. In another aspect, tobacco plants provided herein comprise an average nicotine or total alkaloid level selected from the group consisting of about between 0.01% and 0.02%, between 0.02% and 0.05%, between 0.05% and 0.75%, between 0.75% and 0.1%, between 0.1% and 0.15%, between 0.15% and 0.2%, between 0.2% and 0.3%, between 0.3% and 0.35%, between 0.35% and 0.4%, between 0.4% and 0.5%, between 0.5% and 0.6%, between 0.6% and 0.7%, between 0.7% and 0.8%, between 0.8% and 0.9%, between 0.9% and 1%, between 1% and 1.1%, between 1.1% and 1.2%, between 1.2% and 1.3%, between 1.3% and 1.4%, between 1.4% and 1.5%, between 1.5% and 1.6%, between 1.6% and 1.7%, between 1.7% and 1.8%, between 1.8% and 1.9%, between 1.9% and 2%, between 2% and 2.1%, between 2.1% and 2.2%, between 2.2% and 2.3%, between 2.3% and 2.4%, between 2.4% and 2.5%, between 2.5% and 2.6%, between 2.6% and 2.7%, between 2.7% and 2.8%, between 2.8% and 2.9%, between 2.9% and 3%, between 3% and 3.1%, between 3.1% and 3.2%, between 3.2% and 3.3%, between 3.3% and 3.4%, between 3.4% and 3.5%, and between 3.5% and 3.6% on a dry weight basis. In a further aspect, tobacco plants provided herein comprise an average nicotine or total alkaloid level selected from the group consisting of about between 0.01% and 0.1%, between 0.02% and 0.2%, between 0.03% and 0.3%, between 0.04% and 0.4%, between 0.05% and 0.5%, between 0.75% and 1%, between 0.1% and 1.5%, between 0.15% and 2%, between 0.2% and 3%, and between 0.3% and 3.5% on a dry weight basis.

Unless specified otherwise, measurements of alkaloid, polyamine, or nicotine levels (or another leaf chemistry or property characterization) or leaf grade index values mentioned herein for a tobacco plant, variety, cultivar, or line refer to average measurements, including, for example, an average of multiple leaves of a single plant or an average measurement from a population of tobacco plants from a single variety, cultivar, or line. Unless specified otherwise, the nicotine, alkaloid, or polyamine level (or another leaf chemistry or property characterization) of a tobacco plant described here is measured 2 weeks after topping in a pooled leaf sample collected from leaf number 3, 4, and 5 after topping. In another aspect, the nicotine, alkaloid, or polyamine level (or another leaf chemistry or property characterization) of a tobacco plant is measured after topping in a leaf having the highest level of nicotine, alkaloid, or polyamine (or another leaf chemistry or property characterization). In an aspect, the nicotine, alkaloid, or polyamine level of a tobacco plant is measured after topping in leaf number 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30. In another aspect, the nicotine, alkaloid, or polyamine level (or another leaf chemistry or property characterization) of a tobacco plant is measured after topping in a pool of two or more leaves with consecutive leaf numbers selected from the group consisting of leaf number 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30. In another aspect, the nicotine, alkaloid, or polyamine level (or another leaf chemistry or property characterization) of a tobacco plant is measured after topping in a leaf with a leaf number selected from the group consisting of between 1 and 5, between 6 and 10, between 11 and 15, between 16 and 20, between 21 and 25, and between 26 and 30. In another aspect, the nicotine, alkaloid, or polyamine level (or another leaf chemistry or property characterization) of a tobacco plant is measured after topping in a pool of two or more leaves with leaf numbers selected from the group consisting of between 1 and 5, between 6 and 10, between 11 and 15, between 16 and 20, between 21 and 25, and between 26 and 30. In another aspect, the nicotine, alkaloid, or polyamine level (or another leaf chemistry or property characterization) of a tobacco plant is measured after topping in a pool of three or more leaves with leaf numbers selected from the group consisting of between 1 and 5, between 6 and 10, between 11 and 15, between 16 and 20, between 21 and 25, and between 26 and 30.

Alkaloid levels can be assayed by methods known in the art, for example by quantification based on gas-liquid chromatography, high performance liquid chromatography, radio-immunoassays, and enzyme-linked immunosorbent assays. For example, nicotinic alkaloid levels can be measured by a GC-FID method based on CORESTA Recommended Method No. 7, 1987 and ISO Standards (ISO TC 126N 394 E. See also Hibi et al., *Plant Physiology* 100: 826-35 (1992) for a method using gas-liquid chromatography equipped with a capillary column and an FID detector. Unless specified otherwise, all alkaloid levels described here are measured using a method in accordance with CORESTA Method No 62, *Determination of Nicotine in Tobacco and Tobacco Products by Gas Chromatographic Analysis*, February 2005, and those defined in the Centers for Disease Control and Prevention's *Protocol for Analysis of Nicotine, Total Moisture and pH in Smokeless Tobacco Products*, as published in the Federal Register Vol. 64, No. 55 Mar. 23, 1999 (and as amended in Vol. 74, No. 4, Jan. 7, 2009).

Alternatively, tobacco total alkaloids can be measured using a segmented-flow colorimetric method developed for analysis of tobacco samples as adapted by Skalar Instrument Co (West Chester, PA) and described by Collins et al., *Tobacco Science* 13:79-81 (1969). In short, samples of tobacco are dried, ground, and extracted prior to analysis of total alkaloids and reducing sugars. The method then employs an acetic acid/methanol/water extraction and charcoal for decolorization. Determination of total alkaloids was based on the reaction of cyanogen chloride with nicotine alkaloids in the presence of an aromatic amine to form a colored complex which is measured at 460 nm. Unless specified otherwise, total alkaloid levels or nicotine levels shown herein are on a dry weight basis (e.g., percent total alkaloid or percent nicotine).

As used herein, leaf numbering is based on the leaf position on a tobacco stalk with leaf number 1 being the oldest leaf (at the base) after topping and the highest leaf number assigned to the youngest leaf (at the tip).

A population of tobacco plants or a collection of tobacco leaves for determining an average measurement (e.g., alkaloid or nicotine level or leaf grading) can be of any size, for example, 5, 10, 15, 20, 25, 30, 35, 40, or 50. Industry-accepted standard protocols are followed for determining average measurements or grade index values.

As used herein, "topping" refers to the removal of the stalk apex, including the SAM, flowers, and up to several adjacent leaves, when a tobacco plant is near vegetative maturity and around the start of reproductive growth. Typically, tobacco plants are topped in the button stage (soon after the flower begins to appear). For example, greenhouse or field-grown tobacco plants can be topped when 50% of the plants have at least one open flower. Topping a tobacco plant results in the loss of apical dominance and also induce increased alkaloid production.

Typically, the nicotine, alkaloid, or polyamine level (or another leaf chemistry or property characterization) of a tobacco plant is measured about 2 weeks after topping. Other time points can also be used. In an aspect, the nicotine, alkaloid, or polyamine level (or another leaf chemistry or property characterization) of a tobacco plant is measured about 1, 2, 3, 4, or 5 weeks after topping. In another aspect, the nicotine, alkaloid, or polyamine level (or another leaf chemistry or property characterization) of a tobacco plant is measured about 3, 5, 7, 10, 12, 14, 17, 19, or 21 days after topping.

As used herein, "similar growth conditions" refer to similar environmental conditions and/or agronomic practices for growing and making meaningful comparisons between two or more plant genotypes so that neither environmental conditions nor agronomic practices would contribute to or explain any difference observed between the two or more plant genotypes. Environmental conditions include, for example, light, temperature, water (humidity), and nutrition (e.g., nitrogen and phosphorus). Agronomic practices include, for example, seeding, clipping, undercutting, transplanting, topping, and suckering. See Chapters 4B and 4C of Tobacco, Production, Chemistry and Technology, Davis & Nielsen, eds., Blackwell Publishing, Oxford (1999), pp 70-103.

As used herein, "comparable leaves" refer to leaves having similar size, shape, age, and/or stalk position.

Aroma/Flavor

In an aspect, LQG mutant or transgenic tobacco plants provided herein comprise a similar level of one or more tobacco aroma compounds selected from the group consisting of 3-methylvaleric acid, valeric acid, isovaleric acid, a labdenoid, a cembrenoid, a sugar ester, and a reducing sugar, compared to control tobacco plants when grown in similar growth conditions.

As used herein, tobacco aroma compounds are compounds associated with the flavor and aroma of tobacco smoke. These compounds include, but are not limited to, 3-methylvaleric acid, valeric acid, isovaleric acid, cembrenoid and labdenoid diterpenes, and sugar esters. Concentrations of tobacco aroma compounds can be measured by any known metabolite profiling methods in the art including, without limitation, gas chromatography mass spectrometry (GC-MS), Nuclear Magnetic Resonance Spectroscopy, liquid chromatography-linked mass spectrometry. See The Handbook of Plant Metabolomics, edited by Weckwerth and Kahl, (Wiley-Blackwell) (May 28, 2013).

As used herein, "reducing sugar(s)" are any sugar (monosaccharide or polysaccharide) that has a free or potentially free aldehyde or ketone group. Glucose and fructose act as nicotine buffers in cigarette smoke by reducing smoke pH and effectively reducing the amount of "free" unprotonated nicotine. Reducing sugars balances smoke flavor, for example, by modifying the sensory impact of nicotine and other tobacco alkaloids. An inverse relationship between sugar content and alkaloid content has been reported across tobacco varieties, within the same variety, and within the same plant line caused by planting conditions. Reducing sugar levels can be measured using a segmented-flow colorimetric method developed for analysis of tobacco samples as adapted by Skalar Instrument Co (West Chester, PA) and described by Davis, *Tobacco Science* 20:139-144 (1976). For example, a sample is dialyzed against a sodium carbonate solution. Copper neocuproin is added to the sample and the solution is heated. The copper neocuproin chelate is reduced in the presence of sugars resulting in a colored complex which is measured at 460 nm.

TSNA

In still another aspect, a tobacco plant provided further comprises one or more mutations in one or more loci encoding a nicotine demethylase (e.g., CYP82E4, CYP82E5, CYP82E10) that confer reduced amounts of nornicotine (See U.S. Pat. Nos. 8,319,011; 8,124,851; 9,187,759; 9,228,194; 9,228,195; 9,247,706) compared to control plant lacking one or more mutations in one or more loci encoding a nicotine demethylase. In an aspect, a modified tobacco plant described further comprises reduced nicotine demethylase activity compared to a control plant when grown and cured under comparable conditions. In a further aspect, a tobacco plant provided further comprises one or more mutations or transgenes providing an elevated level of one or more antioxidants (See U.S. patent application Ser. No. 15/727,523 and PCT Application No. PCT/US2017/055618). In another aspect, a tobacco plant provided further comprises one or more mutations or transgenes providing a reduced level of one or more tobacco-specific nitrosamines (TSNAs) (such as N'-nitrosonornicotine (NNN), 4-methyl-nitrosoamino-1-(3-pyridyl)-1-butanone (NNK), N'-nitrosoanatabine (NAT) N'-nitrosoanabasine (NAB)).

Mutation Types

In an aspect, the present disclosure provides a tobacco plant, or part thereof, comprising a non-natural mutation in a LQG gene (e.g., as in a "LQG mutant"). In an aspect, a non-natural mutation comprises one or more mutation types selected from the group consisting of a nonsense mutation, a missense mutation, a frameshift mutation, a splice-site mutation, and any combinations thereof. As used herein, a "nonsense mutation" refers to a mutation to a nucleic acid sequence that introduces a premature stop codon to an amino acid sequence by the nucleic acid sequence. As used herein, a "missense mutation" refers to a mutation to a nucleic acid sequence that causes a substitution within the amino acid sequence encoded by the nucleic acid sequence. As used herein, a "frameshift mutation" refers to an insertion or deletion to a nucleic acid sequence that shifts the frame for translating the nucleic acid sequence to an amino acid sequence. A "splice-site mutation" refers to a mutation in a nucleic acid sequence that causes an intron to be retained for protein translation, or, alternatively, for an exon to be excluded from protein translation. Splice-site mutations can cause nonsense, missense, or frameshift mutations.

Mutations in coding regions of genes (e.g., exonic mutations) can result in a truncated protein or polypeptide when a mutated messenger RNA (mRNA) is translated into a protein or polypeptide. In an aspect, this disclosure provides a mutation that results in the truncation of a protein or polypeptide. As used herein, a "truncated" protein or polypeptide comprises at least one fewer amino acid as compared to an endogenous control protein or polypeptide. For example, if endogenous Protein A comprises 100 amino acids, a truncated version of Protein A can comprise between 1 and 99 amino acids.

Without being limited by any scientific theory, one way to cause a protein or polypeptide truncation is by the introduction of a premature stop codon in an mRNA transcript of an endogenous gene. In an aspect, this disclosure provides a mutation that results in a premature stop codon in an mRNA transcript of an endogenous gene. As used herein, a "stop codon" refers to a nucleotide triplet within an mRNA transcript that signals a termination of protein translation. A "premature stop codon" refers to a stop codon positioned earlier (e.g., on the 5'-side) than the normal stop codon position in an endogenous mRNA transcript. Without being limiting, several stop codons are known in the art, including "UAG," "UAA," "UGA," "TAG," "TAA," and "TGA."

In an aspect, a mutation provided herein comprises a null mutation. As used herein, a "null mutation" refers to a mutation that confers a complete loss-of-function for a protein encoded by a gene comprising the mutation, or, alternatively, a mutation that confers a complete loss-of-function for a small RNA encoded by a genomic locus. A null mutation can cause lack of mRNA transcript production, a lack of small RNA transcript production, a lack of protein function, or a combination thereof.

A mutation provided herein can be positioned in any part of an endogenous gene. In an aspect, a mutation provided herein is positioned within an exon of an endogenous gene. In another aspect, a mutation provided herein is positioned within an intron of an endogenous gene. In a further aspect, a mutation provided herein is positioned within a 5'-untranslated region (UTR) of an endogenous gene. In still another aspect, a mutation provided herein is positioned within a 3'-UTR of an endogenous gene. In yet another aspect, a mutation provided herein is positioned within a promoter of an endogenous gene. In yet another aspect, a mutation provided herein is positioned within a terminator of an endogenous gene.

In an aspect, a mutation in an endogenous gene results in a reduced level of expression as compared to the endogenous gene lacking the mutation. In another aspect, a mutation in an endogenous gene results in an increased level of expression as compared to the endogenous gene lacking the mutation.

In an aspect, a non-natural mutation results in a reduced level of expression as compared to expression of the gene in a control tobacco plant. In an aspect, a non-natural mutation results in an increased level of expression as compared to expression of the gene in a control tobacco plant.

In a further aspect, a mutation in an endogenous gene results in a reduced level of activity by a protein or polypeptide encoded by the endogenous gene having the mutation as compared to a protein or polypeptide encoded by the endogenous gene lacking the mutation. In a further aspect, a mutation in an endogenous gene results in an increased level of activity by a protein or polypeptide encoded by the endogenous gene having the mutation as compared to a protein or polypeptide encoded by the endogenous gene lacking the mutation.

In an aspect, a non-natural mutation results in a reduced level of activity by a protein or polypeptide encoded by the polynucleotide comprising the non-natural mutation as compared to a protein or polypeptide encoded by the polynucleotide lacking the non-natural mutation. In another aspect, a non-natural mutation results in an increased level of activity by a protein or polypeptide encoded by the polynucleotide comprising the non-natural mutation as compared to a protein or polypeptide encoded by the polynucleotide lacking the non-natural mutation.

In an aspect, a mutation provided here provides a dominant mutant that activates the expression or elevates the activity of a gene of interest, e.g., one or more LQG genes.

Levels of gene expression are routinely investigated in the art. As non-limiting examples, gene expression can be measured using quantitative reverse transcriptase PCR (qRT-PCR), RNA sequencing, or Northern blots. In an aspect, gene expression is measured using qRT-PCR. In another aspect, gene expression is measured using a Northern blot. In another aspect, gene expression is measured using RNA sequencing.

LQG mutant tobacco plants can be made by any method known in the art including random or targeted mutagenesis approaches. Such mutagenesis methods include, without limitation, treatment of seeds with ethyl methylsulfate (EMS) (Hildering and Verkerk, In, The use of induced mutations in plant breeding. Pergamon press, pp 317-320, 1965) or UV-irradiation, X-rays, and fast neutron irradiation (see, for example, Verkerk, Neth. J Agric. Sci. 19:197-203, 1971; and Poehlman, Breeding Field Crops, Van Nostrand Reinhold, New York (3.sup.rd ed), 1987), transposon tagging (Fedoroff et al., 1984; U.S. Pat. Nos. 4,732,856 and 5,013,658), as well as T-DNA insertion methodologies (Hoekema et al., 1983; U.S. Pat. No. 5,149,645). EMS-induced mutagenesis consists of chemically inducing random point mutations over the length of the genome. Fast neutron mutagenesis consists of exposing seeds to neutron bombardment which causes large deletions through double stranded DNA breakage. Transposon tagging comprises inserting a transposon within an endogenous gene to reduce or eliminate expression of the gene. The types of mutations that may be present in a tobacco gene include, for example, point mutations, deletions, insertions, duplications, and inversions. Such mutations desirably are present in the coding region of a tobacco gene; however mutations in the promoter region, and intron, or an untranslated region of a tobacco gene may also be desirable.

In addition, a fast and automatable method for screening for chemically induced mutations, TILLING (Targeting Induced Local Lesions In Genomes), using denaturing HPLC or selective endonuclease digestion of selected PCR products is also applicable to the present disclosure. See, McCallum et al. (2000) *Nat. Biotechnol.* 18:455-457. Mutations that impact gene expression or that interfere with the function of genes can be determined using methods that are well known in the art. Insertional mutations in gene exons usually result in null-mutants. Mutations in conserved residues can be particularly effective in inhibiting the function of a protein. In an aspect, tobacco plants comprise a nonsense (e.g., stop codon) mutation in one or more NCG genes described in U.S. Provisional Application Nos. 62/616,959 and 62/625,878, both of which are incorporated by reference in their entirety.

In an aspect, the present disclosure also provides tobacco lines with altered nicotine levels while maintaining commercially acceptable leaf quality. In an aspect, such a line can be produced by introducing mutations into one or more LQG genes in a nic1 and/or nic2 background via precise genome engineering technologies, for example, Transcription activator-like effector nucleases (TALENs), meganuclease, zinc finger nuclease, and a clustered regularly-interspaced short palindromic repeats (CRISPR)/Cas9 system, a CRISPR/Cpf1 system, a CRISPR/Csm1 system, and a combination thereof (see, for example, U.S. Patent Application publication 2017/0233756). See, e.g., Gaj et al., *Trends in Biotechnology*, 31(7):397-405 (2013).

The screening and selection of mutagenized tobacco plants can be through any methodologies known to those having ordinary skill in the art. Examples of screening and selection methodologies include, but are not limited to, Southern analysis, PCR amplification for detection of a polynucleotide, Northern blots, RNase protection, primer-extension, RT-PCR amplification for detecting RNA transcripts, Sanger sequencing, Next Generation sequencing technologies (e.g., Illumina, PacBio, Ion Torrent, 454), enzymatic assays for detecting enzyme or ribozyme activity of polypeptides and polynucleotides, and protein gel electrophoresis, Western blots, immunoprecipitation, and enzyme-linked immunoassays to detect polypeptides. Other techniques such as in situ hybridization, enzyme staining, and immunostaining also can be used to detect the presence or expression of polypeptides and/or polynucleotides. Methods for performing all of the referenced techniques are known.

In an aspect, a tobacco plant or plant genome provided herein is mutated or edited by a genome editing technique, e.g., by a nuclease selected from the group consisting of a meganuclease, a zinc-finger nuclease (ZFN), a transcription activator-like effector nuclease (TALEN), a CRISPR/Cas9 nuclease, a CRISPR/Cpf1 nuclease, or a CRISPR/Csm1 nuclease.

As used herein, "editing" or "genome editing" refers to targeted mutagenesis of at least 1, at least 2, at least 3, at least 4, at least 5, at least 6, at least 7, at least 8, at least 9, or at least 10 nucleotides of an endogenous plant genome nucleic acid sequence, or removal or replacement of an endogenous plant genome nucleic acid sequence. In an aspect, an edited nucleic acid sequence provided has at least 99.9%, at least 99.5%, at least 99%, at least 98%, at least 97%, at least 96%, at least 95%, at least 94%, at least 93%, at least 92%, at least 91%, at least 90%, at least 85%, at least 80%, or at least 75% sequence identity with an endogenous nucleic acid sequence. In an aspect, an edited nucleic acid sequence provided has at least 99.9%, at least 99.5%, at least 99%, at least 98%, at least 97%, at least 96%, at least 95%, at least 94%, at least 93%, at least 92%, at least 91%, at least 90%, at least 85%, at least 80%, or at least 75% sequence identity with SEQ ID Nos: 1-17, and fragments thereof.

Meganucleases, ZFNs, TALENs, CRISPR/Cas9, CRISPR/Csm1 and CRISPR/Cpf1 induce a double-strand DNA break at a target site of a genomic sequence that is then repaired by the natural processes of homologous recombination (HR) or non-homologous end-joining (NHEJ). Sequence modifications then occur at the cleaved sites, which can include deletions or insertions that result in gene disruption in the case of NHEJ, or integration of donor nucleic acid sequences by HR. In an aspect, a method provided comprises editing a plant genome with a nuclease provided to mutate at least 1, at least 2, at least 3, at least 4, at least 5, at least 6, at least 7, at least 8, at least 9, at least 10, or more than 10 nucleotides in the plant genome via HR with a donor polynucleotide. In an aspect, a mutation provided is caused by genome editing using a nuclease. In another aspect, a mutation provided is caused by non-homologous end-joining or homologous recombination.

Meganucleases, which are commonly identified in microbes, are unique enzymes with high activity and long recognition sequences (>14 bp) resulting in site-specific digestion of target DNA. Engineered versions of naturally occurring meganucleases typically have extended DNA recognition sequences (for example, 14 to 40 bp). The engineering of meganucleases can be more challenging than that of ZFNs and TALENs because the DNA recognition and cleavage functions of meganucleases are intertwined in a single domain. Specialized methods of mutagenesis and high-throughput screening have been used to create novel meganuclease variants that recognize unique sequences and possess improved nuclease activity.

ZFNs are synthetic proteins consisting of an engineered zinc finger DNA-binding domain fused to the cleavage domain of the FokI restriction endonuclease. ZFNs can be designed to cleave almost any long stretch of double-stranded DNA for modification of the zinc finger DNA-binding domain. ZFNs form dimers from monomers composed of a non-specific DNA cleavage domain of FokI endonuclease fused to a zinc finger array engineered to bind a target DNA sequence.

The DNA-binding domain of a ZFN is typically composed of 3-4 zinc-finger arrays. The amino acids at positions −1, +2, +3, and +6 relative to the start of the zinc finger ∞-helix, which contribute to site-specific binding to the target DNA, can be changed and customized to fit specific target sequences. The other amino acids form the consensus backbone to generate ZFNs with different sequence specificities. Rules for selecting target sequences for ZFNs are known in the art.

The FokI nuclease domain requires dimerization to cleave DNA and therefore two ZFNs with their C-terminal regions are needed to bind opposite DNA strands of the cleavage site (separated by 5-7 bp). The ZFN monomer can cute the target site if the two-ZF-binding sites are palindromic. The term ZFN, as used herein, is broad and includes a monomeric ZFN that can cleave double stranded DNA without assistance from another ZFN. The term ZFN is also used to refer to one or both members of a pair of ZFNs that are engineered to work together to cleave DNA at the same site.

Without being limited by any scientific theory, because the DNA-binding specificities of zinc finger domains can in principle be re-engineered using one of various methods, customized ZFNs can theoretically be constructed to target nearly any gene sequence. Publicly available methods for engineering zinc finger domains include Context-dependent Assembly (CoDA), Oligomerized Pool Engineering (OPEN), and Modular Assembly.

TALENs are artificial restriction enzymes generated by fusing the transcription activator-like effector (TALE) DNA binding domain to a FokI nuclease domain. When each member of a TALEN pair binds to the DNA sites flanking a target site, the FokI monomers dimerize and cause a double-stranded DNA break at the target site. The term TALEN, as used herein, is broad and includes a monomeric TALEN that can cleave double stranded DNA without assistance from another TALEN. The term TALEN is also used to refer to one or both members of a pair of TALENs that work together to cleave DNA at the same site.

Transcription activator-like effectors (TALEs) can be engineered to bind practically any DNA sequence. TALE proteins are DNA-binding domains derived from various plant bacterial pathogens of the genus Xanthomonas. The Xanthomonas pathogens secrete TALEs into the host plant cell during infection. The TALE moves to the nucleus, where it recognizes and binds to a specific DNA sequence in the promoter region of a specific DNA sequence in the promoter region of a specific gene in the host genome. TALE has a central DNA-binding domain composed of 13-28 repeat monomers of 33-34 amino acids. The amino acids of each monomer are highly conserved, except for hypervariable amino acid residues at positions 12 and 13. The two variable amino acids are called repeat-variable diresidues (RVDs). The amino acid pairs NI, NG, HD, and NN of RVDs preferentially recognize adenine, thymine, cytosine, and guanine/adenine, respectively, and modulation of RVDs can recognize consecutive DNA bases. This simple relationship between amino acid sequence and DNA recognition has allowed for the engineering of specific DNA binding domains by selecting a combination of repeat segments containing the appropriate RVDs.

Besides the wild-type FokI cleavage domain, variants of the FokI cleavage domain with mutations have been designed to improve cleavage specificity and cleavage activity. The FokI domain functions as a dimer, requiring two constructs with unique DNA binding domains for sites in the target genome with proper orientation and spacing. Both the number of amino acid residues between the TALEN DNA binding domain and the FokI cleavage domain and the number of bases between the two individual TALEN binding sites are parameters for achieving high levels of activity.

A relationship between amino acid sequence and DNA recognition of the TALE binding domain allows for designable proteins. Software programs such as DNA Works can be used to design TALE constructs. Other methods of designing TALE constructs are known to those of skill in the art. See Doyle et al., *Nucleic Acids Research* (2012) 40: W117-122.; Cermak et al., *Nucleic Acids Research* (2011). 39:e82; and tale-nt.cac.cornell.edu/about.

A CRISPR/Cas9 system, CRISPR/Csm1, or a CRISPR/Cpf1 system are alternatives to the FokI-based methods ZFN and TALEN. The CRISPR systems are based on RNA-guided engineered nucleases that use complementary base pairing to recognize DNA sequences at target sites.

CRISPR/Cas9, CRISPR/Csm1, and a CRISPR/Cpf1 systems are part of the adaptive immune system of bacteria and archaea, protecting them against invading nucleic acids such as viruses by cleaving the foreign DNA in a sequence-dependent manner. The immunity is acquired by the integration of short fragments of the invading DNA known as spacers between two adjacent repeats at the proximal end of a CRISPR locus. The CRISPR arrays, including the spacers, are transcribed during subsequent encounters with invasive DNA and are processed into small interfering CRISPR RNAs (crRNAs) approximately 40 nt in length, which combine with the trans-activating CRISPR RNA (tracrRNA) to activate and guide the Cas9 nuclease. This cleaves homologous double-stranded DNA sequences known as protospacers in the invading DNA. A prerequisite for cleavage is the presence of a conserved protospacer-adjacent motif (PAM) downstream of the target DNA, which usually has the sequence 5-NGG-3 but less frequently NAG. Specificity is provided by the so-called "seed sequence" approximately 12 bases upstream of the PAM, which must match between the RNA and target DNA. Cpf1 and Csm1 act in a similar manner to Cas9, but Cpf1 and Csm1 do not require a tracrRNA.

Transgenes

The present disclosure also provides compositions and methods for activating or inhibiting the expression or function of one or more LQG genes in a plant, particularly plants of the *Nicotiana* genus, including tobacco plants of the various commercial varieties.

As used herein, the terms "inhibit," "inhibition," and "inhibiting" are defined as any method known in the art or described herein that decreases the expression or function of a gene product of interest (e.g., a target gene product). "Inhibition" can be in the context of a comparison between two plants, for example, a genetically altered plant versus a wild-type plant. Alternatively, inhibition of expression or function of a target gene product can be in the context of a comparison between plant cells, organelles, organs, tissues, or plant parts within the same plant or between different plants, and includes comparisons between developmental or temporal stages within the same plant or plant part or between plants or plant parts. "Inhibition" includes any relative decrement of function or production of a gene product of interest, up to and including complete elimination of function or production of that gene product. The term "inhibition" encompasses any method or composition that down-regulates translation and/or transcription of the target gene product or functional activity of the target gene product. In an aspect, the mRNA or protein level of one or more genes in a modified plant is less than 95%, less than 90%, less than 80%, less than 70%, less than 60%, less than 50%, less than 40%, less than 30%, less than 20%, less than 10%, less than 5%, less than 4%, less than 3%, less than 2%, or less than 1% of the mRNA or protein level of the same gene in a plant that is not a mutant or that has not been genetically modified to inhibit the expression of that gene.

The use of the term "polynucleotide" is not intended to limit the present disclosure to polynucleotides comprising DNA. Those of ordinary skill in the art will recognize that polynucleotides can comprise ribonucleotides and combinations of ribonucleotides and deoxyribonucleotides. Such deoxyribonucleotides and ribonucleotides include both naturally occurring molecules and synthetic analogues. The polynucleotides of the present disclosure also encompass all forms of sequences including, but not limited to, single-stranded forms, double-stranded forms, hairpins, stem-and-loop structures, and the like.

In an aspect, the present disclosure provides recombinant DNA constructs comprising a promoter that is functional in a tobacco cell and operably linked to a polynucleotide that encodes an RNA molecule capable of binding to an RNA encoding a polypeptide having an amino acid sequence at least 80%, at least 85%, at least 90%, at least 95%, at least 97%, at least 98%, at least 99% identical to an amino acid sequence selected from the group consisting of SEQ ID NOs: 18-34, and fragments thereof, and where the RNA molecule suppresses the expression of the polypeptide. In an aspect, the RNA molecule is selected from the group consisting of a microRNA, an siRNA, and a trans-acting siRNA. In another aspect, the recombinant DNA construct encodes a double stranded RNA. Also provided are transgenic tobacco plants or part thereof, cured tobacco material, or tobacco products comprising these recombinant DNA constructs. In an aspect, these transgenic plants, cured tobacco material, or tobacco products comprise a lower level of nicotine compared to a control tobacco plant without the recombinant DNA construct. Further provided are methods of reducing the nicotine level of a tobacco plant, the method comprising transforming a tobacco plant with any of these recombinant DNA constructs.

As used herein, "operably linked" refers to a functional linkage between two or more elements. For example, an operable linkage between a polynucleotide of interest and a regulatory sequence (e.g., a promoter) is a functional link that allows for expression of the polynucleotide of interest. Operably linked elements may be contiguous or non-contiguous.

As used herein and when used in reference to a sequence, "heterologous" refers to a sequence that originates from a foreign species, or, if from the same species, is substantially modified from its native form in composition and/or genomic location by deliberate human intervention. The term also is applicable to nucleic acid constructs, also referred to herein as "polynucleotide constructs" or "nucleotide constructs." In this manner, a "heterologous" nucleic acid construct is intended to mean a construct that originates from a foreign species, or, if from the same species, is substantially modified from its native form in composition and/or genomic location by deliberate human intervention. Heterologous nucleic acid constructs include, but are not limited to, recombinant nucleotide constructs that have been introduced into a plant or plant part thereof, for example, via transformation methods or subsequent breeding of a transgenic plant with another plant of interest. In an aspect, a promoter used is heterologous to the sequence driven by the promoter. In another aspect, a promoter used is heterologous to tobacco. In a further aspect, a promoter used is native to tobacco.

In an aspect, a modified tobacco plant described is a cisgenic plant. As used herein, "cisgenesis" or "cisgenic" refers to genetic modification of a plant, plant cell, or plant genome in which all components (e.g., promoter, donor nucleic acid, selection gene) have only plant origins (i.e., no non-plant origin components are used). In an aspect, a modified plant, plant cell, or plant genome provided is cisgenic. Cisgenic plants, plant cells, and plant genomes provided can lead to ready-to-use tobacco lines. In another aspect, a modified tobacco plant provided comprises no non-tobacco genetic material or sequences.

As used herein, "gene expression" refers to the biosynthesis or production of a gene product, including the transcription and/or translation of the gene product.

In an aspect, recombinant DNA constructs or expression cassettes can also comprise a selectable marker gene for the selection of transgenic cells. Selectable marker genes include, but are not limited to, genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). Additional selectable markers include phenotypic markers such as β-galactosidase and fluorescent proteins such as green fluorescent protein (GFP).

In an aspect, recombinant DNA constructs or expression cassettes comprise a promoter selected from the group consisting of a constitutive promoter, an inducible promoter, and a tissue-preferred promoter (for example, a leaf-specific or root-specific promoter). Exemplary constitutive promoters include the core promoter of the Rsyn7 promoter and other constitutive promoters disclosed in U.S. Pat. No. 6,072,050; the core CaMV 35S promoter (Odell et al. (1985) Nature 313:810-812); ubiquitin (Christensen et al. (1989) Plant Mol. Biol. 12:619-632 and Christensen et al. (1992) Plant Mol. Biol. 18:675-689); pEMU (Last et al. (1991) Theor. Appl. Genet. 81:581-588); MAS (Velten et al. (1984) EMBO J 3:2723-2730); ALS promoter (U.S. Pat. No. 5,659, 026), and the like. Exemplary chemical-inducible promoters include the tobacco PR-1a promoter, which is activated by salicylic acid. Other chemical-inducible promoters of interest include steroid-responsive promoters (see, for example, the glucocorticoid-inducible promoter in Schena et al. (1991) Proc. Natl. Acad. Sci. USA 88:10421-10425 and McNellis et al. (1998) Plant J. 14(2):247-257) and tetracycline-inducible promoters (see, for example, Gatz et al. (1991) Mol. Gen. Genet. 227:229-237, and U.S. Pat. Nos. 5,814,618 and 5,789,156). Additional exemplary promoters that can be used are those responsible for heat-regulated gene expression, light-regulated gene expression (for example, the pea rbcS-3A; the maize rbcS promoter; the chlorophyll alb-binding protein gene found in pea; or the Arabssu promoter), hormone-regulated gene expression (for example, the abscisic acid (ABA) responsive sequences from the Em gene of wheat; the ABA-inducible HVA1 and HVA22, and rd29A promoters of barley and *Arabidopsis*; and wound-induced gene expression (for example, of wunl), organ specific gene expression (for example, of the tuber-specific storage protein gene; the 23-kDa zein gene from maize described by; or the French bean (β-phaseolin gene), or pathogen-inducible promoters (for example, the PR-1, prp-1, or (β-1,3 glucanase promoters, the fungal-inducible wirla promoter of wheat, and the nematode-inducible promoters, TobRB7-5A and Hmg-1, of tobacco arid parsley, respectively).

In an aspect, a tobacco plant provided further comprises increased or reduced expression of activity of genes involved in nicotine biosynthesis or transport. Genes involved in nicotine biosynthesis include, but are not limited to, arginine decarboxylase (ADC), methylputrescine oxidase (MPO), NADH dehydrogenase, ornithine decarboxylase (ODC), phosphoribosylanthranilate isomerase (PRAI), putrescine N-methyltransferase (PMT), quinolate phosphoribosyl transferase (QPT), and S-adenosyl-methionine synthetase (SAMS). Nicotine Synthase, which catalyzes the condensation step between a nicotinic acid derivative and methylpyrrolinium cation, has not been elucidated although two candidate genes (A622 and NBB1) have been proposed. See US 2007/0240728 A1 and US 2008/0120737A1. A622 encodes an isoflavone reductase-like protein. In addition, several transporters may be involved in the translocation of nicotine. A transporter gene, named MATE, has been cloned and characterized (Morita et al., *PNAS* 106:2447-52 (2009)).

In an aspect, a tobacco plant provided further comprises an increased or reduced level of mRNA, protein, or both of one or more genes encoding a product selected from the group consisting of PMT, MPO, QPT, ADC, ODC, PRAI, SAMS, BBL, MATE, A622, and NBB1, compared to a control tobacco plant. In another aspect, a tobacco plants provided further comprises a transgene directly suppressing the expression of one or more genes encoding a product selected from the group consisting of PMT, MPO, QPT, ADC, ODC, PRAI, SAMS, BBL, MATE, A622, and NBB1. In another aspect, a tobacco plant provided further comprises a transgene or mutation suppressing the expression or activity of one or more genes encoding a product selected from the group consisting of PMT, MPO, QPT, ADC, ODC, PRAI, SAMS, BBL, MATE, A622, and NBB1. In another aspect, a tobacco plant provided further comprises a transgene overexpressing one or more genes encoding a product selected from the group consisting of PMT, MPO, QPT, ADC, ODC, PRAI, SAMS, BBL, MATE, A622, and NBB1.

Also disclosed are the transformation of tobacco plants with recombinant constructs or expression cassettes described using any suitable transformation methods known in the art. Methods for introducing polynucleotide sequences into tobacco plants are known in the art and include, but are not limited to, stable transformation methods, transient transformation methods, and virus-mediated methods. "Stable transformation" refers to transformation where the nucleotide construct of interest introduced into a plant integrates into the genome of the plant and is capable of being inherited by the progeny thereof. "Transient transformation" is intended to mean that a sequence is introduced into the plant and is only temporally expressed or is only transiently present in the plant.

Suitable methods of introducing polynucleotides into plant cells of the present disclosure include microinjection (Crossway et al. (1986) *Biotechniques* 4:320-334), electroporation (Shillito et al. (1987) *Meth. Enzymol.* 153:313-336; Riggs et al. (1986) *Proc. Natl. Acad. Sci. USA* 83:5602-5606), *Agrobacterium*-mediated transformation (U.S. Pat. Nos. 5,104,310, 5,149,645, 5,177,010, 5,231,019, 5,463,174, 5,464,763, 5,469,976, 4,762,785, 5,004,863, 5,159,135, 5,563,055, and 5,981,840), direct gene transfer (Paszkowski et al. (1984) *EMBO J* 3:2717-2722), and ballistic particle acceleration (see, for example, U.S. Pat. Nos. 4,945,050, 5,141,131, 5,886,244, 5,879,918, and 5,932,782; Tomes et al. (1995) in *Plant Cell, Tissue, and Organ Culture Fundamental Methods*, ed. Gamborg and Phillips (Springer-Verlag, Berlin); McCabe et al. (1988) *Biotechnology* 6:923-926). Also see Weissinger et al. (1988) *Ann. Rev. Genet.* 22:421-477; Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P: 175-182 (soybean); Singh et al. (1998) *Theor. Appl. Genet.* 96:319-324 (soybean); De Wet et al. (1985) in *The Experimental Manipulation of Ovule Tissues*, ed. Chapman et al. (Longman, N.Y.), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation).

In another aspect, recombinant constructs or expression cassettes may be introduced into plants by contacting plants with a virus or viral nucleic acids. Generally, such methods involve incorporating an expression cassette of the present disclosure within a viral DNA or RNA molecule. It is recognized that promoters for use in expression cassettes also encompass promoters utilized for transcription by viral RNA polymerases. Methods for introducing polynucleotides into plants and expressing a protein encoded therein, involving viral DNA or RNA molecules, are known in the art. See, for example, U.S. Pat. Nos. 5,889,191, 5,889,190, 5,866, 785, 5,589,367, 5,316,931, and Porta et al. (1996) *Molecular Biotechnology* 5:209-221.

Any plant tissue that can be subsequently propagated using clonal methods, whether by organogenesis or embryogenesis, may be transformed with a recombinant construct or an expression cassette. By "organogenesis" in intended the process by which shoots and roots are developed sequentially from meristematic centers. By "embryogenesis" is intended the process by which shoots and roots develop together in a concerted fashion (not sequentially), whether from somatic cells or gametes. Exemplary tissues that are suitable for various transformation protocols described include, but are not limited to, callus tissue, existing meristematic tissue (e.g., apical meristems, axillary buds, and root meristems) and induced meristem tissue (e.g., cotyledon meristem and hypocotyl meristem), hypocotyls, cotyledons, leaf disks, pollen, embryos, and the like.

Promoters

In an aspect, the present disclosure provides a tobacco plant, or part thereof, comprising a transgene targeting LQG gene (e.g., as in a "LQG transgenic plant"). Various types of promoters can be used in a LQG transgene or recombinant nucleic acid described here, which are classified according to a variety of criteria relating to the pattern of expression of a coding sequence or gene (including a transgene) operably linked to the promoter, such as constitutive, developmental, tissue-specific, tissue-preferred, inducible, etc. Promoters that initiate transcription in all or most tissues of the plant are referred to as "constitutive" promoters. Promoters that initiate transcription during certain periods or stages of development are referred to as "developmental" promoters. Promoters whose expression is enhanced in certain tissues of the plant relative to other plant tissues are referred to as "tissue-enhanced" or "tissue-preferred" promoters. Thus, a "tissue-preferred" promoter causes relatively higher or preferential expression in a specific tissue(s) of the plant, but with lower levels of expression in other tissue(s) of the plant. Promoters that express within a specific tissue(s) of the plant, with little or no expression in other plant tissues, are referred to as "tissue-specific" promoters. A promoter that expresses in a certain cell type of the plant is referred to as a "cell type specific" promoter. An "inducible" promoter is a promoter that initiates transcription in response to an environmental stimulus such as cold, drought, heat or light, or other stimuli, such as wounding or chemical application. Also used here are promoters that are classified in terms of its origin, such as being heterologous, homologous, chimeric, synthetic, etc. A "heterologous" promoter is a promoter sequence having a different origin relative to its associated transcribable sequence, coding sequence, or gene (or transgene), and/or not naturally occurring in the plant species to be transformed. The term "heterologous" more broadly includes a combination of two or more DNA molecules or sequences when such a combination is not normally found in nature. For example, two or more DNA molecules or sequences would be heterologous with respect to each other if they are normally found in different genomes or at different loci in the same genome, or if they are not identically combined in nature.

In an aspect, a LQG transgene comprising an inducible promoter. In one aspect, an inducible promoter is a topping-inducible promoter. In an aspect, an inducible promoter is also a tissue-specific or tissue-preferred promoter. In one aspect, a tissue-specific or tissue-preferred promoter is specific or preferred for one or more tissues or organs selected from the group consisting of shoot, root, leaf, stem, flower, sucker, root tip, mesophyll cells, epidermal cells, and vasculature. In a further aspect, a topping inducible promoter comprises a promoter sequence from a tobacco nicotine demethylase gene, for example, CYP82E4, CYP82E5, or CYP82E10. In an aspect, an inducible promoter provides root specific or preferred expression. Exemplary root specific or preferred inducible promoter can be found in U.S. Patent Application Publication No. 2019/0271000. In an aspect, an inducible promoter provides leaf specific or preferred expression. Exemplary leaf specific or preferred inducible promoter can be found in U.S. Patent Application Publication No. 2019/0271000, which is herein incorporated by reference in its entirety.

In an aspect, an inducible promoter is a heterologous to the operably linked transcribable DNA sequence. In one aspect, a transcribable DNA sequence encodes a non-coding RNA selected from the group consisting of microRNA (miRNA), anti-sense RNA, small interfering RNA (siRNA), a trans-acting siRNA (ta-siRNA), and hairpin RNA (hpRNA). In an aspect, a non-coding RNA comprises a nucleotide sequence having at least 99.9%, at least 99.5%, at least 99%, at least 98%, at least 97%, at least 96%, at least 95%, at least 94%, at least 93%, at least 92%, at least 91%, at least 90%, at least 85%, at least 80%, or at least 75% identity to a sequence selected from the group consisting of SEQ ID Nos: 1-17, and any portions thereof.

Tobacco Types

In an aspect, a tobacco plant provided is from a tobacco type selected from the group consisting of flue-cured tobacco, air-cured tobacco, dark air-cured tobacco, dark fire-cured tobacco, Galpão tobacco, and Oriental tobacco. In another aspect, a tobacco plant provided is from a tobacco type selected from the group consisting of Burley tobacco, Maryland tobacco, and dark tobacco.

In an aspect, a tobacco plant provided is in a flue-cured tobacco background or exhibits one or more flue-cured tobacco characteristic described here. Flue-cured tobaccos (also called "Virginia" or "bright" tobaccos) amount to approximately 40% of world tobacco production. Flue-cured tobaccos are often also referred to as "bright tobacco" because of the golden-yellow to deep-orange color it reaches during curing. Flue-cured tobaccos have a light, bright aroma and taste. Flue-cured tobaccos are generally high in sugar and low in oils. Major flue-cured tobacco growing countries are Argentina, Brazil, China, India, Tanzania and the United States of America. In one aspect, tobacco plants or seeds or modified tobacco plants or seeds provided herein are of a flue-cured tobacco variety selected from the group consisting of the varieties listed in Table 1, and any variety essentially derived from any one of the foregoing varieties. See WO 2004/041006 A1. In a further aspect, modified tobacco plants or seeds provided herein are in a flue-cured variety selected from the group consisting of K326, K346, and NC196.

TABLE 1

| Flue-cured Tobacco Varieties |
|---|
| 400 (TC 225) |
| 401 (TC 226) |
| 401 Cherry Red (TC 227) |
| 401 Cherry Red Free (TC 228) |
| Cash (TC 250) |
| Cash (TI 278) |
| CC 101 |
| CC 1063 |
| CC 13 |
| CC 143 |
| CC 200 |
| CC 27 |
| CC 301 |
| CC 33 |
| CC 35 |
| CC 37 |
| CC 400 |
| CC 500 |
| CC 600 |
| CC 65 |
| CC 67 |
| CC 700 |
| CC 800 |
| CC 900 |
| Coker 139 (TC 259) |
| Coker 139 yb1, yb2 |
| Coker 140 (TC 260) |
| Coker 176 (TC 262) |
| Coker 187 (TC 263) |
| Coker 187-Hicks (TC 265) |
| Coker 209 (TC 267) |
| Coker 258 (TC 270) |

TABLE 1-continued

Flue-cured Tobacco Varieties

Coker 298 (TC 272)
Coker 316 (TC 273)
Coker 319 (TC 274)
Coker 347 (TC 275)
Coker 371-Gold (TC 276)
Coker 411 (TC 277)
Coker 48 (TC 253)
Coker 51 (TC 254)
Coker 86 (TC 256)
CU 263 (TC 619)
CU 561
DH95-1562-1
Dixie Bright 101 (TC 290)
Dixie Bright 102 (TC 291)
Dixie Bright 244 (TC 292)
Dixie Bright 27 (TC 288)
Dixie Bright 28 (TC 289)
GF 157
GF 318
GL 26H
GL 338
GL 350
GL 368
GL 395
GL 600
GL 737
GL 939
GL 939 (TC 628)
Hicks (TC 310)
Hicks Broadleaf (TC 311)
K 149 (TC 568)
K 317
K 326
K 326 (TC 319)
K 340 (TC 320)
K 346
K 346 (TC 569)
K 358
K 394 (TC 321)
K 399
K 399 (TC 322)
K 730
Lonibow (TI 1573)
Lonibow (TI 1613)
McNair 10 (TC 330)
McNair 135 (TC 337)
McNair 30 (TC 334)
McNair 373 (TC 338)
McNair 944 (TC 339)
MK94 (TI 1512)
MS K 326
MS NC 71
MS NC 72
NC 100
NC 102
NC 1071 (TC 364)
NC 1125-2
NC 12 (TC 346)
NC 1226
NC 196
NC 2326 (TC 365)
NC 27 NF (TC 349)
NC 291
NC 297
NC 299
NC 37 NF (TC 350)
NC 471
NC 55
NC 567 (TC 362)
NC 60 (TC 352)
NC 606
NC 6140
NC 71
NC 72
NC 729 (TC 557)
NC 810 (TC 659)
NC 82 (TC 356)
NC 8640
NC 89 (TC 359)
NC 92
NC 925
NC 95 (TC 360)
NC 98 (TC 361)
NC EX 24
NC PY 10 (TC 367)
NC TG 61
Oxford 1 (TC 369)
Oxford 1-181 (TC 370)
Oxford 2 (TC 371)
Oxford 207 (TC 632)
Oxford 26 (TC 373)
Oxford 3 (TC 372)
Oxford 414 NF
PD 611 (TC 387)
PVH 03
PVH 09
PVH 1118
PVH 1452
PVH 1600
PVH 2110
PVH 2275
R 83 (Line 256-1) (TI 1400)
Reams 134
Reams 158
Reams 713
Reams 744
Reams M1
RG 11 (TC 600)
RG 13 (TC 601)
RG 17 (TC 627)
RG 22 (TC 584)
RG 8 (TC 585)
RG 81 (TC 618)
RG H51
RG4H 217
RGH 12
RGH 4
RGH 51
RGH 61
SC 58 (TC 400)
SC 72 (TC 403)
Sp. G-168
SPEIGHT 168
Speight 168 (TC 633)
Speight 172 (TC 634)
Speight 178
Speight 179
Speight 190
Speight 196
SPEIGHT 220
SPEIGHT 225
SPEIGHT 227
SPEIGHT 236
Speight G-10 (TC 416)
Speight G-102
Speight G-108
Speight G-111
Speight G-117
Speight G-126
Speight G-15 (TC 418)
Speight G-23
Speight G-28 (TC 420)
Speight G-33
Speight G-41
Speight G-5
Speight G-52
Speight G-58
Speight G-70
Speight G-70 (TC 426)
Speight G-80 (TC 427)
Speight NF3 (TC 629)
STNCB
VA 182
VA 45 (TC 559)
Vesta 30 (TC 439)
Vesta 33 (TC 440)

TABLE 1-continued

Flue-cured Tobacco Varieties

Vesta 5 (TC 438)
Vesta 62 (TC 441)
Virginia (TI 220)
Virginia (TI 273)
Virginia (TI 877)
Virginia 115 (TC 444)
Virginia 21 (TC 443)
Virginia Bright (TI 964)
Virginia Bright Leaf (TC 446)
Virginia Gold (TC 447)
White Stem Orinoco (TC 451)

In an aspect, a tobacco plant provided is in an air-cured tobacco background or exhibits one or more air-cured tobacco characteristic described here. Air-cured tobaccos include "Burley," "Maryland," and "dark" tobaccos. The common factor linking air-cured tobaccos is that curing occurs primarily without artificial sources of heat and humidity. Burley tobaccos are light to dark brown in color, high in oil, and low in sugar. Burley tobaccos are typically air-cured in barns. Major Burley growing countries include Argentina, Brazil, Italy, Malawi, and the United States of America.

Maryland tobaccos are extremely fluffy, have good burning properties, low nicotine and a neutral aroma. Major Maryland growing countries include the United States of America and Italy.

In one aspect, tobacco plants or seeds or modified tobacco plants or seeds provided herein are of a Burley tobacco variety selected from the group consisting of the tobacco varieties listed in Table 2, and any variety essentially derived from any one of the foregoing varieties. In a further aspect, modified tobacco plants or seeds provided herein are in a Burley variety selected from the group consisting of TN 90, KT 209, KT 206, KT212, and HB 4488.

TABLE 2

Burley Tobacco Varieties

4407 LC
AA-37-1
Burley 21 (TC 7)
Burley 49 (TC 10)
Burley 64 (TC 11)
Burley Mammoth KY 16 (TC 12)
Clay 402
Clay 403
Clay 502
Clays 403
GR 10 (TC 19)
GR 10 (TC 19)
GR 10A (TC 20)
GR 13 (TC 21)
GR 14 (TC 22)
GR 149 LC
GR 153
GR 17 (TC 23)
GR 17B (TC 24)
GR 18 (TC 25)
GR 19 (TC 26)
GR 2 (TC 15)
GR 24 (TC 27)
GR 36 (TC 28)
GR 38 (TC 29)
GR 38A (TC 30)
GR 40 (TC 31)
GR 42 (TC 32)
GR 42C (TC 33)
GR 43 (TC 34)
GR 44 (TC 35)

TABLE 2-continued

Burley Tobacco Varieties

GR 45 (TC 36)
GR 46 (TC 37)
GR 48 (TC 38)
GR 5 (TC 16)
GR 53 (TC 39)
GR 6 (TC 17)
GR 9 (TC 18)
GR139 NS
GR139 S
HB 04P
HB 04P LC
HB 3307P LC
HB 4108P
HB 4151P
HB 4192P
HB 4194P
HB 4196
HB 4488
HB 4488P
HB04P
HB 4488 LC
HIB 21
HPB 21
HY 403
Hybrid 403 LC
Hybrid 404 LC
Hybrid 501 LC
KDH-959 (TC 576)
KDH-960 (TC 577)
KT 200 LC
KT 204 LC
KT 206 LC
KT 209 LC
KT 210 LC
KT 212 LC
KT 215 LC
KY 1 (TC 52)
KY 10 (TC 55)
KY 12 (TC 56)
KY 14 (TC 57)
KY 14 × L8 LC
KY 15 (TC 58)
KY 16 (TC 59)
KY 17 (TC 60)
KY 19 (TC 61)
KY 21 (TC 62)
KY 22 (TC 63)
KY 24 (TC 64)
KY 26 (TC 65)
KY 33 (TC 66)
KY 34 (TC 67)
KY 35 (TC 68)
KY 41A (TC 69)
KY 5 (TC 53)
KY 52 (TC 70)
KY 54 (TC 71)
KY 56 (TC 72)
KY 56 (TC 72)
KY 57 (TC 73)
KY 58 (TC 74)
KY 8654 (TC 77)
KY 8959
KY 9 (TC 54)
KY 907 LC
KY 908 (TC 630)
NBH 98 (Screened)
NC 1206
NC 129
NC 2000 LC
NC 2002 LC
NC 3 LC
NC 5 LC
NC 6 LC
NC 7 LC
NC BH 129 LC
NC03-42-2
Newton 98
R 610 LC

TABLE 2-continued

Burley Tobacco Varieties

R 630 LC
R 7-11
R 7-12 LC
RG 17
TKF 1801 LC
TKF 2002 LC
TKF 4024 LC
TKF 4028 LC
TKF 6400 LC
TKF 7002 LC
TKS 2002 LC
TN 86 (TC 82)
TN 90 LC
TN 97 Hybrid LC
TN 97 LC
VA 116
VA 119
Virgin A Mutante (TI 1406)
Virginia 509 (TC 84)

In another aspect, tobacco plants or seeds or modified tobacco plants or seeds provided herein are of a Maryland tobacco variety selected from the group consisting of the tobacco varieties listed in Table 3, and any variety essentially derived from any one of the foregoing varieties.

TABLE 3

Maryland Tobacco Varieties

Maryland 10 (TC 498)
Maryland 14 D2 (TC 499)
Maryland 201 (TC 503)
Maryland 21 (TC 500)
Maryland 341 (TC 504)
Maryland 40
Maryland 402
Maryland 59 (TC 501)
Maryland 601
Maryland 609 (TC 505)
Maryland 64 (TC 502)
Maryland 872 (TC 506)
Maryland Mammoth (TC 507)

In an aspect, a tobacco plant provided is in a dark air-cured tobacco background or exhibits one or more dark air-cured tobacco characteristic described here. Dark air-cured tobaccos are distinguished from other tobacco types primarily by its curing process, which gives dark air-cured tobacco its medium-brown to dark-brown color and a distinct aroma. Dark air-cured tobaccos are mainly used in the production of chewing tobacco and snuff. In one aspect, modified tobacco plants or seeds provided herein are of a dark air-cured tobacco variety selected from the group consisting of Sumatra, Jatim, Dominican Cubano, Besuki, One sucker, Green River, Virginia sun-cured, and Paraguan Passado, and any variety essentially derived from any one of the foregoing varieties.

In an aspect, a tobacco plant provided is in a dark fire-cured tobacco background or exhibits one or more dark fire-cured tobacco characteristic described here. Dark fire-cured tobaccos are generally cured with low-burning wood fires on the floors of closed curing barns. Dark fire-cured tobaccos are typically used for making pipe blends, cigarettes, chewing tobacco, snuff, and strong-tasting cigars. Major growing regions for dark fire-cured tobaccos are Tennessee, Kentucky, and Virginia in the United States of America. In one aspect, tobacco plants or seeds or modified tobacco plants or seeds provided herein are of a dark fire-cured tobacco variety selected from the group consisting of the tobacco varieties listed in Table 4, and any variety essentially derived from any one of the foregoing varieties.

TABLE 4

Dark Fire-Cured Tobacco Varieties

Black Mammoth (TC 461)
Black Mammoth Small Stalk (TC 641)
Certified Madole (TC 463)
D-534-A-1 (TC 464)
DAC ULT 302
DAC ULT 303
DAC ULT 306
DAC ULT 308
DAC ULT 312
DF 300 (TC 465)
DF 485 (TC 466)
DF 516 (TC 467)
DF 911 (TC 468)
DT 508
DT 518 (Screened)
DT 538 LC
DT 592
Improved Madole (TC 471)
Jernigan's Madole (TC 472)
KT 14LC
KT D17LC
KT D4 LC
KT D6 LC
KT D8 LC
KY 153 (TC 216)
KY 157 (TC 217)
KY 160
KY 160 (TC 218)
KY 163 (TC 219)
KY 165 (TC 220)
KY 170 (TC 474)
KY 171 (PhPh)
KY 171 (TC 475)
KY 171 LC
KY 171 NS
KY 180 (TC 573)
KY 190 (TC 574)
Little Crittenden
Little Crittenden (TC 476)
Little Crittenden LC (certified)
Little Crittenden PhPh
Lizard Tail Turtle Foot
Madole (TC 478)
Madole (TC 479)
MS KY 171
MS NL Madole LC
MS TN D950 LC
Nance (TC 616)
Narrow Leaf Madole LC (certified)
Neal Smith Madole (TC 646)
Newtons VH Madole
NL Madole
NL Madole (PhPh)
NL Madole (TC 484)
NL Madole LC
NL Madole LC (PhPh)
NL Madole NS
One Sucker (TC 224)
OS 400
PD 302H
PD 312H
PD 318H
PD 7302 LC
PD 7305
PD 7309 LC
PD 7312 LC
PD 7318 LC
PD 7319 LC
Petico M PG04
PY KY 160 (TC 612)
PY KY 171 (TC 613)
Shirey
TI 1372

TABLE 4-continued

Dark Fire-Cured Tobacco Varieties

TN D94
TN D94 (TC 621)
TN D950
TN D950 (PhPh)
TN D950
TN D950 (TC 622)
TR Madole (TC 486)
VA 309
VA 309 (TC 560)
VA 309 LC (certified)
VA 310 (TC 487)
VA 331 (TC 592)
VA 355 (TC 638)
VA 359
VA 359 (Screened)
VA 359 (TC 639)
VA 359 LC (certified)
VA 403 (TC 580)
VA 405 (TC 581)
VA 409 (TC 562)
VA 510 (TC 572)

In an aspect, a tobacco plant provided is in an Oriental tobacco background or exhibits one or more Oriental tobacco characteristic described here. Oriental tobaccos are also referred to as Greek, aroma and Turkish tobaccos due to the fact that they are typically grown in eastern Mediterranean regions such as Turkey, Greece, Bulgaria, Macedonia, Syria, Lebanon, Italy, and Romania. The small plant size, small leaf size, and unique aroma properties of Oriental tobacco varieties are a result of their adaptation to the poor soil and stressful climatic conditions in which they have been developed. In one aspect, tobacco plants or seeds or modified tobacco plants or seeds provided herein are of an Oriental tobacco variety selected from the group consisting of the tobacco varieties listed in Table 5, and any variety essentially derived from any one of the foregoing varieties.

TABLE 5

Oriental Tobacco Varieties.

Bafra (TI 1641)
Bahce (TI 1730)
Bahia (TI 1416)
Bahia (TI 1455)
Baiano (TI 128)
Basma
Basma (TI 1666)
Basma Drama
Basma Hybrid (PhPh)
Basma Zihna I
Bitlis (TI 1667)
Bitlis (TI 1725)
Bubalovac (TI 1282)
Bursa (TI 1650)
Bursa (TI 1668)
Canik (TI 1644)
Djebel 174 (TI 1492)
Djebel 359 (TI 1493)
Djebel 81
Dubec 566 (TI 1409)
Dubec 7 (TI 1410)
Dubek 566 (TI 1567)
Duzce (TI 1670)
Edirne (TI 1671)
Ege (TI 1642)
Ege-64 (TI 1672)
Izmir (Akhisar) (TI 1729)
Izmir (Gavurkoy) (TI 1727)
Izmir Ege 64
Izmir-Incekara (TI 1674)
Izmir-Ozbas (TI 1675)

TABLE 5-continued

Oriental Tobacco Varieties.

Jaka Dzebel (TI 1326)
Kaba-Kulak
Kagoshima Maruba (TI 158)
Katerini
Katerini S53
Krumovgrad 58
MS Basma
MS Katerini S53
Nevrokop 1146
Ozbas (TI 1645)
Perustitza (TI 980)
Prilep (TI 1291)
Prilep (TI 1325)
Prilep 12-2/1
Prilep 23
Samsun (TC 536)
Samsun 959 (TI 1570)
Samsun Evkaf (TI 1723)
Samsun Holmes NN (TC 540)
Samsun Maden (TI 1647)
Samsun NO 15 (TC 541)
Samsun-BLK SHK Tol (TC 542)
Samsun-Canik (TI 1678)
Samsun-Maden (TI 1679)
Saribaptar 407 - Izmir Region
Smyrna (TC 543)
Smyrna No. 23 (TC 545)
Smyrna No. 9 (TC 544)
Smyrna-Blk Shk Tol (TC 546)
Trabzon (TI 1649)
Trabzon (TI 1682)
Trapezund 161 (TI 1407)
Turkish (TC 548)
Turkish Angshit (TI 90)
Turkish Samsum (TI 92)
Turkish Tropizoid (TI 93)
Turkish Varotic (TI 89)
Xanthi (TI 1662)

In an aspect, tobacco plants or seeds or modified tobacco plants or seeds provided herein are of an cigar tobacco variety selected from the group consisting of the tobacco varieties listed in Table 6, and any variety essentially derived from any one of the foregoing varieties.

TABLE 6

Cigar Tobacco Varieties

Bahai (TI 62)
Beinhart 1000
Beinhart 1000 (TI 1562)
Beinhart 1000-1 (TI 1561)
Bergerac C
Bergerac C (TI 1529)
Big Cuban (TI 1565)
Castillo Negro, Blanco, Pina (TI 448)
Castillo Negro, Blanco, Pina (TI 448A)
Castillo Negro, Blanco, Pina (TI 449)
Caujaro (TI 893)
Chocoa (TI 289)
Chocoa (TI 313)
Connecticut 15 (TC 183)
Connecticut Broadleaf
Connecticut Broadleaf (TC 186)
Connecticut Shade (TC 188)
Criollo, Colorado (TI 1093)
Enshu (TI 1586)
Florida 301

TABLE 6-continued

Cigar Tobacco Varieties

Florida 301 (TC 195)
PA Broadleaf (TC 119)
Pennsylvania Broadleaf
Pennsylvania Broadleaf (TC 119)
Petite Havana SR1
Petite Havana SR1 (TC 105)

In an aspect, tobacco plants or seeds or modified tobacco plants or seeds provided herein are of a tobacco variety selected from the group consisting of the tobacco varieties listed in Table 7, and any variety essentially derived from any one of the foregoing varieties.

TABLE 7

Other Tobacco Varieties

Chocoa (TI 319)
Hoja Parada (TI 1089)
Hoja Parado (Galpoa) (TI 1068)
Perique (St. James Parrish)
Perique (TC 556)
Perique (TI 1374)
Sylvestris (TI 984)
TI 179

In an aspect, a modified tobacco plant, seed, or cell described here is from a variety selected from the group consisting of the tobacco varieties listed in Table 1, Table 2, Table 3, Table 4, Table 5, Table 6, and Table 7.

In an aspect, low-alkaloid or low-nicotine tobacco plants, seeds, hybrids, varieties, or lines are essentially derived from or in the genetic background of BU 64, CC 101, CC 200, CC 27, CC 301, CC 400, CC 500, CC 600, CC 700, CC 800, CC 900, Coker 176, Coker 319, Coker 371 Gold, Coker 48, CU 263, DF911, Galpao tobacco, GL 26H, GL 350, GL 600, GL 737, GL 939, GL 973, HB 04P, K 149, K 326, K 346, K 358, K394, K 399, K 730, KDH 959, KT 200, KT204LC, KY 10, KY 14, KY 160, KY 17, KY 171, KY 907, KY907LC, KTY14×L8 LC, Little Crittenden, McNair 373, McNair 944, msKY 14×L8, Narrow Leaf Madole, NC 100, NC 102, NC 2000, NC 291, NC 297, NC 299, NC 3, NC 4, NC 5, NC 6, NC7, NC 606, NC 71, NC 72, NC 810, NC BH 129, NC 2002, Neal Smith Madole, OXFORD 207, 'Perique' tobacco, PVH03, PVH09, PVH19, PVH50, PVH51, R 610, R 630, R 7-11, R 7-12, RG 17, RG 81, RG H51, RGH 4, RGH 51, RS 1410, Speight 168, Speight 172, Speight 179, Speight 210, Speight 220, Speight 225, Speight 227, Speight 234, Speight G-28, Speight G-70, Speight H-6, Speight H20, Speight NF3, TI 1406, TI 1269, TN 86, TN86LC, TN 90, TN 97, TN97LC, TN D94, TN D950, TR (Tom Rosson) Madole, VA 309, or VA359, Maryland 609, HB3307PLC, HB4488PLC, KT206LC, KT209LC, KT210LC, KT212LC, R610LC, PVH2310, NC196, KTD14LC, KTD6LC, KTD8LC, PD7302LC, PD7305LC, PD7309LC, PD7318LC, PD7319LC, PD7312LC, ShireyLC, or any commercial tobacco variety according to standard tobacco breeding techniques known in the art.

All foregoing mentioned specific varieties of dark air-cured, Burley, Maryland, dark fire-cured, or Oriental type are listed only for exemplary purposes. Any additional dark air-cured, Burley, Maryland, dark fire-cured, Oriental varieties are also contemplated in the present application.

Also provided are populations of tobacco plants described. In an aspect, a population of tobacco plants has a planting density of between about 5,000 and about 8,000, between about 5,000 and about 7,600, between about 5,000 and about 7,200, between about 5,000 and about 6,800, between about 5,000 and about 6,400, between about 5,000 and about 6,000, between about 5,000 and about 5,600, between about 5,000 and about 5,200, between about 5,200 and about 8,000, between about 5,600 and about 8,000, between about 6,000 and about 8,000, between about 6,400 and about 8,000, between about 6,800 and about 8,000, between about 7,200 and about 8,000, or between about 7,600 and about 8,000 plants per acre. In another aspect, a population of tobacco plants is in a soil type with low to medium fertility.

Also provided are containers of seeds from tobacco plants described. A container of tobacco seeds of the present disclosure may contain any number, weight, or volume of seeds. For example, a container can contain at least, or greater than, about 100, 200, 300, 400, 500, 600, 700, 800, 900, 1000, 1500, 2000, 2500, 3000, 3500, 4000 or more seeds. Alternatively, the container can contain at least, or greater than, about 50, 100, 200, 300, 400, 500, 600, 700, 800, 900, 1000, 1500, 2000, 2500, 3000, 3500, 4000 grams or more seeds. Containers of tobacco seeds may be any container available in the art. By way of non-limiting example, a container may be a box, a bag, a packet, a pouch, a tape roll, a tube, or a bottle.

Curing/Products

Also provided is cured tobacco material made from a low-alkaloid or low-nicotine tobacco plant described. Further provided is cured tobacco material made from a tobacco plant described with higher levels of total alkaloid or nicotine.

"Curing" is the aging process that reduces moisture and brings about the destruction of chlorophyll giving tobacco leaves a golden color and by which starch is converted to sugar. Cured tobacco therefore has a higher reducing sugar content and a lower starch content compared to harvested green leaf. In an aspect, green leaf tobacco provided can be cured using conventional means, e.g., flue-cured, barn-cured, fire-cured, air-cured or sun-cured. See, for example, Tso (1999, Chapter 1 in Tobacco, Production, Chemistry and Technology, Davis & Nielsen, eds., Blackwell Publishing, Oxford) for a description of different types of curing methods. Cured tobacco is usually aged in a wooden drum (e.g., a hogshead) or cardboard cartons in compressed conditions for several years (e.g., two to five years), at a moisture content ranging from 10% to about 25%. See, U.S. Pat. Nos. 4,516,590 and 5,372,149. Cured and aged tobacco then can be further processed. Further processing includes conditioning the tobacco under vacuum with or without the introduction of steam at various temperatures, pasteurization, and fermentation. Fermentation typically is characterized by high initial moisture content, heat generation, and a 10 to 20% loss of dry weight. See, e.g., U.S. Pat. Nos. 4,528,993, 4,660,577, 4,848,373, 5,372,149; U.S. Publication No. 2005/0178398; and Tso (1999, Chapter 1 in Tobacco, Production, Chemistry and Technology, Davis & Nielsen, eds., Blackwell Publishing, Oxford). Cure, aged, and fermented tobacco can be further processed (e.g., cut, shredded, expanded, or blended). See, for example, U.S. Pat. Nos. 4,528,993; 4,660,577; and 4,987,907. In an aspect, the cured tobacco material of the present disclosure is sun-cured. In another aspect, the cured tobacco material of the present disclosure is flue-cured, air-cured, or fire-cured.

Tobacco material obtained from the tobacco lines, varieties or hybrids of the present disclosure can be used to make tobacco products. As used herein, "tobacco product" is defined as any product made or derived from tobacco that is intended for human use or consumption.

Tobacco products provided include, without limitation, cigarette products (e.g., cigarettes and bidi cigarettes), cigar products (e.g., cigar wrapping tobacco and cigarillos), pipe tobacco products, products derived from tobacco, tobacco-derived nicotine products, smokeless tobacco products (e.g., moist snuff, dry snuff, and chewing tobacco), films, chewables, tabs, shaped parts, gels, consumable units, insoluble matrices, hollow shapes, reconstituted tobacco, expanded tobacco, and the like. See, e.g., U.S. Patent Publication No. 2006/0191548.

As used herein, "cigarette" refers a tobacco product having a "rod" and "filler". The cigarette "rod" includes the cigarette paper, filter, plug wrap (used to contain filtration materials), tipping paper that holds the cigarette paper (including the filler) to the filter, and all glues that hold these components together. The "filler" includes (1) all tobaccos, including but not limited to reconstituted and expanded tobacco, (2) non-tobacco substitutes (including but not limited to herbs, non-tobacco plant materials and other spices that may accompany tobaccos rolled within the cigarette paper), (3) casings, (4) flavorings, and (5) all other additives (that are mixed into tobaccos and substitutes and rolled into the cigarette).

As used herein, "reconstituted tobacco" refers to a part of tobacco filler made from tobacco dust and other tobacco scrap material, processed into sheet form and cut into strips to resemble tobacco. In addition to the cost savings, reconstituted tobacco is very important for its contribution to cigarette taste from processing flavor development using reactions between ammonia and sugars.

As used herein, "expanded tobacco" refers to a part of tobacco filler which is processed through expansion of suitable gases so that the tobacco is "puffed" resulting in reduced density and greater filling capacity. It reduces the weight of tobacco used in cigarettes.

Tobacco products derived from plants of the present disclosure also include cigarettes and other smoking articles, particularly those smoking articles including filter elements, where the rod of smokable material includes cured tobacco within a tobacco blend. In an aspect, a tobacco product of the present disclosure is selected from the group consisting of a cigarillo, a non-ventilated recess filter cigarette, a vented recess filter cigarette, a cigar, snuff, pipe tobacco, cigar tobacco, cigarette tobacco, chewing tobacco, leaf tobacco, hookah tobacco, shredded tobacco, and cut tobacco. In another aspect, a tobacco product of the present disclosure is a smokeless tobacco product. Smokeless tobacco products are not combusted and include, but not limited to, chewing tobacco, moist smokeless tobacco, snus, and dry snuff. Chewing tobacco is coarsely divided tobacco leaf that is typically packaged in a large pouch-like package and used in a plug or twist. Moist smokeless tobacco is a moist, more finely divided tobacco that is provided in loose form or in pouch form and is typically packaged in round cans and used as a pinch or in a pouch placed between an adult tobacco consumer's cheek and gum. Snus is a heat treated smokeless tobacco. Dry snuff is finely ground tobacco that is placed in the mouth or used nasally. In a further aspect, a tobacco product of the present disclosure is selected from the group consisting of loose leaf chewing tobacco, plug chewing tobacco, moist snuff, and nasal snuff. In yet another aspect, a tobacco product of the present disclosure is selected from the group consisting of an electronically heated cigarette, an e-cigarette, an electronic vaporing device.

In an aspect, a tobacco product of the present disclosure can be a blended tobacco product. In one aspect, a blended tobacco product comprises cured tobacco materials. In an aspect, a cured tobacco material constitutes about at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% of cured tobacco in a tobacco blend by weight. In one aspect, a cured tobacco material constitutes about at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% of cured tobacco in a tobacco blend by volume.

In an aspect, a tobacco product of the present disclosure can be a low nicotine tobacco product. In a further aspect, a tobacco product of the present disclosure may comprise nomicotine at a level of less than about 3 mg/g. For example, the nornicotine content in such a product can be about 3.0 mg/g, 2.5 mg/g, 2.0 mg/g, 1.5 mg/g, 1.0 mg/g, 750 µg/g, 500 pg/g, 250 pg/g, 100 pg/g, 75 pg/g, 50 pg/g, 25 pg/g, 10 pg/g, 7.0 pg/g, 5.0 pg/g, 4.0 pg/g, 2.0 pg/g, 1.0 pg/g, 0.5 pg/g, 0.4 pg/g, 0.2 pg/g, 0.1 pg/g, 0.05 pg/g, 0.01 pg/g, or undetectable.

In an aspect, cured tobacco material or tobacco products provided comprise an average nicotine or total alkaloid level selected from the group consisting of about 0.01%, 0.02%, 0.05%, 0.75%, 0.1%, 0.15%, 0.2%, 0.3%, 0.35%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2%, 2.1%, 2.2%, 2.3%, 2.4%, 2.5%, 2.6%, 2.7%, 2.8%, 2.9%, 3%, 3.1%, 3.2%, 3.3%, 3.4%, 3.5%, 3.6%, 3.7%, 3.8%, 3.9%, 4%, 5%, 6%, 7%, 8%, and 9% on a dry weight basis. In another aspect, cured tobacco material or tobacco products provided comprise an average nicotine or total alkaloid level selected from the group consisting of about between 0.01% and 0.02%, between 0.02% and 0.05%, between 0.05% and 0.75%, between 0.75% and 0.1%, between 0.1% and 0.15%, between 0.15% and 0.2%, between 0.2% and 0.3%, between 0.3% and 0.35%, between 0.35% and 0.4%, between 0.4% and 0.5%, between 0.5% and 0.6%, between 0.6% and 0.7%, between 0.7% and 0.8%, between 0.8% and 0.9%, between 0.9% and 1%, between 1% and 1.1%, between 1.1% and 1.2%, between 1.2% and 1.3%, between 1.3% and 1.4%, between 1.4% and 1.5%, between 1.5% and 1.6%, between 1.6% and 1.7%, between 1.7% and 1.8%, between 1.8% and 1.9%, between 1.9% and 2%, between 2% and 2.1%, between 2.1% and 2.2%, between 2.2% and 2.3%, between 2.3% and 2.4%, between 2.4% and 2.5%, between 2.5% and 2.6%, between 2.6% and 2.7%, between 2.7% and 2.8%, between 2.8% and 2.9%, between 2.9% and 3%, between 3% and 3.1%, between 3.1% and 3.2%, between 3.2% and 3.3%, between 3.3% and 3.4%, between 3.4% and 3.5%, and between 3.5% and 3.6% on a dry weight basis. In a further aspect, cured tobacco material or tobacco products provided comprise an average nicotine or total alkaloid level selected from the group consisting of about between 0.01% and 0.1%, between 0.02% and 0.2%, between 0.03% and 0.3%, between 0.04% and 0.4%, between 0.05% and 0.5%, between 0.75% and 1%, between 0.1% and 1.5%, between 0.15% and 2%, between 0.2% and 3%, and between 0.3% and 3.5% on a dry weight basis.

The present disclosure further provides a method manufacturing a tobacco product comprising tobacco material from tobacco plants disclosed. In an aspect, methods comprise conditioning aged tobacco material made from tobacco plants to increase its moisture content from between about 12.5% and about 13.5% to about 21%, blending the conditioned tobacco material to produce a desirable blend. In an aspect, the method of manufacturing a tobacco product further comprises casing or flavoring the blend. Generally, during the casing process, casing or sauce materials are added to blends to enhance their quality by balancing the chemical composition and to develop certain desired flavor characteristics. Further details for the casing process can be found in *Tobacco Production, Chemistry and Technology*, Edited by L. Davis and M. Nielsen, Blackwell Science, 1999.

Tobacco material provided can be also processed using methods including, but not limited to, heat treatment (e.g., cooking, toasting), flavoring, enzyme treatment, expansion and/or curing. Both fermented and non-fermented tobaccos can be processed using these techniques. Examples of suitable processed tobaccos include dark air-cured, dark fire cured, burley, flue cured, and cigar filler or wrapper, as well as the products from the whole leaf stemming operation. In an aspect, tobacco fibers include up to 70% dark tobacco on a fresh weight basis. For example, tobacco can be conditioned by heating, sweating and/or pasteurizing steps as described in U.S. Publication Nos. 2004/0118422 or 2005/0178398.

Tobacco material provided can be subject to fermentation. Fermenting typically is characterized by high initial moisture content, heat generation, and a 10 to 20% loss of dry weight. See, e.g., U.S. Pat. Nos. 4,528,993; 4,660,577; 4,848,373; and 5,372,149. In addition to modifying the aroma of the leaf, fermentation can change either or both the color and texture of a leaf. Also during the fermentation process, evolution gases can be produced, oxygen can be taken up, the pH can change, and the amount of water retained can change. See, for example, U.S. Publication No. 2005/0178398 and Tso (1999, Chapter 1 in Tobacco, Production, Chemistry and Technology, Davis & Nielsen, eds., Blackwell Publishing, Oxford). Cured, or cured and fermented tobacco can be further processed (e.g., cut, expanded, blended, milled or comminuted) prior to incorporation into the oral product. The tobacco, in some cases, is long cut fermented cured moist tobacco having an oven volatiles content of between 48 and 50 weight percent prior to mixing with the copolymer and optionally flavorants and other additives.

In an aspect, tobacco material provided can be processed to a desired size. In an aspect, tobacco fibers can be processed to have an average fiber size of less than 200 micrometers. In an aspect, tobacco fibers are between 75 and 125 micrometers. In another aspect, tobacco fibers are processed to have a size of 75 micrometers or less. In an aspect, tobacco fibers include long cut tobacco, which can be cut or shredded into widths of about 10 cuts/inch up to about 110 cuts/inch and lengths of about 0.1 inches up to about 1 inch. Double cut tobacco fibers can have a range of particle sizes such that about 70% of the double cut tobacco fibers falls between the mesh sizes of −20 mesh and 80 mesh.

Tobacco material provided can be processed to have a total oven volatiles content of about 10% by weight or greater; about 20% by weight or greater; about 40% by weight or greater; about 15% by weight to about 25% by weight; about 20% by weight to about 30% by weight; about 30% by weight to about 50% by weight; about 45% by weight to about 65% by weight; or about 50% by weight to about 60% by weight. Those of skill in the art will appreciate that "moist" tobacco typically refers to tobacco that has an oven volatiles content of between about 40% by weight and about 60% by weight (e.g., about 45% by weight to about 55% by weight, or about 50% by weight). As used herein, "oven volatiles" are determined by calculating the percentage of weight loss for a sample after drying the sample in a pre-warmed forced draft oven at 110° C. for 3.25 hours. The oral product can have a different overall oven volatiles content than the oven volatiles content of the tobacco fibers used to make the oral product. The processing steps described can reduce or increase the oven volatiles content.

Breeding

The present disclosure also provides methods for breeding tobacco lines, cultivars, or varieties comprising a desirable level of total alkaloid or nicotine, e.g., low nicotine or nicotine free, and desired leaf quality or grade level. Breeding can be carried out via any known procedures. DNA fingerprinting, SNP mapping, haplotype mapping or similar technologies may be used in a marker-assisted selection (MAS) breeding program to transfer or breed a desirable trait or allele into a tobacco plant. For example, a breeder can create segregating populations in a F2 or backcross generation using F1 hybrid plants or further crossing the F1 hybrid plants with other donor plants with an agronomically desirable genotype. Plants in the F2 or backcross generations can be screened for a desired agronomic trait or a desirable chemical profile using one of the techniques known in the art or listed herein. Depending on the expected inheritance pattern or the MAS technology used, self-pollination of selected plants before each cycle of backcrossing to aid identification of the desired individual plants can be performed. Backcrossing or other breeding procedure can be repeated until the desired phenotype of the recurrent parent is recovered. A recurrent parent in the present disclosure can be a flue-cured variety, a Burley variety, a dark air-cured variety, a dark fire-cured variety, or an Oriental variety. Other breeding techniques can be found, for example, in Wernsman, E. A., and Rufty, R. C. 1987. Chapter Seventeen. Tobacco. Pages 669-698 In: Cultivar Development. Crop Species. W. H. Fehr (ed.), MacMillan Publishing Go., Inc., New York, N.Y., incorporated herein by reference in their entirety.

Results of a plant breeding program using the tobacco plants described includes useful lines, cultivars, varieties, progeny, inbreds, and hybrids of the present disclosure. As used herein, the term "variety" refers to a population of plants that share constant characteristics which separate them from other plants of the same species. A variety is often, although not always, sold commercially. While possessing one or more distinctive traits, a variety is further characterized by a very small overall variation between individuals within that variety. A "pure line" variety may be created by several generations of self-pollination and selection, or vegetative propagation from a single parent using tissue or cell culture techniques. A variety can be essentially derived from another line or variety. As defined by the International Convention for the Protection of New Varieties of Plants (Dec. 2, 1961, as revised at Geneva on Nov. 10, 1972; on Oct. 23, 1978; and on Mar. 19, 1991), a variety is "essentially derived" from an initial variety if: a) it is predominantly derived from the initial variety, or from a variety that is predominantly derived from the initial variety, while retaining the expression of the essential characteristics that result from the genotype or combination of genotypes of the initial variety; b) it is clearly distinguishable from the initial variety; and c) except for the differences which result from the act of derivation, it conforms to the initial variety in the expression of the essential characteristics that result from the genotype or combination of genotypes of the initial variety. Essentially derived varieties can be obtained, for example, by the selection of a natural or induced mutant, a somaclonal variant, a variant individual from plants of the initial variety, backcrossing, or transformation. A first tobacco variety and a second tobacco variety from which the first variety is essentially derived, are considered as having essentially identical genetic background. A "line" as distinguished from a variety most often denotes a group of plants used non-commercially, for example in plant research. A line typically displays little overall variation between individuals for one or more traits of interest, although there may be some variation between individuals for other traits.

It is understood that any tobacco plant of the present disclosure can further comprise additional agronomically desirable traits, for example, by transformation with a genetic construct or transgene using a technique known in the art. Without limitation, an example of a desired trait is herbicide resistance, pest resistance, disease resistance; high yield; high grade index value; curability; curing quality; mechanical harvestability; holding ability; leaf quality; height, plant maturation (e.g., early maturing, early to medium maturing, medium maturing, medium to late maturing, or late maturing); stalk size (e.g., a small, medium, or a large stalk); or leaf number per plant (e.g., a small (e.g., 5-10 leaves), medium (e.g., 11-15 leaves), or large (e.g., 16-21) number of leaves), or any combination. In an aspect, low-nicotine or nicotine-free tobacco plants or seeds disclosed comprise one or more transgenes expressing one or more insecticidal proteins, such as, for example, a crystal protein of *Bacillus thuringiensis* or a vegetative insecticidal protein from *Bacillus cereus*, such as VIP3 (see, for example, Estruch et al. (1997) *Nat. Biotechnol.* 15:137). In another aspect, tobacco plants further comprise an introgressed trait conferring resistance to brown stem rot (U.S. Pat. No. 5,689,035) or resistance to cyst nematodes (U.S. Pat. No. 5,491,081).

The present disclosure also provides tobacco plants comprising an altered nicotine or total alkaloid level but having a yield comparable to the yield of corresponding initial tobacco plants without such a nicotine level alternation. In an aspect, a low-nicotine or nicotine-free tobacco variety provides a yield selected from the group consisting of about between 1200 and 3500, between 1300 and 3400, between 1400 and 3300, between 1500 and 3200, between 1600 and 3100, between 1700 and 3000, between 1800 and 2900, between 1900 and 2800, between 2000 and 2700, between 2100 and 2600, between 2200 and 2500, and between 2300 and 2400 lbs/acre. In another aspect, a low-nicotine or nicotine-free tobacco variety provides a yield selected from the group consisting of about between 1200 and 3500, between 1300 and 3500, between 1400 and 3500, between 1500 and 3500, between 1600 and 3500, between 1700 and 3500, between 1800 and 3500, between 1900 and 3500, between 2000 and 3500, between 2100 and 3500, between 2200 and 3500, between 2300 and 3500, between 2400 and 3500, between 2500 and 3500, between 2600 and 3500, between 2700 and 3500, between 2800 and 3500, between 2900 and 3500, between 3000 and 3500, and between 3100 and 3500 lbs/acre. In a further aspect, low-nicotine or nicotine-free tobacco plants provide a yield between 65% and 130%, between 70% and 130%, between 75% and 130%, between 80% and 130%, between 85% and 130%, between 90% and 130%, between 95% and 130%, between 100% and 130%, between 105% and 130%, between 110% and 130%, between 115% and 130%, or between 120% and 130% of the yield of a control plant having essentially identical genetic background except a genetic modification providing the low-nicotine or nicotine-free trait. In a further aspect, low-nicotine or nicotine-free tobacco plants provide a yield between 70% and 125%, between 75% and 120%, between 80% and 115%, between 85% and 110%, or between 90% and 100% of the yield of a control plant having essentially identical genetic background except a genetic modification providing the low-nicotine or nicotine-free trait.

In an aspect, a LQG mutant or transgenic tobacco plant in a low-alkaloid background exhibits one or more, two or more, three or more, or all of the traits selected from the group consisting of: increased yield as compared to the low-alkaloid background control, accelerated ripening and senescence as compared to the low-alkaloid background control, reduced susceptibility to insect herbivory as compared to the low-alkaloid background control, and reduced polyamine content after topping as compared to the low-alkaloid background control. In an aspect, a LQG mutant or transgenic tobacco plant in a low-alkaloid background exhibits one or more, two or more, three or more, or all of the traits selected from the group consisting of: increased yield as compared to LA BU21, accelerated ripening and senescence as compared to LA BU21, reduced susceptibility to insect herbivory as compared to LA BU21, and reduced polyamine content after topping as compared to LA BU21.

In an aspect, a LQG mutant or transgenic tobacco plant (e.g., a low-nicotine, nicotine-free, or low-alkaloid tobacco variety) does not exhibit one or more, two or more, three or more, or all of the LA BU21 traits selected from the group consisting of lower yield, delayed ripening and senescence of leaves, higher susceptibility to insect herbivory, increased polyamine content after topping, higher chlorophyll, more mesophyll cells per unit leaf area, and poor end-product quality after curing. In an aspect, a tobacco plant disclosed (e.g., a low-nicotine, nicotine-free, or low-alkaloid tobacco variety) does not exhibit two or more of the LA BU21 traits selected from the group consisting of lower yield, delayed ripening and senescence, higher susceptibility to insect herbivory, increased polyamine content after topping, higher chlorophyll, more mesophyll cells per unit leaf area, and poor end-product quality after curing. In an aspect, a tobacco plant disclosed (e.g., a low-nicotine, nicotine-free, or low-alkaloid tobacco variety) does not exhibit three or more of the LA BU21 traits selected from the group consisting of lower yield, delayed ripening and senescence, higher susceptibility to insect herbivory, increased polyamine content after topping, higher chlorophyll, more mesophyll cells per unit leaf area, and poor end-product quality after curing. In an aspect, a tobacco plant disclosed (e.g., a low-nicotine, nicotine-free, or low-alkaloid tobacco variety) exhibits at a lower level compared to LA BU21, LAFC53, or LN KY171, one or more, two or more, three or more, or all of the LA BU21 traits selected from the group consisting of lower yield, delayed ripening and senescence, higher susceptibility to insect herbivory, increased polyamine content after topping, higher chlorophyll, more mesophyll cells per unit leaf area, and poor end-product quality after curing. In an aspect, a tobacco plant disclosed (e.g., a low-nicotine, nicotine-free, or low-alkaloid tobacco variety) exhibits at a lower level compared to LA BU21, LAFC53, or LN KY171, two or more of the LA BU21 traits selected from the group consisting of lower yield, delayed ripening and senescence, higher susceptibility to insect herbivory, increased polyamine content after topping, higher chlorophyll, more mesophyll cells per unit leaf area, and poor end-product quality after curing. In an aspect, a tobacco plant disclosed (e.g., a low-nicotine, nicotine-free, or low-alkaloid tobacco variety) exhibits at a lower level compared to LA BU21, LAFC53, or LN KY171, three or more, or all of the LA BU21 traits selected from the group consisting of lower yield, delayed ripening and senescence, higher susceptibility to insect herbivory, increased polyamine content after topping, higher chlorophyll, more mesophyll cells per unit leaf area, and poor end-product quality after curing.

In an aspect, a modified tobacco plant (e.g., a low-nicotine, nicotine-free, or low-alkaloid tobacco variety) comprises a LQG genetic modification and a further genetic modification conferring a desired trait (e.g., low-nicotine, nicotine-free, or low-alkaloid) without substantially impacting a trait selected from the group consisting of yield, ripening and senescence, susceptibility to insect herbivory, polyamine content after topping, chlorophyll level, mesophyll cell number per unit leaf area, and end-product quality after curing.

In an aspect, a LQG mutant or transgenic tobacco plant comprises a modification conferring a desired trait (e.g., low-nicotine, nicotine-free, or low-alkaloid) and further comprises a trait substantially comparable to an unmodified control plant, where the trait is selected from the group consisting of yield, ripening and senescence, susceptibility to insect herbivory, polyamine content after topping, chlorophyll level, mesophyll cell number per unit leaf area, and end-product quality after curing.

In an aspect, tobacco plants provided are hybrid plants. Hybrids can be produced by preventing self-pollination of female parent plants (e.g., seed parents) of a first variety, permitting pollen from male parent plants of a second variety to fertilize the female parent plants, and allowing F1 hybrid seeds to form on the female plants. Self-pollination of female plants can be prevented by emasculating the flowers at an early stage of flower development. Alternatively, pollen formation can be prevented on the female parent plants using a form of male sterility. For example, male sterility can be produced by male sterility (MS), or transgenic male sterility where a transgene inhibits microsporogenesis and/or pollen formation, or self-incompatibility. Female parent plants containing MS are particularly useful. In aspects in which the female parent plants are MS, pollen may be harvested from male fertile plants and applied manually to the stigmas of MS female parent plants, and the resulting F1 seed is harvested.

Plants can be used to form single-cross tobacco F1 hybrids. Pollen from a male parent plant is manually transferred to an emasculated female parent plant or a female parent plant that is male sterile to form F1 seed. Alternatively, three-way crosses can be carried out where a single-cross F1 hybrid is used as a female parent and is crossed with a different male parent. As another alternative, double-cross hybrids can be created where the F1 progeny of two different single-crosses are themselves crossed. Self-incompatibility can be used to particular advantage to prevent self-pollination of female parents when forming a double-cross hybrid.

In an aspect, a low-nicotine or nicotine-free tobacco variety is male sterile. In another aspect, a low-nicotine or nicotine-free tobacco variety is cytoplasmic male sterile. Male sterile tobacco plants may be produced by any method known in the art. Methods of producing male sterile tobacco are described in Wernsman, E. A., and Rufty, R. C. 1987. Chapter Seventeen. Tobacco. Pages 669-698 In: Cultivar Development. Crop Species. W. H. Fehr (ed.), MacMillan Publishing Go., Inc., New York, N.Y. 761 pp.

In a further aspect, tobacco parts provided include, but are not limited to, a leaf, a stem, a root, a seed, a flower, pollen, an anther, an ovule, a pedicel, a fruit, a meristem, a cotyledon, a hypocotyl, a pod, an embryo, endosperm, an explant, a callus, a tissue culture, a shoot, a cell, and a protoplast. In an aspect, tobacco part provided does not include seed. In an aspect, this disclosure provides tobacco plant cells, tissues, and organs that are not reproductive material and do not mediate the natural reproduction of the plant. In another aspect, this disclosure also provides tobacco plant cells, tissues, and organs that are reproductive material and mediate the natural reproduction of the plant. In another aspect, this disclosure provides tobacco plant cells, tissues, and organs that cannot maintain themselves via photosynthesis. In another aspect, this disclosure provides somatic tobacco plant cells. Somatic cells, contrary to germline cells, do not mediate plant reproduction.

The provided cells, tissues and organs may be from seed, fruit, leaf, cotyledon, hypocotyl, meristem, embryos, endosperm, root, shoot, stem, pod, flower, infloresence, stalk, pedicel, style, stigma, receptacle, petal, sepal, pollen, anther, filament, ovary, ovule, pericarp, phloem, vascular tissue. In another aspect, this disclosure provides a tobacco plant chloroplast. In a further aspect, this disclosure provides epidermal cells, stomata cell, leaf or root hairs, a storage root, or a tuber. In another aspect, this disclosure provides a tobacco protoplast.

Skilled artisans understand that tobacco plants naturally reproduce via seeds, not via asexual reproduction or vegetative propagation. In an aspect, this disclosure provides tobacco endosperm. In another aspect, this disclosure provides tobacco endosperm cells. In a further aspect, this disclosure provides a male or female sterile tobacco plant, which cannot reproduce without human intervention. Skilled artisans further understand that cured tobacco does not constitute a living organism and is not capable of growth or reproduction.

Nucleic Acid/Polypeptide

In an aspect, the present disclosure provides a nucleic acid molecule comprising at least about 40%, 45%, 50%, 55%, 60%, 65%, 70%, 75%, 80%, 85%, 90%, 91%, 92%, 93%, 94%, 95%, 96%, 97%, 98%, 99%, or 100% identity to a sequence selected from the group consisting of SEQ ID NOs: 1 to 17, and fragments thereof. In an aspect, the present disclosure provides a polypeptide or protein comprising at least about 40%, 45%, 50%, 55%, 60%, 65%, 70%, 75%, 80%, 85%, 90%, 91%, 92%, 93%, 94%, 95%, 96%, 97%, 98%, 99%, or 100% identity or similarity to an amino acid sequence selected from the group consisting of SEQ ID NOs: 18 to 34. In another aspect, the present disclosure provides a biologically active variant of a protein having an amino acid sequence selected from the group consisting of SEQ ID NOs: 18 to 34. A biologically active variant of a protein of the present disclosure may differ from that protein by as few as 1-15 amino acid residues, as few as 10, as few as 9, as few as 8, as few as 7, as few as 6, as few as 5, as few as 4, as few as 3, as few as 2, or as few as 1 amino acid residue. Also provided are orthologous genes or proteins of genes or proteins comprising a sequence selected from the group consisting of SEQ ID NOs: 1 to 34. "Orthologs" are genes derived from a common ancestral gene and which are found in different species as a result of speciation. Orthologs may share at least 60%, 70%, 75%, 80%, 85%, 90%, 91%, 92%, 93%, 94%, 95%, 96%, 97%, 98%, 99%, or greater sequence identity or similarity at the nucleotide sequence and/or the protein sequence level. Functions of orthologs are often highly conserved among species.

As used herein, the term "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are deemed to have "sequence similarity" or "similarity."

Nucleic acid molecules, polypeptides, or proteins provided can be isolated or substantially purified. An "isolated" or "purified" nucleic acid molecule, polypeptide, protein, or biologically active portion thereof, is substantially or essentially free from components that normally accompany or interact with the polynucleotide or protein as found in its naturally occurring environment. For example, an isolated or purified polynucleotide or protein is substantially free of other cellular material, or culture medium when produced by recombinant techniques, or substantially free of chemical precursors or other chemicals when chemically synthesized.

The following exemplary, non-limiting, embodiments are envisioned:

1. A modified tobacco plant, or part thereof, comprising a genetic modification upregulating the expression or activity of a gene encoding a nucleic acid sequence having at least 70%, at least 80%, at least 90%, at least 95%, at least 97%, at least 99%, or 100% identity to a nucleic acid sequence selected from the group consisting of SEQ ID NOs: 1-15.
2. A modified tobacco plant, or part thereof, comprising a recombinant nucleic acid construct comprising a heterologous promoter operably linked to a polynucleotide having at least 70%, at least 80%, at least 90%, at least 95%, at least 97%, at least 99%, or 100% identity to a nucleic acid sequence selected from the group consisting of SEQ ID NOs: 1-15.
3. A modified tobacco plant, or part thereof, comprising a genetic modification upregulating the expression or activity of a gene encoding a polypeptide having at least 70%, at least 80%, at least 90%, at least 95%, at least 97%, at least 99%, or 100% identity or similarity to an amino acid sequence selected from the group consisting of SEQ ID NOs: 18-32.
4. A modified tobacco plant, or part thereof, comprising a recombinant nucleic acid construct comprising a heterologous promoter operably linked to a polynucleotide encoding a polypeptide having at least 70%, at least 80%, at least 90%, at least 95%, at least 97%, at least 99%, or 100% identity or similarity to an amino acid sequence selected from the group consisting of SEQ ID NOs: 18-32.
5. A modified tobacco plant, or part thereof, comprising a genetic modification downregulating the expression or activity of a gene encoding a nucleic acid sequence having at least 70%, at least 80%, at least 90%, at least 95%, at least 97%, at least 99%, or 100% identity to a nucleic acid sequence selected from the group consisting of SEQ ID NOs: 16-17.
6. A modified tobacco plant, or part thereof, comprising a non-natural mutation in a polynucleotide having at least 70%, at least 80%, at least 90%, at least 95%, at least 97%, at least 99%, or 100% identity to a nucleic acid sequence selected from the group consisting of SEQ ID NOs: 16-17.
7. A modified tobacco plant, or part thereof, comprising a recombinant nucleic acid construct comprising a heterologous promoter operably linked to a polynucleotide that encodes a non-coding RNA molecule, where said non-coding RNA molecule is capable of binding to an mRNA having at least 70%, at least 80%, at least 90%, at least 95%, at least 97%, at least 99%, or 100% identity to a nucleic acid sequence selected from the group consisting of SEQ ID NOs: 16-17, wherein said non-coding RNA molecule suppresses the level or translation of said mRNA.
8. A modified tobacco plant, or part thereof, comprising a genetic modification downregulating the expression or activity of a gene encoding a polypeptide having at least 70%, at least 80%, at least 90%, at least 95%, at least 97%, at least 99%, or 100% identity or similarity to an amino acid sequence selected from the group consisting of SEQ ID NOs: 33-34.
9. A modified tobacco plant, or part thereof, comprising a non-natural mutation in a polynucleotide having a nucleic acid sequence encoding a polypeptide having at least 70%, at least 80%, at least 90%, at least 95%, at least 97%, at least 99%, or 100% identity or similarity to an amino acid sequence selected from the group consisting of SEQ ID NOs: 33-34.
10. A modified tobacco plant, or part thereof, comprising a recombinant nucleic acid construct comprising a heterologous promoter operably linked to a polynucleotide that encodes a non-coding RNA molecule, where said non-coding RNA molecule is capable of binding to an RNA encoding a polypeptide having at least 70%, at least 80%, at least 90%, at least 95%, at least 97%, at least 99%, or 100% identity or similarity to an amino acid sequence selected from the group consisting of SEQ ID NOs: 33-34, wherein said non-coding RNA molecule suppresses the expression of said polypeptide.
11. The modified tobacco plant, or part thereof, of any one of embodiments 1 to 10, wherein said tobacco plant is a *Nicotiana tabacum* plant.
12. The modified tobacco plant, or part thereof, of embodiment 11, wherein said tobacco plant comprises a mutation or transgene conferring a reduced level of nicotine relative to a control plant not having said mutation or transgene.
13. The modified tobacco plant, or part thereof, of embodiment 12, wherein said tobacco plant is a low-alkaloid tobacco plant.
14. The modified tobacco plant, or part thereof, of embodiment 12, wherein said tobacco plant produces a leaf, when cured, having a higher USDA grade index value than that of a comparable leaf of a control plant when grown and cured in similar conditions, wherein said control plant shares an essentially identical genetic background with the tobacco plant except said genetic modification, said recombinant nucleic acid construct or said non-natural mutation.
15. The modified tobacco plant, or part thereof, of embodiment 14, wherein said higher USDA grade index value is at least 200%, 150%, 100%, 90%, 80%, 70%, 60%, 50%, 40%, 30%, 20%, 17.5%, 15%, 12.5%, 10%, 7.5%, or 5% higher than that of said comparable leaf of a control plant.

16. The modified tobacco plant, or part thereof, of embodiment 12, wherein said mutation conferring a reduced level of nicotine comprises a nic1 mutation, a nic2 mutation, or both.
17. The modified tobacco plant, or part thereof, of embodiment 16, wherein said nic1 mutation, said nic2 mutation, or both are introgressed or derived from a variety selected from the group consisting of LA Burley 21, LAFC53, LN B&W, and LN KY171.
18. The modified tobacco plant, or part thereof, of embodiment 12, wherein said mutation conferring a reduced level of nicotine comprises a mutation in a gene or locus encoding a protein selected from the group consisting of aspartate oxidase, agmatine deiminase (AIC), arginase, diamine oxidase, arginine decarboxylase (ADC), methylputrescine oxidase (MPO), NADH dehydrogenase, ornithine decarboxylase (ODC), phosphoribosylanthranilate isomerase (PRAI), putrescine N-methyltransferase (PMT), quinolate phosphoribosyl transferase (QPT), S-adenosyl-methionine synthetase (SAMS), A622, NBB1, BBL, MYC2, Nic1_ERF, Nic2_ERF, ethylene response factor (ERF) transcription factor, nicotine uptake permease (NUP), and MATE transporter.
19. The modified tobacco plant, or part thereof, of embodiment 12, wherein said mutation conferring a reduced level of nicotine comprises a mutation in a gene or locus encoding a protein selected from the group consisting of ERF101, ERF110, ERFnew, ERF199, ERF19, ERF130, ERF16, ERF29, ERF210, and ERF91L2.
20. The modified tobacco plant, or part thereof, of embodiment 12, wherein said mutation conferring a reduced level of nicotine comprises a mutation in a gene or locus encoding a protein selected from the group consisting of ERF32, ERF34, ERF39, ERF189, ERF 115, ERF221, ERF104, ERF179, ERF17, and ERF168.
21. The modified tobacco plant, or part thereof, of embodiment 12, wherein said transgene conferring a reduced level of nicotine comprises a transgene targeting and suppressing a gene encoding a protein selected from the group consisting of aspartate oxidase, agmatine deiminase (AIC), arginase, diamine oxidase, arginine decarboxylase (ADC), methylputrescine oxidase (MPO), NADH dehydrogenase, ornithine decarboxylase (ODC), phosphoribosylanthranilate isomerase (PRAI), putrescine N-methyltransferase (PMT), quinolate phosphoribosyl transferase (QPT), S-adenosyl-methionine synthetase (SAMS), A622, NBB1, BBL, MYC2, Nic1_ERF, Nic2_ERF, ethylene response factor (ERF) transcription factor, nicotine uptake permease (NUP), and MATE transporter.
22. The modified tobacco plant, or part thereof, of embodiment 12, wherein said transgene conferring a reduced level of nicotine comprises a transgene targeting and suppressing a gene encoding a protein selected from the group consisting of ERF101, ERF110, ERFnew, ERF199, ERF19, ERF130, ERF16, ERF29, ERF210, and ERF91L2.
23. The modified tobacco plant, or part thereof, of embodiment 12, wherein said transgene conferring a reduced level of nicotine comprises a transgene targeting and suppressing a gene encoding a protein selected from the group consisting of ERF32, ERF34, ERF39, ERF189, ERF115, ERF221, ERF104, ERF179, ERF17, and ERF168.
24. The modified tobacco plant, or part thereof, of any one of embodiments 21 to 23, wherein said transgene encodes a non-coding RNA selected from the group consisting of microRNA (miRNA), anti-sense RNA, small interfering RNA (siRNA), a trans-acting siRNA (ta-siRNA), and hairpin RNA (hpRNA).
25. The modified tobacco plant, or part thereof, of any one of embodiments 12 to 24, wherein said tobacco plant is capable of producing a leaf comprising a comparable level of one or more polyamines relative to a comparable leaf of a control plant not comprising said mutation or transgene conferring a reduced level of nicotine.
26. The modified tobacco plant, or part thereof, of embodiment 25, wherein said comparable level is within 20%, 17.5%, 15%, 12.5%, 10%, 7.5%, 5%, 2.5%, or 1% of the level in said comparable leaf of a control plant.
27. The modified tobacco plant, or part thereof, of any one of embodiments 12 to 24, wherein said tobacco plant is capable of producing a leaf comprising a comparable chlorophyll level relative to a comparable leaf of a control plant not comprising said mutation or transgene conferring a reduced level of nicotine.
28. The modified tobacco plant, or part thereof, of embodiment 27, wherein said comparable chlorophyll level is within 20%, 17.5%, 15%, 12.5%, 10%, 7.5%, 5%, 2.5%, or 1% of the level in said comparable leaf of a control plant.
29. The modified tobacco plant, or part thereof, of any one of embodiments 12 to 24, wherein said tobacco plant is capable of producing a leaf comprising a comparable number of mesophyll cells per unit of leaf area relative to a comparable leaf of a control plant not comprising said mutation or transgene conferring a reduced level of nicotine.
30. The modified tobacco plant, or part thereof, of embodiment 29, wherein said comparable mesophyll cells per unit of leaf area is within 20%, 17.5%, 15%, 12.5%, 10%, 7.5%, 5%, 2.5%, or 1% of the mesophyll cells per unit of leaf area in said comparable leaf of a control plant.
31. The modified tobacco plant, or part thereof, of any one of embodiments 12 to 24, wherein said tobacco plant is capable of producing a leaf comprising a comparable epidermal cell size relative to a comparable leaf of a control plant not comprising said mutation or transgene conferring a reduced level of nicotine.
32. The modified tobacco plant, or part thereof, of embodiment 31, wherein said comparable epidermal cell size is within 20%, 17.5%, 15%, 12.5%, 10%, 7.5%, 5%, 2.5%, or 1% of the epidermal cell size in said comparable leaf of a control plant.
33. The modified tobacco plant, or part thereof, of any one of embodiments 12 to 24, wherein said tobacco plant comprises a comparable leaf yield relative to a comparable leaf of a control plant not comprising said mutation or transgene conferring a reduced level of nicotine.
34. The modified tobacco plant, or part thereof, of embodiment 33, wherein said comparable leaf yield is within 20%, 17.5%, 15%, 12.5%, 10%, 7.5%, 5%, 2.5%, or 1% of the leaf yield in said comparable leaf of a control plant.
35. The modified tobacco plant, or part thereof, of any one of embodiments 12 to 24, wherein said tobacco plant exhibits a comparable insect herbivory susceptibility relative to a comparable leaf of a control plant not comprising said mutation or transgene conferring a reduced level of nicotine.
36. The modified tobacco plant, or part thereof, of any one of embodiments 5 and 8, wherein said genetic modification comprises or encodes a non-coding RNA.
37. The modified tobacco plant, or part thereof, of embodiment 36, wherein said non-coding RNA is selected from the group consisting of microRNA (miRNA), anti-sense RNA, small interfering RNA (siRNA), a trans-acting siRNA (ta-siRNA), and hairpin RNA (hpRNA).
38. The modified tobacco plant, or part thereof, of any one of embodiments 1 to 5, 7, 8, 10, and to 11, wherein said genetic modification or heterologous promoter comprises an inducible promoter.
39. The modified tobacco plant, or part thereof, of any one of embodiments 1 to 5, 7, 8, 10, and 11, wherein said genetic modification or heterologous promoter comprises a tissue-specific or tissue-preferred promoter.
40. The modified tobacco plant, or part thereof, of any one of embodiments 1 to 5, 7, 8, 10, and 11, wherein said genetic modification or heterologous promoter comprises a constitutive promoter.
41. The modified tobacco plant, or part thereof, of embodiment 38, wherein said inducible promoter is a topping-inducible promoter.
42. The modified tobacco plant, or part thereof, of embodiment 38, wherein said inducible promoter is also a tissue-specific or tissue-preferred promoter.
43. The modified tobacco plant, or part thereof, of embodiment 39 or 42, wherein said tissue-specific or tissue-preferred promoter is specific or preferred for one or more tissues or organs selected from the group consisting of shoot, root, leaf, stem, flower, sucker, root tip, mesophyll cells, epidermal cells, and vasculature.
44. The modified tobacco plant, or part thereof, of embodiment 38, wherein said inducible promoter regulates root specific or preferred expression.
45. The modified tobacco plant, or part thereof, of embodiment 38, wherein said inducible promoter regulates leaf specific or preferred expression.
46. The modified tobacco plant, or part thereof, of any one of embodiments 1, 3, 5, 8, and 11, wherein said genetic modification comprises a non-natural mutation in a genomic sequence of said gene being upregulated or downregulated.
47. The modified tobacco plant, or part thereof, of embodiment 46, wherein said mutation is in a promoter region or a protein-coding region.
48. The tobacco plant, or part thereof, of any one of embodiments 12 to 47, wherein said tobacco plant is capable of producing a leaf, when cured, having a USDA grade index value of 70 or more.
49. The tobacco plant, or part thereof, of any one of embodiments 12 to 47, wherein said tobacco plant is capable of producing a leaf, when cured, having a USDA grade index value comparable to that of a control plant when grown and cured in similar conditions, wherein said control plant shares an essentially identical genetic background with said tobacco plant except said mutation or transgene conferring a reduced level of nicotine.
50. The tobacco plant, or part thereof, of any one of embodiments 12 to 47, wherein said tobacco plant is capable of producing a leaf with a leaf grade comparable to that of a leaf from a control plant without said mutation or transgene conferring a reduced level of nicotine.
51. The tobacco plant, or part thereof, of any one of embodiments 12 to 50, wherein said tobacco plant has a total leaf yield comparable to a control plant without said mutation or transgene conferring a reduced level of nicotine.
52. The tobacco plant, or part thereof, of any one of the preceding claims, wherein said tobacco plant comprises a nicotine level selected from the group consisting of less than 3%, less than 2.75%, less than 2.5%, less than 2.25%, less than 2.0%, less than 1.75%, less than 1.5%, less than 1.25%, less than 1%, less than 0.9%, less than 0.8%, less than 0.7%, less than 0.6%, less than 0.5%, less than 0.4%, less than 0.3%, less than 0.2%, less than 0.1%, and less than 0.05%.
53. The tobacco plant, or part thereof, of any one of embodiments 12 to 52, wherein said tobacco plant comprises nicotine at a level below 1%, below 2%, below 5%, below 8%, below 10%, below 12%, below 15%, below 20%, below 25%, below 30%, below 40%, below 50%, below 60%, below 70%, or below 80% of the nicotine level of a control plant without said mutation or transgene conferring a reduced level of nicotine, when grown in comparable growth conditions.
54. A population of the tobacco plants of any one of embodiments 1 to 53.
55. Cured tobacco material from the tobacco plant of any one of embodiments 1 to 53.
56. The cured tobacco material of embodiment 55, wherein said cured tobacco material is made by a curing process selected from the group consisting of flue curing, air curing, fire curing, and sun curing.
57. A reconstituted tobacco comprising the cured tobacco material of embodiment 55.
58. A tobacco blend comprising said cured tobacco material of embodiment 55.
59. The tobacco blend of embodiment 58, wherein said cured tobacco material constitutes about at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% of cured tobacco in said tobacco blend by weight.
60. The tobacco blend of embodiment 58, wherein said cured tobacco material constitutes about at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% of cured tobacco in said tobacco blend by volume.
61. A tobacco product comprising the cured tobacco material of embodiment 55.
62. The tobacco product of embodiment 61, wherein said tobacco product is a smokeless tobacco product.
63. The tobacco product of embodiment 61, wherein said tobacco product is selected from the group consisting of a cigarette, a cigarillo, a non-ventilated recess filter cigarette, a vented recess filter cigarette, a cigar, snuff, pipe tobacco, cigar tobacco, cigarette tobacco, chewing tobacco, leaf tobacco, shredded tobacco, and cut tobacco.
64. The tobacco product of embodiment 61, wherein said tobacco product is selected from the group consisting of reconstituted tobacco, loose leaf chewing tobacco, plug chewing tobacco, moist snuff, snus, and nasal snuff.

65. A method for improving leaf quality in a reduced-alkaloid tobacco plant, said method comprising:
   (a) growing a reduced-alkaloid tobacco plant;
   (b) upregulating the expression or activity of a gene encoding
      (i) a nucleic acid sequence having at least 70%, at least 80%, at least 90%, at least 95%, at least 97%, at least 99%, or 100% identity to a sequence selected from the group consisting of SEQ ID NOs: 1-15, or
      (ii) a polypeptide sequence having at least 70%, at least 80%, at least 90%, at least 95%, at least 97%, at least 99%, or 100% identity or similarity to a sequence selected from the group consisting of SEQ ID NOs: 18-32; and
   (c) harvesting leaves or seeds from said tobacco plant.

66. A method for improving leaf quality in a reduced-alkaloid tobacco plant, said method comprising:
   (a) growing a reduced-alkaloid tobacco plant;
   (b) downregulating the expression or activity of a gene encoding
      (i) a nucleic acid sequence having at least 70%, at least 80%, at least 90%, at least 95%, at least 97%, at least 99%, or 100% identity to a sequence selected from the group consisting of SEQ ID NOs: 16-17, or
      (ii) a polypeptide sequence having at least 70%, at least 80%, at least 90%, at least 95%, at least 97%, at least 99%, or 100% identity or similarity to a sequence selected from the group consisting of SEQ ID NOs: 33-34; and
      (iii) harvesting leaves or seeds from said tobacco plant.

Having now generally described the disclosure, the same will be more readily understood through reference to the following examples that are provided by way of illustration, and are not intended to be limiting of the present disclosure, unless specified.

EXAMPLES

Example 1: Leaf Sampling from Tobacco Lines with Various Reduced-Nicotine Levels Tobacco plants with varying degrees of reduced nicotine levels are obtained, by suppressing various nicotine biosynthetic genes or by mutating regulatory loci (Table 8). Seven burley tobacco lines (BU21, HI BU21, LI BU21, LA BU21, TN90 LC, TN90 PMT-RNAi, and TN90 PR50-RNAi) and 4 flue-cured tobacco lines (K326, K326 PMT-RNAi, LAFC53, and Brown & Williams Low Nicotine ("LN B&W")) are grown in the field. Table 8 provides the genotype and background of these eleven lines.

Originating from low-alkaloid Cuban cigar varieties, mutations in two loci, Nic1 and Nic2, provide sources for low alkaloid breeding. LA BU21 (Low Alkaloid Burley 21 harboring both nic1 and nic2 mutations) exhibits 90-97% alkaloid reduction compared to BU21 control plants. HI BU21 (High-Intermediate Burley 21 harboring a nic2 mutation) exhibits 20-30% alkaloid reduction compared to BU21 control plants. LI BU21 (Low-Intermediate Burley 21 harboring a nic1 mutation) exhibits 65-75% alkaloid reduction compared to BU21 control plants. PMT and PR50 are both involved in nicotine biosynthesis. PR50 RNAi and PMT RNAi lines exhibit 80% and ~95% nicotine reduction, respectively, relative to control plants (FIGS. 1A and 1B).

Figure 1B:
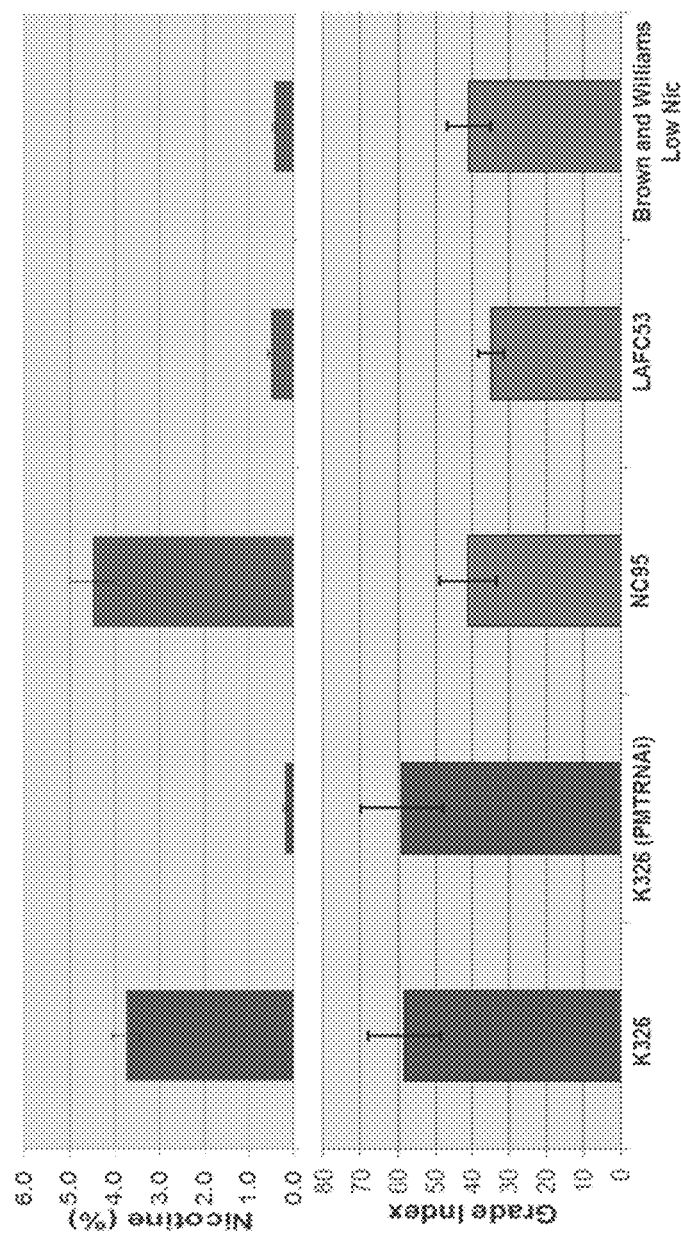
FIG. 1B depicts nicotine levels and leaf grade index of various flue-cured varieties.
Figure 1C:
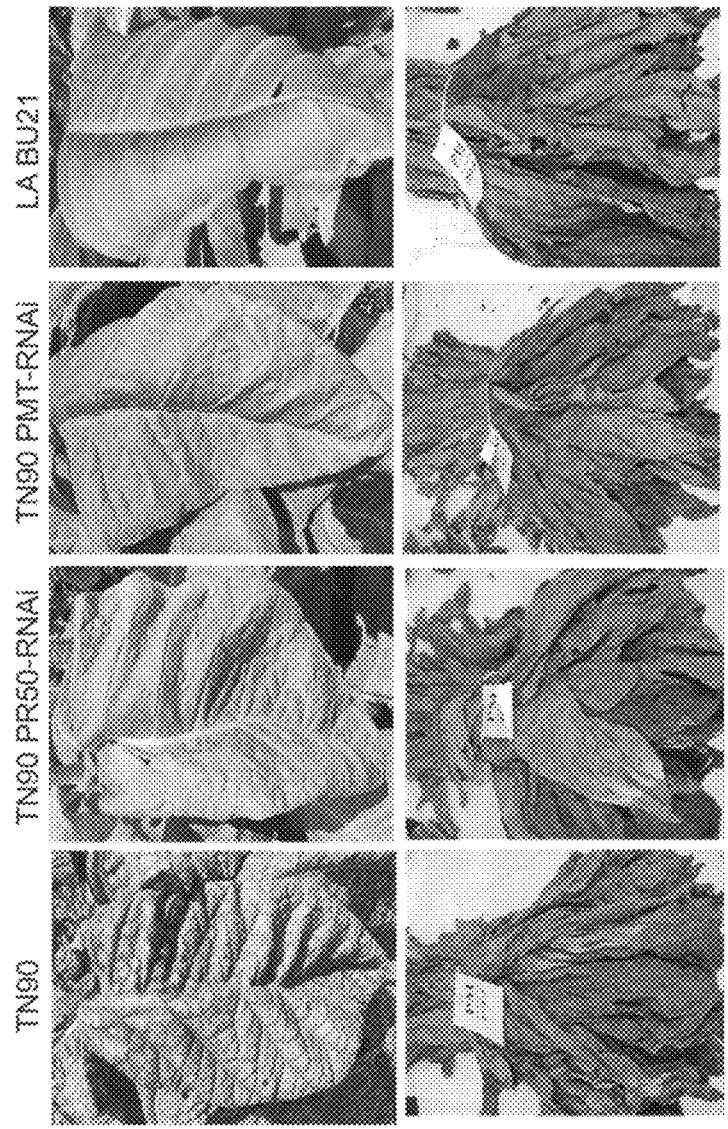
FIG. 1C depicts leaf quality of various burley varieties.
Figure 1D:
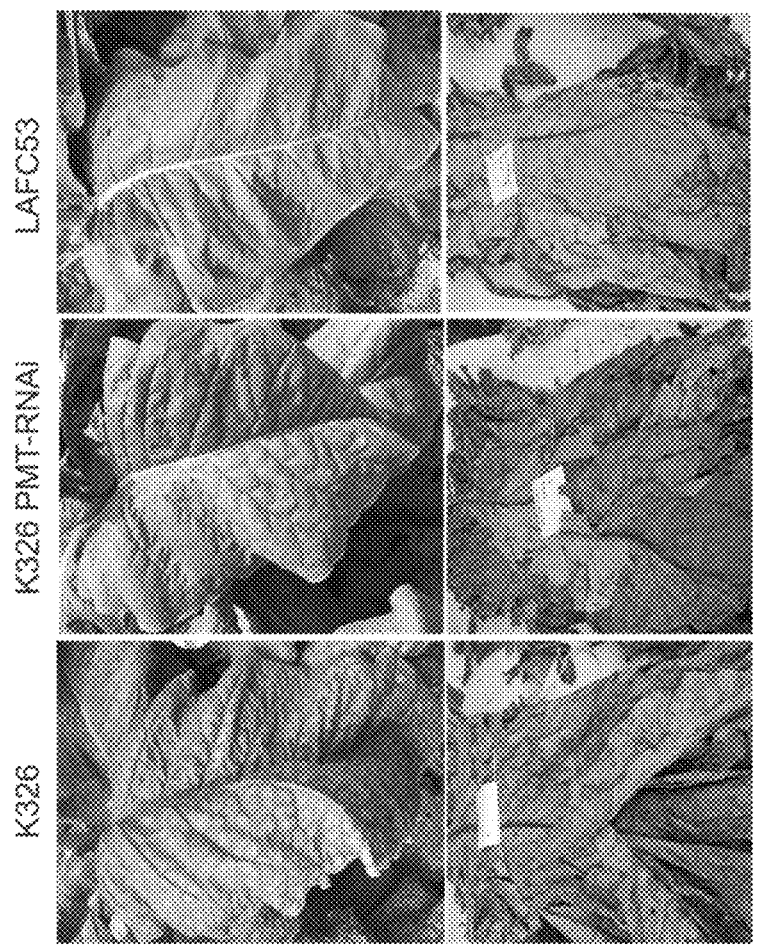
FIG. 1D depicts leaf quality of various flue-cured varieties.
Figure 2:
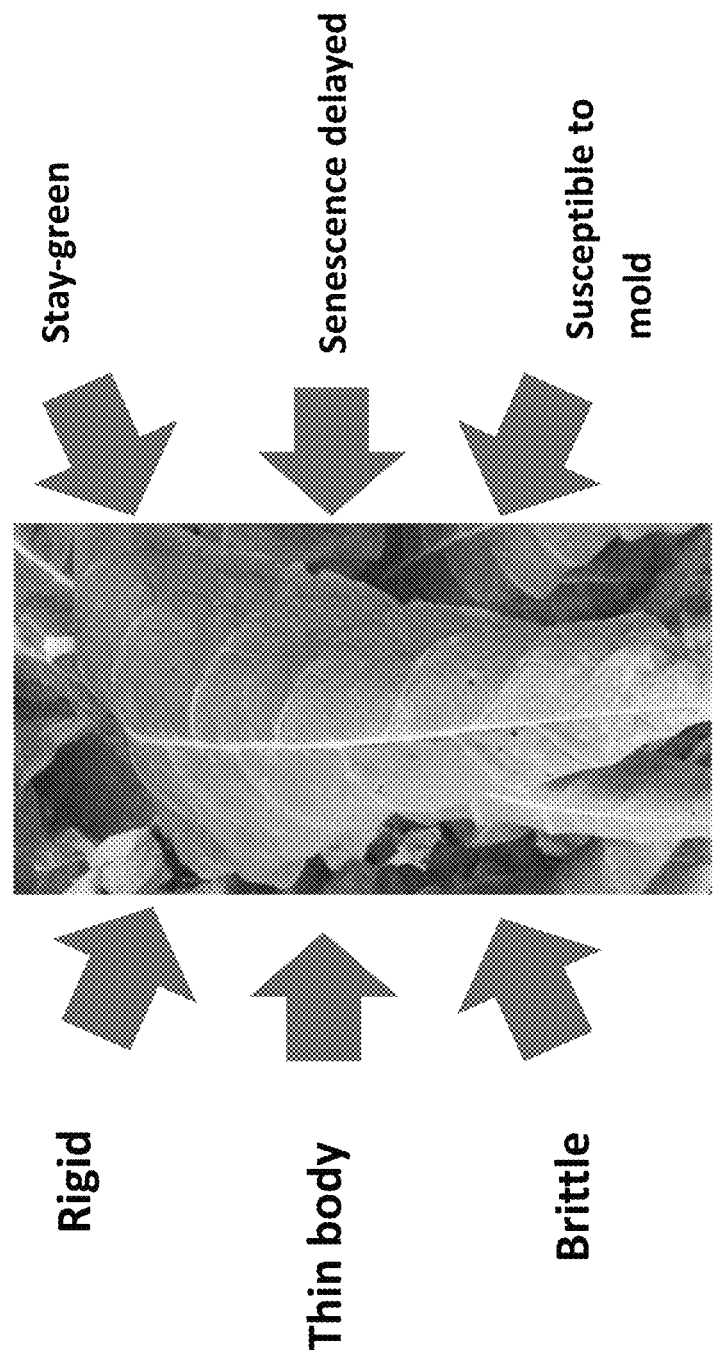
FIG. 2 depicts some leaf phenotype of a low-alkaloid tobacco line harboring nic1 and nic2 mutations.

These low-alkaloid lines exhibit different leaf quality (FIGS. 1A to 1D). In general, low-alkaloid lines, especially those harboring nic1 and nic2 double mutations, cause an unfavorable leaf phenotype characterized by, for example, lower yields, delayed ripening and senescence, higher susceptibility to insect herbivory, and poor end-product quality after curing (FIG. 2). For example, LA BU21 shows poor-quality tight-leaf structure compared to TN90-RNAi and PR50-RNAi burley lines. In comparison, PMT-RNAi and PR50-RNAi burley lines show improved leaf grade index relative to LA BU21 (FIGS. 1A and 1C). Similar to LA BU21, leaves from flue-cured LAFC53 and LN B&W are thin-bodied, smooth, dark green, and also of poor quality. Again, the K326 PMT-RNAi line shows wavy, moderate-ripened, and broad leaf, and exhibits a higher leaf quality compared to LAFC53 (FIGS. 1B and 1D).

Figure 3:
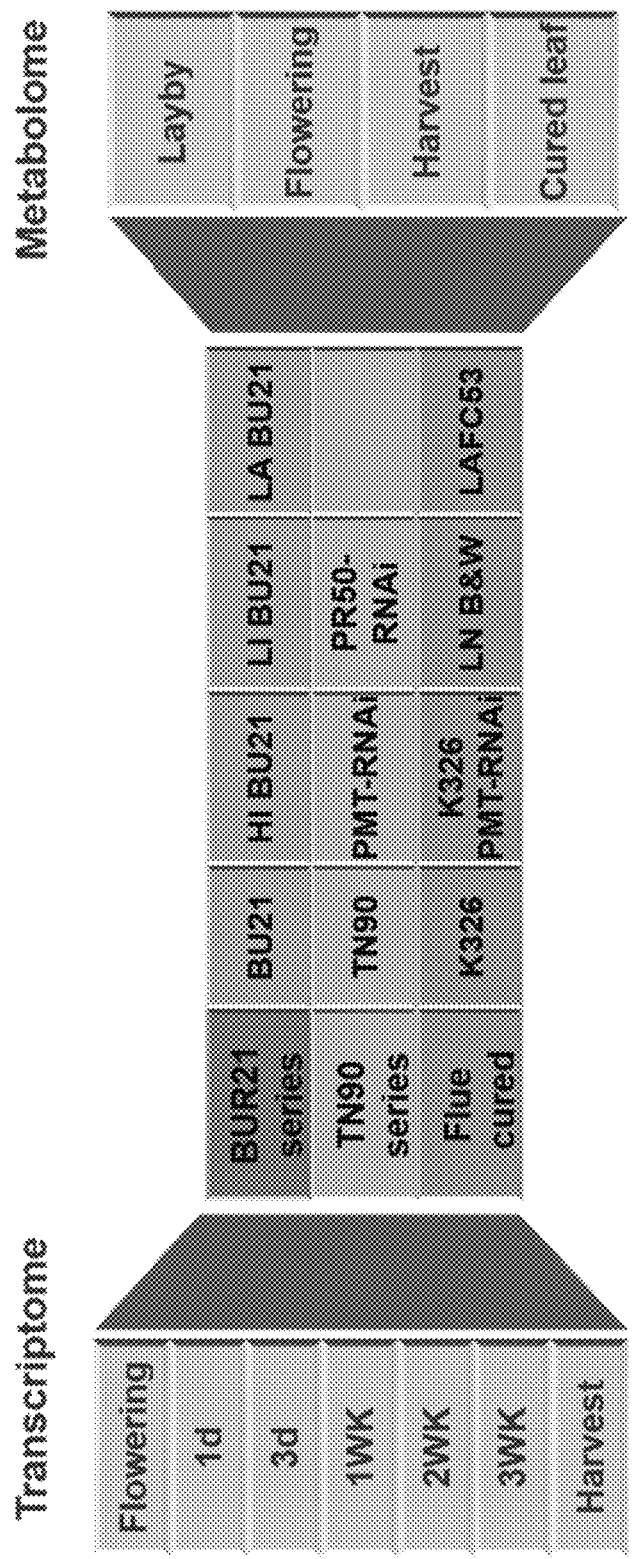
FIG. 3 depicts leaf transcriptome and metabolome sampling matrix. In total, 231 RNA-seq samples are collected (from 11 varieties, 7 stages, and 3 biological replicas for each time point). Meanwhile, 132 metabolome samples are obtained (from 11 varieties, 4 stages, and 3 biological replicas for each time point).

At 7 different time points including flowering and 6 post-topping time points (1-day post-topping, 3-day post-topping, 1-week post-topping, 2-week post-topping, 3-week post-topping, and harvest), leaf number 8 is collected for next generation sequencing analysis (FIG. 3). At 4 different time points including layby, flowering, harvest and cured leaf samples, leaf numbers 5-7 are collected for metabolite analysis (FIG. 3). Each time point is represented by three independently collected samples. These three samples served as biological replicas.

TABLE 8

Tobacco lines used in transcriptional and metabolic profiling.

| Background | Variety | Genotype |
|---|---|---|
| Burley | TN90 | Control |
| Burley | TN90 PMT-RNAi | Putrescine N-methyl transferase RNAi in TN90 background |
| Burley | TN90 PR50-RNAi | PR50 (ribosomal protein) RNAi in TN90 background |
| Burley | BU21 | Burley 21 |
| Burley | HI BU21 | nic2 in BU21 background |
| Burley | LI BU21 | nic1 in BU21 background |
| Burley | LA BU21 | nic1 and nic2 mutations in BU21 background |
| Flue-cured | K326 | Control |
| Flue-cured | K326 PMT-RNAi | Putrescine N-methyl transferase RNAi in K326 background |
| Flue-cured | LAFC53 | nic1 and nic2 mutations in NC95 background |
| Flue-cured | Brown & Williams Low Nicotine ("LN B&W") | nic1 and nic2 mutations in a flue-cured background |

Figure 4:
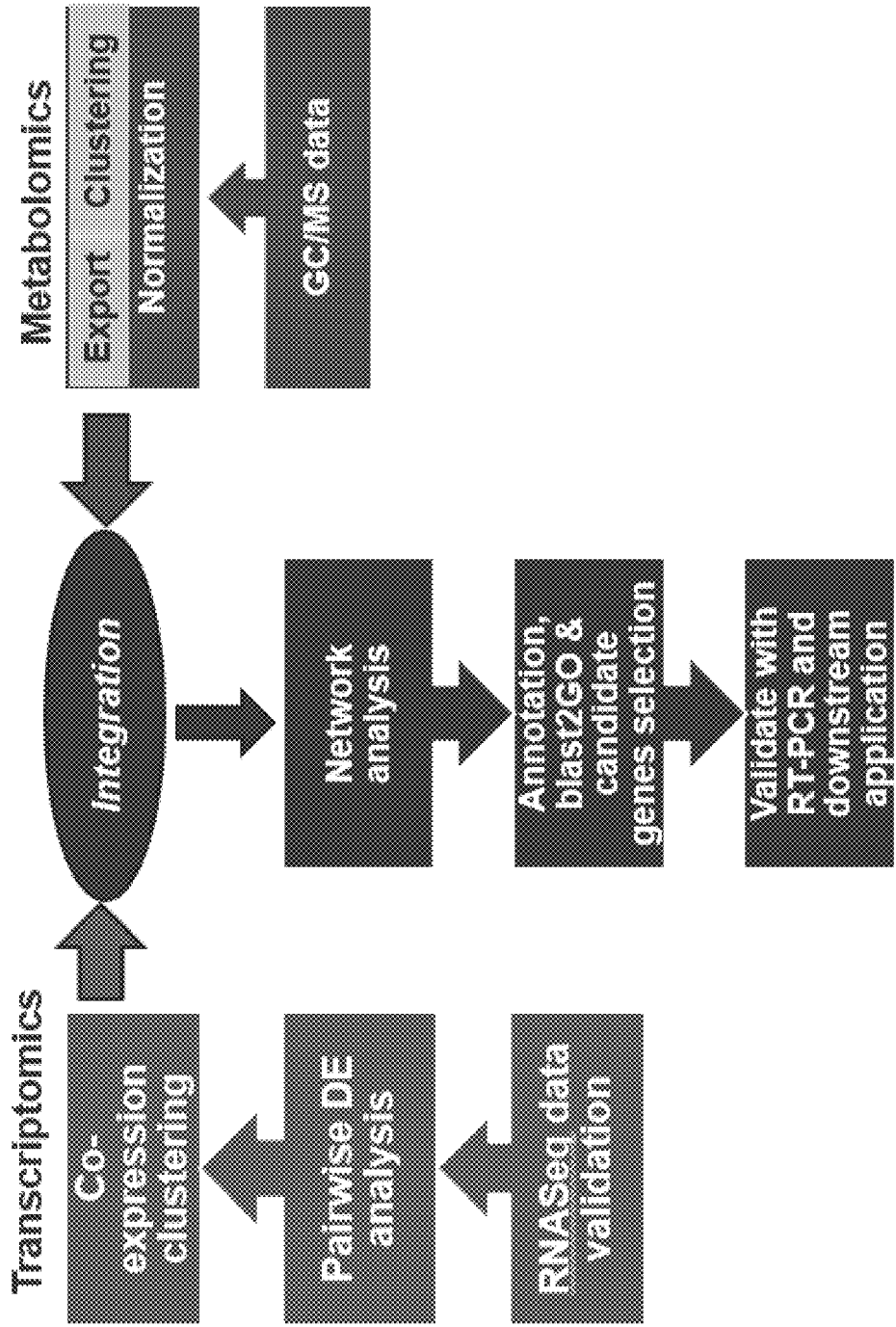
FIG. 4 depicts leaf transcriptome and metabolome data analysis flowchart.

Example 2: RNA Sequencing and Metabolite Analysis of Tobacco Lines with Various Reduced-Nicotine Levels RNA from the leaf samples described in Example 1 is isolated using RNeasy Plant Mini Kit (Qiagen, MA). RNA quality is tested using Agilent Plant RNA Nano Kit and a 2100 Bioanalyzer (Agilent Technologies, Calif.). Two hundred thirty-one (231) cDNA libraries are constructed, with indexing using a TrueSeq RNA Library Prep Kit v.2 (Illumina). cDNA libraries made from the same biological replicates are pooled together, and each pooled replicate is analyzed on an Illumina HiSeq 2000, generating 100-bp single reads with a minimum of 30 million reads per sample. Gene expression data from 11 varieties and 7 time point samples are analyzed to identify leaf-quality related genes. Gene reads are mapped to an internal tobacco genome database. EdgeR in CLC genomic workbench is used to perform differential gene expression analysis. Gene expression data is filtered for differential expression between low-alkaloid lines and their corresponding normal-nicotine control (FIG. 4). FDR adjustment is performed on all p-values and a cut-off of an FDR-corrected p-value<0.05 is used.

Figure 5A:
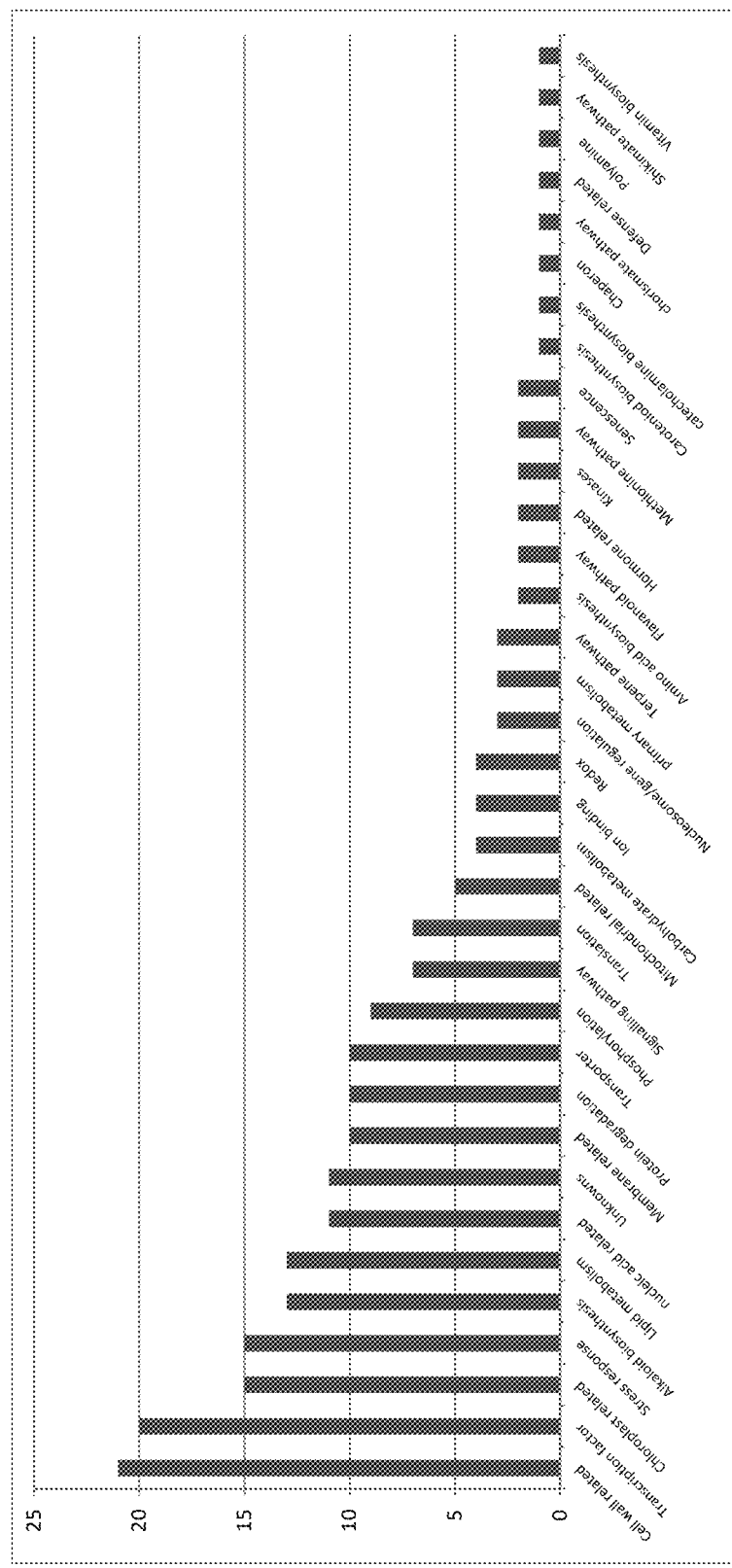
FIG. 5A depicts functional analysis of differentially expressed genes in low-alkaloid burley varieties. In total, 218 genes are identified, falling into 35 functional categories.
Figure 5B:
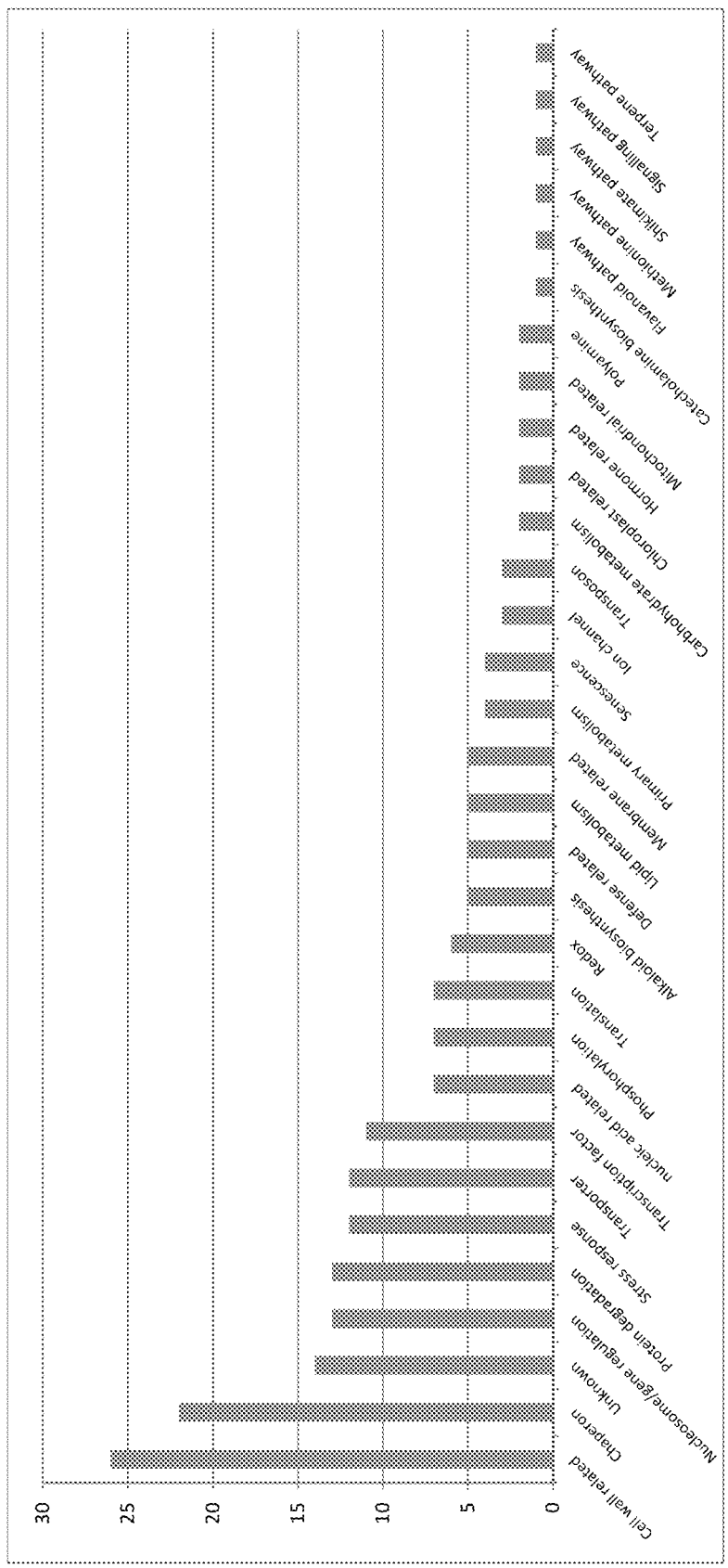
FIG. 5B depicts functional analysis of differentially expressed genes in low-alkaloid flue-cured varieties. In total, 200 genes are identified, falling into 31 functional categories.
Figure 5C:
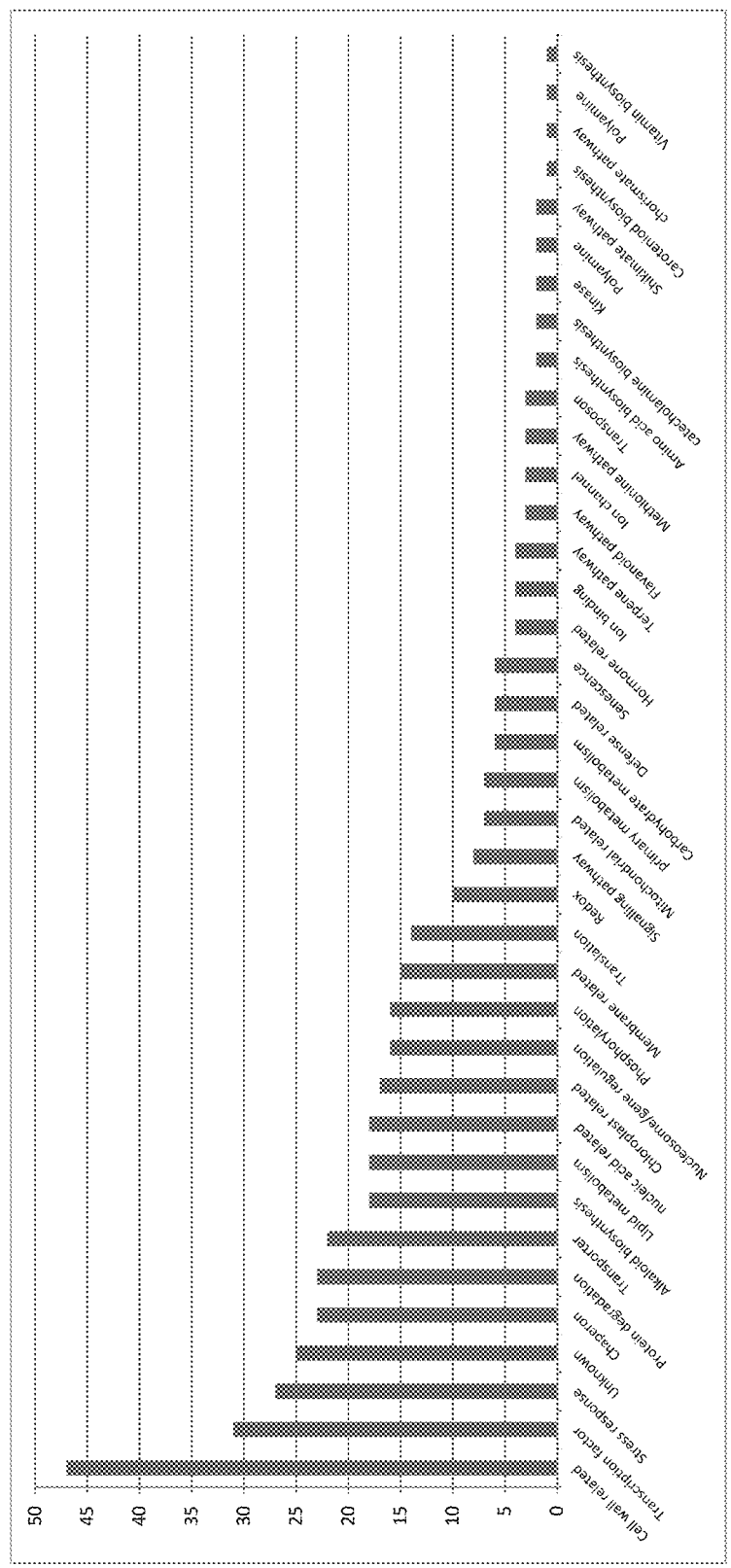
FIG. 5C depicts functional analysis of all differentially expressed genes based on combined data from burley and flue-cured. The 418 genes fall into 38 functional categories.
Figure 5D:
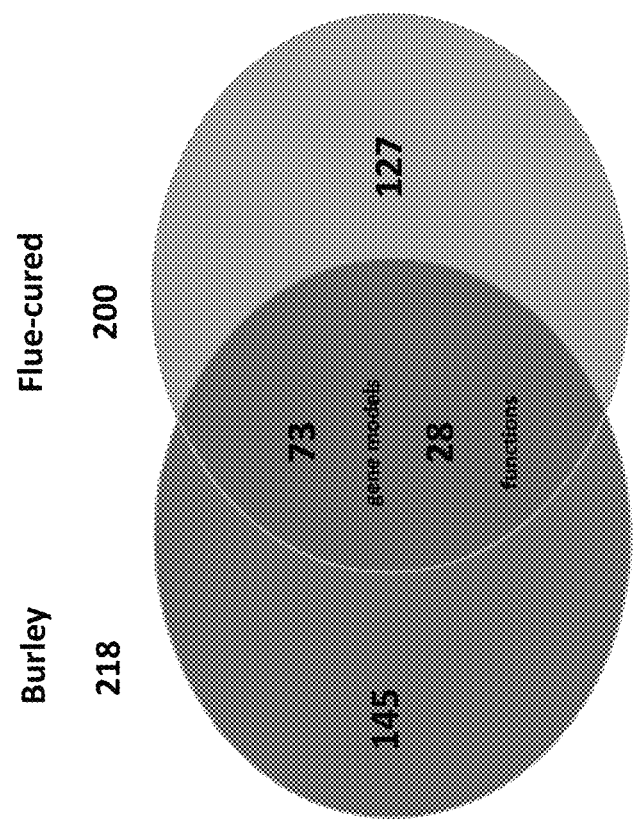
FIG. 5D depicts seventy three (73) genes appear differentially expressed in both the burley data series and the flue-cured data series. They fall under 28 functional categories.
Figure 6:
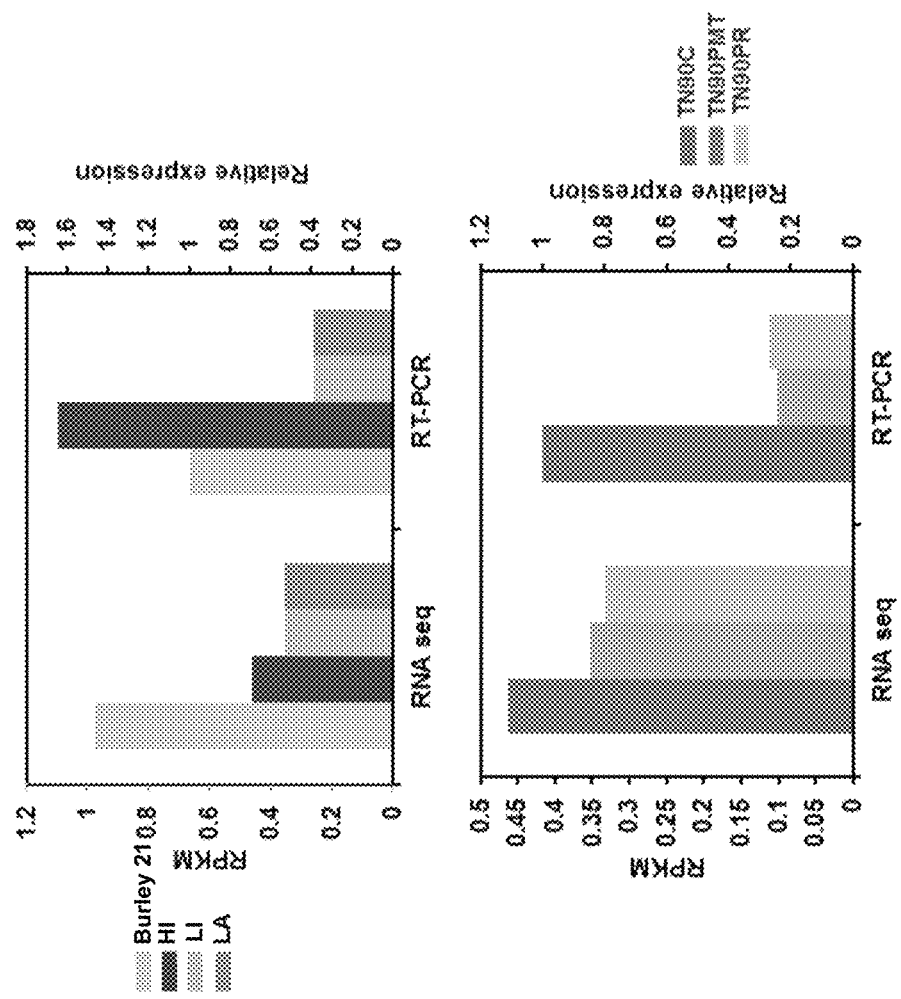
FIG. 6 depicts the expression of WRKY Transcription Factor 45 is reduced in low-alkaloid lines, shown by both RNA-seq data and RT-PCR validation.
Figure 7:
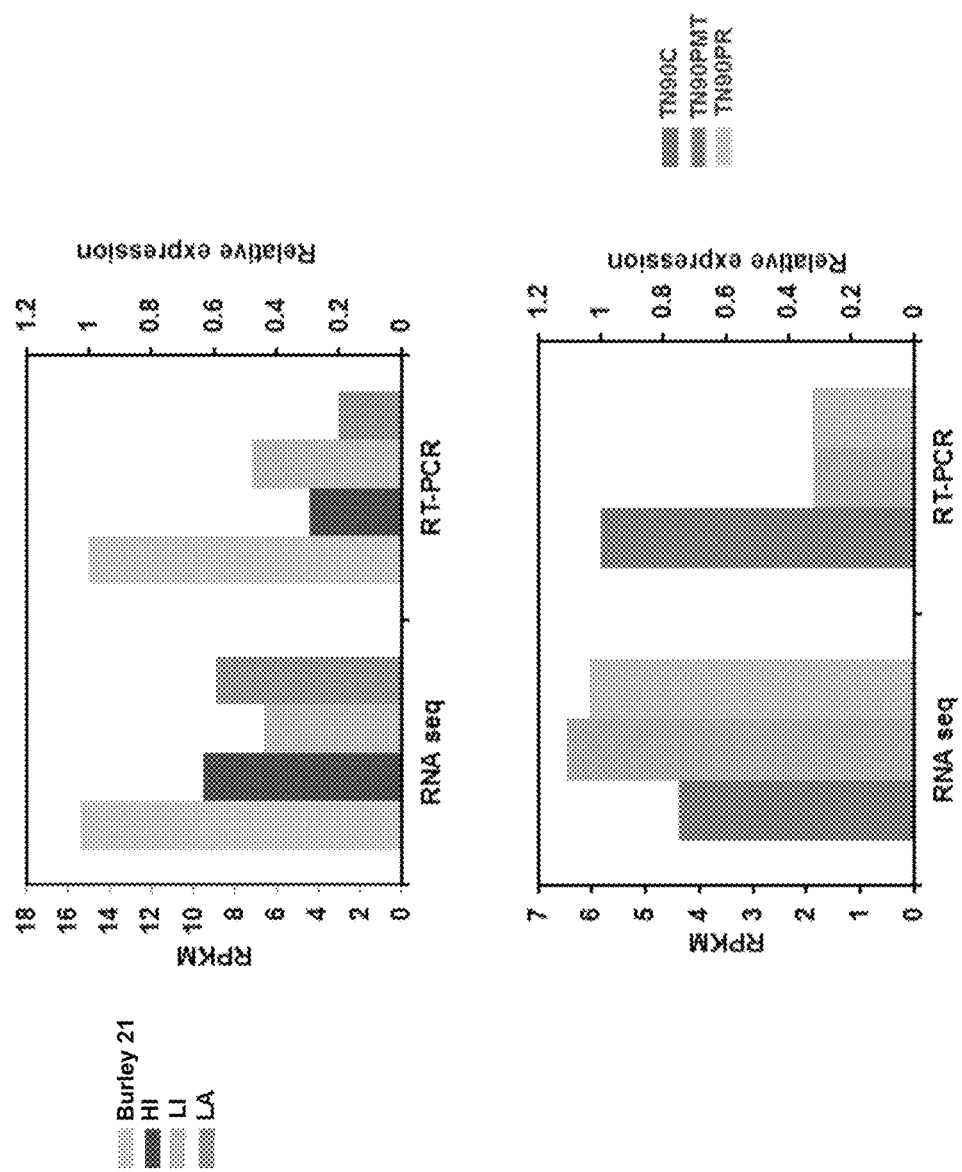
FIG. 7 depicts the expression of a cellulose synthase is reduced in low-alkaloid lines, shown by both RNA-seq data and RT-PCR validation.

Based on the transcriptome analysis, 218 genes from the burley variety series and 200 genes from the flue-cured variety series are identified to be differentially expressed between low-alkaloid lines and control. These genes belong to 38 functional categories (FIGS. 5A-C). Seventy three of the 418 gene functions are common in both flue-cured and burley varieties (FIG. 5D).

Metabolite analysis is conducted in parallel to determine the flux of nitrogen through the metabolic pathways of low-alkaloid lines and relate the metabolite data to the gene expression data (FIG. 4). Shotgun metabolomics is performed by Metabolon Inc. using a combination of UHPLC-MS/MS and GC-MS. Relative levels of ~900 compounds from leaves are evaluated. A subset of these compounds, 114 compounds from burley leaves (TN90 and BU21 series combined) and 62 compounds from Flue-cured leaves are identified with high confidence. Relevant metabolites are then used to screen and validate the gene expression differences observed from the transcriptome analysis.

Example 3: Confirmation of Selected Candidate Gene Expression

A list of differentially expressed candidate genes is identified based on the combined transcriptome and metabolome approach outlined above. To confirm the expression pattern of selected candidate genes, their expression is further analyzed in 10-16 different tissue samples (6 axillary bud samples (before topping and 2 hr, 6 hr, 12 hr, 24 hr and 72 hr after topping), young leaves 24 hr after topping, mature leaves, senescent leaves, midrib, stalk before topping, stalk 24 hr after topping, shoot apical meristem, and two root samples (before topping and 24 hr after topping)).

In brief, total RNA is isolated using TRI Reagent (Sigma-Aldrich, St. Louis, Mo.). To remove DNA impurities, purified RNA is treated with RNase-free DNase (Turbo DNA-free, Ambion, Austin, TX). To synthesize the first cDNA strand, approximately 10 μg of total RNA is transcribed utilizing the High Capacity cDNA Kit (Applied Biosystems, Foster City, Calif). To measure the level of selected gene transcripts in the samples, RT-PCR is performed using SYBR Green PCR Master Mix (Applied Biosystems, Foster City, Calif) with gene-specific primers. Real-time gene expression verification leads to the identification of a list of candidate genes with confirmed differential expression between low-alkaloid and control lines (Tables 9 and 10). These genes provide exemplary Leaf Quality Genes (LQGs).

TABLE 9

Target LQG genes for improving leaf quality by overexpression.

| # | Gene ID | Gene Function | Functional Category | cDNA SEQ ID No. | Protein SEQ ID No. |
|---|---|---|---|---|---|
| 1 | g11944 | Bzip transcription factor 27 | Transcription factor | 1 | 18 |
| 2 | g15911 | WRKY transcription factor 45 | Transcription factor | 2 | 19 |
| 3 | g17677 | Basic helix-loop-helix transcription factor | Transcription factor | 3 | 20 |
| 4 | g7693 | NAC domain-containing protein, putative | Transcription factor | 4 | 21 |
| 5 | g7893 | Cellulose synthase family protein | Cell wall | 5 | 22 |
| 6 | g17067 | Xyloglucan endotransglucosylase/hydrolase | Cell wall | 6 | 23 |
| 7 | g67849 | Arabinogalactan protein family | Cell wall | 7 | 24 |
| 8 | g49262 | SAUR-like auxin-responsive protein | Hormone | 8 | 25 |
| 9 | g77221 | Gibberellin receptor GID1, putative | Hormone | 9 | 26 |
| 10 | g37403 | Indole-3-pyruvate monooxygenase YUCCA4 | Hormone | 10 | 27 |
| 11 | g12075 | Glucosyltransferase | Others | 11 | 28 |
| 12 | g26335 | PAR1 protein | Others | 12 | 29 |
| 13 | g78744 | Glycine rich protein | Others | 13 | 30 |
| 14 | g73708 | Plastid-lipid associated protein | Others | 14 | 31 |
| 15 | g68786 | Terpene synthase | Others | 15 | 32 |

TABLE 10

Target LQG genes for improving leaf quality by suppression.

| # | Gene ID | Gene Function | Functional Category | cDNA SEQ ID No. | Protein SEQ ID No. |
|---|---|---|---|---|---|
| 1 | g63887 | Cytochrome P450 | Others | 16 | 33 |
| 2 | DUF581 | Unknown function | Others | 17 | 34 |

Example 4: Development of Transgenic Plants Containing RNAi or Overexpression Constructs To investigate the function of candidate genes, transgenic plants are generated expressing either the full length coding sequence of overexpression gene candidates (Table 9) or an RNAi sequence for downregulation of the suppression gene candidate (Table 10). An expression vector, p 45-2-7 (see, for example, SEQ ID NO:57 in US 2015/0173319), is used, which has a CsVMV promoter and a NOS terminator, as well as a cassette having a kanamycin selection marker (NPT II) under direction of the actin2 promoter and a NOS terminator. The nucleic acid constructs carrying the transgenes of interest are introduced into tobacco leaf discs using an *Agrobacterium* transformation approach. See, for example, Mayo et al., 2006, *Nat Protoc.*, 1(3):1105-11 and Horsch et al., 1985, *Science* 227:1229-1231.

Briefly, ascetical tobacco plants (Tennessee 90 (TN90)) are grown from magenta boxes, and leaves discs are cut into 15×150 mm plates. *Agrobacterium tumefaciens* containing the target plasmid are collected by centrifugation of 20 ml cell suspension in 50 ml centrifuge tube at 3500 rpm for 10 minutes. Supernatant is removed and *Agrobacterium* cell pellet is resuspended in 40 ml liquid resuspension medium. About 25 ml of the solution is transferred to each 15×100 mm Petri plates. In those 15×150 mm plates, tobacco leaves, avoiding the midrib, are cut into 0.6 cm disk. Leaf disks are placed upside down, a thin layer of MS/B5 liquid resuspension medium is added, and slices are made with a #15 razor blade. The leaf discs are poked uniformly with a fine point needle. Eight disks are placed, upside down, in each regeneration plate (15×100 mm). *Agrobacterium tumefaciens* suspension is added and the leaf discs are incubated for 10 minutes.

Leaf disks are transferred to co-cultivation plates (½ MS medium) and disks are placed upside down in contact with filter paper overlaid on the co-cultivation TOM medium (MS medium with 20 g sucrose/L; 1 mg/L IAA and 2.5 mg/L BAP). The plate is sealed with parafilm and labeled appropriately. Plates are incubated in dim light (60-80 mE/ms) and 18/6 photoperiods at 24° C. for three days. Leaf disks are transferred to regeneration/selection TOM K medium plates (TOM medium with 300 mg/l Kanamycin) and subculture bi-weekly to the same fresh medium in dim light at 24° C. until shoots become excisable. Shoots from leaves are removed with forceps and inserted in MS basal medium with 100 mg/L kanamycin at 24° C. and 18/6 photoperiods with light intensity of 6080 mE/ms for rooting.

When plantlets with both shoots and roots grow large enough (e.g., reach over half of a GA7 box), they are transferred to soil for acclimatization. During the transfer, the gel is washed from the root tissue with tap water. Established seedlings are transferred to the greenhouse for further analysis and to set seed.

Example 5: Improve Leaf Senescence in Low-Alkaloid Lines

Low-alkaloid lines stay green for longer compared to normal-alkaloid lines. Triggering leaf senescence can lead to breakdown of chlorophyll. Leaf senescence can be triggered and promoted by various environmental stressors, developmental cues, and endogenous hormone signals. WRKY transcription factors have been reported to regulate leaf senescence. In particular, *Arabidopsis* WRKY45 is proposed to accelerate senescence by regulating a cascade of SENESCENCE-ASSOCIATED GENEs (SAGs). See Chen et al., *Molecular Plant*, 2017, 10(9):1174-1189.

WRKY DNA-binding protein 45 (WRKY45, g15911) is differentially expressed in low-alkaloid lines, and is overexpressed in low-alkaloid tobacco lines (e.g., LA BU21 or a mutant line with all five PMT genes knocked out via gene editing) as described in Example 4. Leaf senescence phenotype and leaf quality are both monitored in the overexpression lines.

Example 6: Modification of Cell Wall Related Genes in Low-Alkaloid Tobacco Leaves Plant cells are surrounded by a polysaccharide-rich cell wall that aids in determining the overall form, growth and development of plant body. Most plant cell walls are composed of a frame work of cellulose microfibrils that are cross-linked to each other by branched hetero-polysaccharides which are referred to as hemicelluloses and pectins. Hydrophobic lignin is also deposited throughout the secondary walls which results in dehydration of the cell wall compartment. This composition increases the strength of the walls and reduces their flexibility. Xyloglucans is the main hemicellulose in dicot primary walls and xylans are major hemicellulases in secondary cell walls and both xyloglucans and xylans cross link cellulose microfibrils. Cell wall related genes (g7893, g17067 and g67849) are over-expressed in low-alkaloid varieties (e.g., LA BU21 or a mutant line with all five PMT genes knocked out via gene editing) as described in Example 4. Leaf quality is measured in the overexpression lines to show that these cell wall-related genes play a role in tobacco leaf quality.

---

The invention claimed is:

1. A modified tobacco plant, or part thereof, comprising a recombinant nucleic acid construct comprising a heterologous constitutive promoter operably linked to a polynucleotide comprising at least 98% identity to the nucleic acid sequence of SEQ ID NO: 2.

2. The modified tobacco plant, or part thereof, of claim 1, wherein said modified tobacco plant is a *Nicotiana tabacum* plant.

3. The modified tobacco plant, or part thereof, of claim 1, wherein said modified tobacco plant, or part thereof, further comprises a mutation conferring a reduced level of nicotine relative to a control plant not having said mutation or transgene.

4. The modified tobacco plant, or part thereof, of claim 3, wherein said modified tobacco plant is a low-alkaloid tobacco plant.

5. The modified tobacco plant, or part thereof, of claim 3, wherein said mutation conferring a reduced level of nicotine comprises a nic1 mutation, a nic2 mutation, or both.

6. The modified tobacco plant, or part thereof, of claim 5, wherein said nic1 mutation, said nic2 mutation, or both are introgressed or derived from a variety selected from the group consisting of LA Burley 21, LAFC53, LN B&W, and LN KY171.

7. The modified tobacco plant, or part thereof, of claim 3, wherein said mutation conferring a reduced level of nicotine comprises a mutation in a gene or locus encoding a protein selected from the group consisting of aspartate oxidase, agmatine deiminase (AIC), arginase, diamine oxidase, arginine decarboxylase (ADC), methylputrescine oxidase (MPO), NADH dehydrogenase, ornithine decarboxylase (ODC), phosphoribosylanthranilate isomerase (PRAI), putrescine N-methyltransferase (PMT), quinolate phosphoribosyl transferase (QPT), S-adenosyl-methionine synthetase (SAMS), A622, NBB1, BBL, MYC2, Nic1_ERF, Nic2_ERF, ethylene response factor (ERF) transcription factor, nicotine uptake permease (NUP), and MATE transporter.

8. The modified tobacco plant, or part thereof, of claim 3, wherein said mutation conferring a reduced level of nicotine comprises a mutation in a gene or locus encoding a protein selected from the group consisting of ERF101, ERF110, ERFnew, ERF199, ERF19, ERF130, ERF16, ERF29, ERF210, and ERF91L2.

9. The modified tobacco plant, or part thereof, of claim 3, wherein said mutation conferring a reduced level of nicotine comprises a mutation in a gene or locus encoding a protein selected from the group consisting of ERF32, ERF34, ERF39, ERF189, ERF115, ERF221, ERF104, ERF179, ERF17, and ERF168.

10. The modified tobacco plant, or part thereof, of claim 1, wherein said polynucleotide encodes an amino acid sequence at least 99% identical to the amino acid sequence of SEQ ID NO: 19.

11. The modified tobacco plant, or part thereof, of claim 1, wherein said polynucleotide encodes an amino acid sequence identical to the amino acid sequence of SEQ ID NO: 19.

12. The modified tobacco plant, or part thereof, of claim 1, wherein said polynucleotide comprises at least 99% identity to the nucleic acid sequence of SEQ ID NO: 2.

13. The modified tobacco plant, or part thereof, of claim 1, wherein said polynucleotide comprises the nucleic acid sequence of SEQ ID NO: 2.

14. The modified tobacco plant, or part thereof, of claim 1, wherein said constitutive promoter is a CaMV 35S promoter or a CsVMV promoter.

* * * * *

SEQUENCE LISTING

<160> NUMBER OF SEQ ID NOS: 34

<210> SEQ ID NO 1
<211> LENGTH: 513
<212> TYPE: DNA
<213> ORGANISM: Nicotiana sp.

<400> SEQUENCE: 1

```
atggaagaag tttggaaaaa cataaatctt tcttctctaa atgacgacac tactacttct      60
tctagagatc atattgatcc acaacaaaat attagtaatt ctaccaattt tggtggcatg     120
attttacaag atttcttggc taggccattt gctaataacc ctaaaacagc agcaaaaggc     180
tatgtccccc ctattttcc tcctcctgct gctgctgctg ttactgtgtt gacattaaac     240
tctggccctg gacttcattt ctttggtaac ttaaggcaaa actcaagttc tgagcagcaa     300
aaatctattt ctaatacgtc atttgaggat ttggcttcac cagttggagg gaatactaat     360
ggaagaaaga ggtgcagtga gtctgatgat aacaattcaa gtgaccagaa aaacaagagg     420
atgatcaaga accgtgagtc tgctgctaga tcaagggcta gaaagcagga aagtgcagct     480
tctctattta cactcccaac atgtgttttt tag                                  513
```

<210> SEQ ID NO 2
<211> LENGTH: 549
<212> TYPE: DNA
<213> ORGANISM: Nicotiana sp.

<400> SEQUENCE: 2

```
atggagaatc agtcgatgcc ctttcttggt tcaacaagct gtgttcgaac catttcttct    60
gactcctttt caaattcgat aaatattggt tataactcta tgaatggatg gacctcggga   120
ttaaagaccg agatttctaa ttctacagca agagagcaaa acataaccaa catcaaaaac   180
agccttatgg gagtggtttc atcagaaatt catactacca atattatatc atcccttaag   240
aaaaaggggg ataagaaaat taagaagcct agatttgctt ccaaacaag aagccaagtt    300
gatattcttg atgatggata tcgctggaga aaatatggac aaaaagctgt caagaacaac   360
aactacccaa gaagctacta caaatgtaca catcaaggat gcaatgtgaa gaagcaagta   420
caacgccttt ccaaagatga aggagttgtg gtcaccactt atgaaggcat gcacactcat   480
cctattgaca agcccacaga caattttgaa caaatcctcc atcagatgca tattattcct   540
ccccattaa                                                            549
```

<210> SEQ ID NO 3
<211> LENGTH: 684
<212> TYPE: DNA
<213> ORGANISM: Nicotiana sp.

<400> SEQUENCE: 3

```
atggattatg cttctctgga gacacgtact catgatcctt taaattatat taacaataat    60
tcccaggtca ataagagact acccaaaaga atattaggta ctactgataa taatattcca   120
gataagaaag atgaaactgc tgccgctgct gctactcctg atgatttcaa gcttacaaga   180
attatgcata gagatatcga acgtcaaaga agacgagaaa tgtctgccct ttactcttcc   240
ctccgttctc ttcttcctct gcaatatgtc aagggcaagc gttcggtatc ggaccacatg   300
catgaagctg tgaattatat aaaagaaatg caagcaaaca tgaaggaatt ggagaaacgg   360
agagacttgc taattaagtc gtccttaccc aattcaataa gatcaaataa tttcacagtt   420
tctccagatt gtgtcacggt aagcccctgc ctgcagggtg gcatagagat cttgatcagc   480
gttgactgta aagcgcaaag tttccccctt tcaagagtgc tgagggagct tctgaaacaa   540
gggattaatg tcgtcagttg tgtctctgca aaagtgaatc aaaggtcact gcacacaatt   600
cagatcgagg tgtgcgatat gaacaacatt gatcaccagg cattgcaaca aaaagtgatt   660
gatttaatca atgtggactt gtag                                           684
```

<210> SEQ ID NO 4
<211> LENGTH: 960
<212> TYPE: DNA
<213> ORGANISM: Nicotiana sp.

<400> SEQUENCE: 4

```
atggaattag tggaaaatat agcagctaat actaatatta agctgaaga tgaagaagaa     60
atgatgcaac ttccaggttt tcggtttcat cctacagatg aagagcttgt gagtttttat   120
cttaaacgca aagtggaaaa caaaaagatc aaaatcgatc ttatcaaaga ggttgatatc   180
tacaaacatg atccttggga tcttccaaaa gggaacacag tgggggataa ttgtaaggaa   240
tggtatttct tcagcatgag agggagaaag tacagaaaca gtgtaagacc aaatagagta   300
acaggttctg ttttttggaa agcaacagga attgacaagc ctatttatag tagtactact   360
actacatcac aaagtacaga tcgtgaatgc attggcctca gaaatcatt agtatattat    420
aggggaagtg ctggcaaagg aacaaaaact gattggatga tgcatgagtt tcgcctccca   480
```

```
ccaaattgga agacttcaaa ccaacagctg cccaatccca agaacattat tccagaagct    540
gaagtttgga cactatgcag aatattcaag aggacttcaa attacaagag attcacacca    600
gattggaagc agcccgttat taaacaaagt tttggtgatg caagttctaa agcatgcagt    660
cttcaatctg aaacaagtga tgatcactct attaatatca acttcaataa gatggagttt    720
ccacataaga aaataatac agcaactgga ggaaattatc aagttgatca aaaaaccaca    780
cattaccaaa atagccaacc aataattacc atgcctcaat cttcaatcac atcatcaaac    840
tcaagctttt ggaatacaag tgctgaagag gagtatttgt ttagtgatgg aaactgggat    900
gaactcaaat ccgtcgttga tttagctatt gatcctcgta gtcttttgg atttagataa    960
```

<210> SEQ ID NO 5
<211> LENGTH: 2256
<212> TYPE: DNA
<213> ORGANISM: Nicotiana sp.

<400> SEQUENCE: 5

```
atggcgccca aacaccttc tcttcctctt tacgaaatta agtatcgaaa aacattatt     60
tcaagaggaa tagaactctt cattcttttc ctattgttct cactcttggc ctatagactc    120
ctctctctta aaaccatgg ttttagtttg ccattcttct tagctcttat atgtgagtca    180
tggttcactt tcctttggat tctcaccatt aacgccaaat ggaatcaagt cgaaccaaaa    240
acatatcctc tacgcctttt ggaaaggacg gcagagtttc ctgcagtgga catgttcatt    300
acaactgcag atcccatcct agagccgcct cttataacag taaacacaat gttatcatta    360
ttagcagtgg attatcctgc taataaacta gcttgttatg tctcagatga tggtgcatct    420
cctattacct attattcact tgttgaagca tctaaatttg ctaagctttg ggttcctttt    480
tgtaagaagt ataatattgc acttagagcc ccttttcgat attttagtgc taactcatta    540
ccaccccaag atacttcaca agggttcccc gaagattgga aaaggatgaa ggatgaatat    600
aaacagctgt gtgaaaagat agaagatgca agtacacaag aagcagaggc atgtgatttt    660
tcaggagatt ttgctgtttt ctcaaaaatt gaacgcaaaa accatccaac cattataaag    720
gtaatattgg aaaacaagga gggtattgct gatggcttgc ctcatcttgt ctacatctca    780
cgagagaagc gtccaaaaca tccccatcac ttcaaagccg gcgccatgaa cgttctgact    840
agagtctctg gattgatgac aaatgctcca tttatgctta atgtggattg tgacatgtat    900
gcaaataacc cacaagttgt tcaacatgct atgtgttatt ttcttggtgc taaggatgaa    960
aaagactgtg gttttgttca atttccacaa tacttctacg atggattgaa agatgatcct   1020
tatggtaatc aattaaaagt cttacacgag tatttgggaa gaggatttgc tggcattcaa   1080
gggccatttt atcaaggaac aggatgtttc catagacgaa agattatata tggcttgtca   1140
ccaaatgaaa aataaatac tggagaattg agggatgaat atctacagaa aacttatgga   1200
aaatcacaga gttattagc atcagttgct cagactctat cagcaggatc aaataatatt   1260
gagcaagtta attctgattc tctctcgagt ttcattgagg aagcacagca aattggaagt   1320
tgtggatatg aatttggtac tgcctggggt caaaagctgg gctggctata tggatgtgca   1380
acagaggatg tactcactgg gcttcttatc caagggaaag gctggagatc cgcttactgt   1440
gcacccgacc cgcctgcttt tcttggaact gcaccttcgg gtgggccggc ctcgatgacc   1500
caacagaaga gatgggctaa tgggcttttt gaaattcttt tcttcagtaa aagcccaatt   1560
attggaactc ttttcggaaa gcttcaattg aggcaatgca tggcttattt gtatatccaa   1620
ctatgggcct tgagatccat ttttgaagtt tgttatgcta ttctgcctcc ctattgcctc   1680
```

```
atcaccaatt ccagcttttt acccaaggct aatgaaccaa gtatggttat accggcatca    1740
atctttatca tctacaatct atatggttta tcagagtatg ttagagcaaa tgagccaata    1800
aaagcatggt tgaacaatca agaatgtgg agagtcaatg ctatgactgc atggctattt    1860
gggattctag gtgctacaac aaaattactt ggaatttctg agactgcatt tgaagttaca    1920
aaaaaggacc aaggaaatga tggagatgac acaataatt ctaatattgg aaggttcaca    1980
tttgatgatt caccaatttt tgtgcctggc actgcaattc tcttattgaa cctcagttcc    2040
ttgttcattg ggatgttaga ttttaaacaa ggaaggatt gtgaatgggg attaggagag    2100
gttatatgca ttatgtgggt acttttcata ttttggtcat ttttgaaagg gttatttgct    2160
aaagggaagt atgggattcc agcaacaact attctcaagt caggggcatt ggcattgttg    2220
ttagttcatc ttttcaagtt taccaataaa ttgtaa                              2256

<210> SEQ ID NO 6
<211> LENGTH: 477
<212> TYPE: DNA
<213> ORGANISM: Nicotiana sp.

<400> SEQUENCE: 6
atgaatgaga atggttcaac taaacttctc caagctcaaa ctcaaacatg gaaccatatc      60
tacaacttcg taagctcttc agcagcaaaa tgtgcagttc aactaggcat ccccgatgtt     120
gtcctcctcg ctcccctaaa atcctatctg ctgaattttt tcatggttaa acagtggatt     180
ctccataatt ggggagacga agattgtgtg aagatattaa agaaatgcaa agagtcaatt     240
ccaagtagag aaaaaggcgg gaaagtgata attataggca tagtgctgga aaatccgaag     300
gaaaaggatg attctgttcg agcacaacat aatatggact tggtgatgat ggttctttt      360 ggtgccaaag agagaactaa gaaggaatgg gaaaaactct tcactgaagc tggtttcaat     420
gaatatgaaa taactcccac cctgggcaca aggtctctca ttgaaatcta cccttga        477

<210> SEQ ID NO 7
<211> LENGTH: 606
<212> TYPE: DNA
<213> ORGANISM: Nicotiana sp.

<400> SEQUENCE: 7
atggatagga agattgtatt tttagtgtca tttttgtgca ttgtagtggc cagtgtcaca      60
ggtcagacac ctgcggctgc accagccaaa gcaccagttg gtgctaaggc ttctacacca     120
ccagctgctg ctcccacaaa gcctaaaact cctgctcctg ctactgcacc tgcctcagct     180
ccacccacag ctgtttctac tcctccagca gctgcaccag ccactgctcc tactacccct     240
gttgttactc cacctgtatc agcaccacca gctaaaacac cagctagttc tccaccagct     300
gcagtgcctg tgagttcacc accaccagcg gttacaccgg tacaatctcc accagcacca     360
gctccggtgg cagcgacacc accagctgct ctgctccac ctgctccagt tccagtttca      420
gcatcttctc cagcaccttc tcctgatatg atgagcccac ctgcacctcc tactgaagct     480
cctggaccta gcatggattc cgactctccc agtccatctc tcaacgatga gagcggagca     540
gagaaattga gatgcttgg aagcttggta gctggatggg ctgtgatgag ctggttcttg      600
ttctaa                                                                606

<210> SEQ ID NO 8
<211> LENGTH: 1542
<212> TYPE: DNA
```

<213> ORGANISM: Nicotiana sp.

<400> SEQUENCE: 8

```
atggaaaagg aaaagaagat agacatggaa gaaaagcatg aaaaggaatt gaaggagaaa      60
gagaaaaagg ataaagtaaa aaatacgggg agcgaagagg agtcggagga aacagaggac     120
gagaaagatg gtgcaacaaa aatgtaaaa gaaaagaaat acaagaagga aaagaaagag      180
aaaaaggata agaaaagaa agacaagagt aagaggagg agtcggagga agaaaccgag       240
gaagagaagg atgatggaaa agggaagaag gataaaaaga gaaacataa gacagatatg     300
aaagagaaaa aggataaaga gatgaaagac aagagcaaac atgagtcaga aaagaagac     360
agcaaagaaa tagaggaaga aaggatgac ggagaagggg agaagaaaga taagagaag     420
aaactcaaga agggaaagaa agacagaaag gaaaaagaga agaaagacaa gagcatagag    480
gagtcgaagg aagaaaagga tgatgataaa ggggagaaga aggataaaga gcagaaagac    540
aagaaggaga aaagaacaa ggaagagaaa ggcaagagca aaggggaatc agaagaagaa     600
accgaggaag agaaggatga tgaaaaaggg aaaaacaag atcggatga agaagacgag     660
agacagacag aggaagagga gaatgatgaa aaggggtga agaaggataa ggagaagaaa     720
aacaaggaaa gaaagagaa aaaggacaac gaaaagaaag ataagagcaa agaggaaacg    780
gaggaagaga aggatgatga aaggagag aagaaggata agagaagaa atgcaagaag       840
aataagaaag agaaaaagga taagaaacg aaagacaaga gcaaagaggt gtcggatgaa     900
gaggaagaga agatgacga agaagggag aagaaggata aaaaaagaa acacaataag      960
gataagaaag aaacaaagga taagaaag aaatacaaga gcaaagagga gtcagaagaa       1020
gaagataaga agaaacgga ggaagagaag gatgatgatg aagaggtca gaagaaggaa      1080
aaagagaaga aaacaagaa ggataaaaaa gagaaaaagg ataagaaaa gaaagtcaag      1140
agcaaagagg agtcagatga agaagacaag caagacaagg tgaatgaggt tgaagtcgcc   1200
acaagagaga taaaaattga ggatgacaag aaaatatcgg acggtgaagc agacgagaaa    1260
ggtaaaagga aggagaaagg aaaagacagt aaagatgaga acaaaagga tgcaaaaaag     1320
gacaaagctg agaagacgag aaaacttgag gacaagtata aaagcaacgg taagttgaaa    1380
tccaagttgg agaagatcaa tgccaaactg gaagctcttc agcagaaaaa agcggacatc    1440
atgaagacaa taaagaagc cgaggataaa aacttagccg tggttgagag tcctaaagag     1500
gcagacctga aggcacacga tggagtaatg actgaacagt ga                       1542
```

<210> SEQ ID NO 9
<211> LENGTH: 1005
<212> TYPE: DNA
<213> ORGANISM: Nicotiana sp.

<400> SEQUENCE: 9

```
atgtctggtc aaaatgatga aattgctcta attgatccaa atgtcgatcc atatcgatat      60
ttgggcatta ggcgtaatac ggacgactct attatacgtc taccagaatc aactcttccg     120
tttgccacta ctattcctga tctttcctta gtcttcacta agatctcat cattaacccc      180
accaaaaaca cattggctcg tattgtcatc cctcgtaaag tactaaactc aaacaatatc     240
aataccacaa ccaaactccc tcttatagta tattttcatg gcggaggatt cgtaattgca     300
gctagtgtag acacaccgtt cttacaaacg ttttatgaaa cacttgtggc tgaaattcca    360
gccatagttg tatctgtcga ttatcgtac gcacccgaaa atcgacttcc agcagcttat     420
gatgattgta tcgaatcact gcattggatc aagaacaatc ctgatgagtt gctgaaaaaa    480
```

```
tatgctgatt tttctaagtg ttttctcatg gggacaagtg caggtggtaa cataacttac      540
catgtaggtt tacaagtcgc tggaattagt gaataccta agcctttaga aatcaaagga       600
ttgattttac atcatgcttt ctttggtggg aatgaaagga cacaatcgga actaaggtta     660
gcttttaaca agatattgtc actaaatgtg agtgatatta tgtgggagtt aggtttgcct      720
ataggaagtg atcgtgatca tccttattgc aatccaatgg gggagattaa atcaaatgat    780
aatttgtttg accaagtgaa atacaaggt tggaaagttt tgctgattgg ttgtgatggt     840
gatcctttga ttgatagaca aactgaactt tcgaaaatgt tgaaagaaaa aggggtgcaa    900
gttgtggaca tttttagtga gggagggttt catgcctgtg aatttttttga tcctaacaag   960 ttgaaagaat tggccgttgt tataatggag ttcgtgagag gttaa                   1005
```

<210> SEQ ID NO 10  
<211> LENGTH: 1161  
<212> TYPE: DNA  
<213> ORGANISM: Nicotiana sp.

<400> SEQUENCE: 10

```
atgggttctt ataaagaaga agaaaaaacc gatcaacaac caaaatggtt atgggttaat      60
ggacctataa tagtaggtgc tggaccttct ggtttagcag tttcagcttg tcttaaagaa     120
aatggagtcc cttcacttat tcttgaaaga agtgattgta ttgcttcttt atggcaacaa    180
aaaacttatg atcgtttaaa acttcatctc cctaaacagt tttgtcaact cccattattt   240
ggttttcctg aaaattttcc taaatacccc tcaaaaaaac tgttcatttc ttacttagag    300
gattatgcta aacactttgg tatagttcct aagtttaaac agtctgttaa agttgcagaa   360
tttgatcatg ttagtggatt ttggaaggta gaaactcaag attttttgta tctttcaaaa    420
tggttgattg tggctacagg agaaaatgca gagccagtaa taccagaaat tcaagggatt    480
gataagttta aggagcggt gttgcatact agtgttata agtcaggtac tgagtttaat    540
aatcaaaggg ttttggtaat tggttgtgga aattctggta tggaagttag cttggacctt    600
tgtagacata atgccatccc tcacatggtc gtcagaaatt ctgtgcatat tttaccaagg    660
gaaatgttag ggatatcaac attttcaata gcaatggcac ttctcaaatg gttgcctata   720
agagtagttg acaagttgct gttactagta gcaaatttga ccttaggtag cacagataag   780
ttaggtctcc ggcgaccaaa aaccggtcca cttgaactga aaaatgccac cggaaaaact    840
ccggtactcg acgttggtgc attgtcacaa ataagaaatg gaaaattca gattatgcac   900 ggtgtgaagg agataactaa aataggagca aagttttatag atggaaaaga aggagaatat   960
gattcaataa tcttagcaac tggatacaaa agcaatgttc cttcttggct taagggaact   1020
gacttcttca gaacaaagg gatgccaaag acaccatttc caaatggttg gaaggggaa   1080 aatggattat acacagtggg gtttacaaga agagggcttt tagggactgc aaatgatgca   1140
aaaaaattgc cagggacata a                                              1161
```

<210> SEQ ID NO 11  
<211> LENGTH: 1428  
<212> TYPE: DNA  
<213> ORGANISM: Nicotiana sp.

<400> SEQUENCE: 11

```
atggatagct cacaacttca tgttgctata gtctcaagcc ctggtatggg tcatttaatc     60
ccagttctag tcttaggcaa ccaattagcc acatatcata acatcaaaat tacatgcttt   120
```

```
gctatcacaa ccagctcttc ttcagcagaa actgaattcc tcaagaaatc cactctcacc      180
aatgagaaaa aaactataga aataattcca gttccttcaa acgatatttc ccacctaata      240
aattccagca ctaaagtttt cactaaatta cgactattag tccgcgaaac tttgcctaaa      300 attcgtctg  ccatagcatc catgactcat cgtccagatg ctctcattgt tgacattttt      360
ggcacacaaa tattgccaat tgctgaagaa tttaacatcc ctaaatacgc gtaccatctt      420
actactgcgt ggacattagc gttagctata tattgtcaag ttcttgagaa agagattgag      480
ggtgaatatg ttgatcttaa agaacctttg aaaattccag gttgcaaagc attgcgacct      540
gataacgtgt tggatcaatt gctggatcgg agtgatcagc agtatgaaga gtatgttaag      600
ccaggaatgg aatatacaga ttttgatgga atcttgatta atacttggga agatttagaa      660
cctgagacta tcaatgcact taaatataat gagaagttgc gattacttct taaagttcca      720
gttttcccaa ttggacccct tgaggagaaaa gttgaaacaa cttcgaatga cgaggtgatt      780
caatggttag acaagcaaaa taatgagtca gtgctatttg catcatttgg aagtggtgga      840
accctctcaa ctaagcaaat gaccgagctt gcatggggtt tagaattaag tcaacagaaa      900 tttgttttggg ttgtacgtcc cccgtccgac ggtgatgcag atagtgccta tctgaactct      960
accgaaaaag agacacgtgg catgtcggaa tacttgccgg aagggttctt aactaggact     1020
aaagatatgg gtttggtagt gcctatgtgg gccaaccaag tcgaaatttt gggtcactcg     1080
tcactgggtg gattttttgac acattgtgga tggaattcga cgatggagag cctgacaaat     1140
ggggttccaa tgattgcatg gccattacat gctgaacaaa aaatgaacgc cgccatgttg     1200
acggaggagc taggggtggc gattcggccg gcagttttgc cgacaaagaa attggtgaag     1260
agagaggaga ttcaagggat ggtgagaatt ttgatgcaga caaaagaagg aaagcctata     1320
gaggaaaagg ctaagaagtt aaagatgagt gcagaaaatg cactaagtga aggaggttca     1380
tcttacaact ccatttgtga gcttgtgaag gacattcaga gcagatag                  1428
```

<210> SEQ ID NO 12
<211> LENGTH: 555
<212> TYPE: DNA
<213> ORGANISM: Nicotiana sp.

<400> SEQUENCE: 12

```
atggcttcat tccatagctt gaagactttg gccattgttg ctcttgcaat ttcctccttt       60
gtgcaagtca ccctagggggg tatagcatgt gagaacttaa acgaagactc gtgtgccttc     120
gcaatatcaa gcaatgggaa gcgttgcgtg ctagagaaac atctgcgaag gagtggggaa      180
gaaggatata catgccgcac atcagaaata gaggctgata agcttaaaga ttggattgaa      240
accgatgaat gcattgaggc atgcggcgtc gatagaaatg cccttggcat ttcttccgac      300
gctctcctgg aatctcgctt taccaacaag ctttgctccc ctgcttgcta caaacattgc      360
cccaatattg ttgacctcta cttcaacctt gccgctggtg aaggtgtata tcttcccaag      420
ttgtgtgcag agcaagggaa aagtgcaagg cgagaaaatag cggagatcag aagctcggga     480
ttggtggcgc cagctccgga atcagaagtc aagcccagca atttcatgat tgctccggca     540
atgcctcctt tctaa                                                       555
```

<210> SEQ ID NO 13
<211> LENGTH: 618
<212> TYPE: DNA
<213> ORGANISM: Nicotiana sp.

<400> SEQUENCE: 13

```
atgggtttat cagctcgttt tcttgggtgt tttcttttga ttgttctctt tgttgattgt    60
gtggtgtttg ctgatgtcaa tggagctgaa gatgagaagt tcctccttgg acataaacgt   120
ccaacgtatg ggaaacgttt tggacgtggg atttatggta agggttttgg aggtggaggt   180
ggattaggag gtggtggtgg tctaggtggt ggtgcaggtg gtggtttagg tggaggaggt   240
ggattaggag gaggtggggg tctaggaggt ggtggtggac taggtggagg aggtggactt   300
ggtgggggtg gtggttttgg cggtggagcc ggaggaggac ttggtggagg tggtggactt   360
ggtggcggtg gtggagctgg tggtggagga ggcctaggtg gaggtgctgg aggtggtttt   420
ggcgcaggtg gaggtgctgg aggtggttta ggtggaggtg gaggcggagg ctttggtggt   480
ggtggaggtg gtggtattgg tggtggtgct ggtggagggt ttggagctgg tggaggtgtt   540
ggcggaggtg gtggtttagg aggtggaggt ggtggcggct ttggtggtgg aggcggcatt   600
ggcggtggta agcattga                                                 618
```

<210> SEQ ID NO 14
<211> LENGTH: 1200
<212> TYPE: DNA
<213> ORGANISM: Nicotiana sp.

<400> SEQUENCE: 14

```
atggcaacaa tggaaattgg gaatttaggt cttcgattta ggcctcaaat tgccataaat    60
ccaactagaa ataattattg caagcaattt cttggtcaga aaaagcaaaa caagaagaga   120
tttttagtat gttctgttgt ggaccaaaaa gaagctaaag tttcttcatt tagtaatgaa   180
gaaaatgccc taattgaagc tcttattggt attcaaggtc gtggtcgctc tgcttctcct   240
caacaacttc aagaggttga acgcgctgtt aaagttcttg aaggatcaga tggtgtttct   300
gaaccgacga gctcgagttt gattgagggg cggtggcagc tgatgttcac gactaggcca   360
gggtcagcat ctcctattca gaacttttt gttggggtag attcattcag tgtatttcaa   420
gaagtgttcc ttagaacgaa tgatccacgc gtatccaaca ttgtaaagtt ttctgaggca   480
ataggtgaac tgaaagtaga ggcacttgcg acgatcaaag atggaaaacg aattcttttc   540
caatttgata gagcagcctt ttcgttcaaa tttctacccg tcaaggttcc ataccctgta   600
ccttttcgac ttctgggaga tgaagctaag ggctggttag acacaacgta tttatctcca   660
tctgaaaatc tccgtatttc aagaggaaac aaggaaacta catttgtgct acaaaaggaa   720
gccgaaccaa gacaaaaatt gctttcatca atttcaacgg gtacaagtgt gaaaaggca   780
attgatgaat ttatttcctt gaaccaaaat gtagcaaatc ctgaattgga actacttgag   840
ggagagtggc aaatgatatg gagttcacag gttgaaacag atagttgggt cgagaatgct   900
ggcaatggtc tcatgggcat gcagattgtc aaaccaaatg acaattaaa gttcctggtt   960
gagatattct ttgggattag gttctccatg actggaaaat atgagaaatc cggtagtaac  1020
acgtacaatg ttataatgga tgatggagca ttcgtggctg gagtttatgg aattccagtt  1080
gaaatggaaa gcaagttcac catagaaata ctatatactg atgacaagat cagaatttca  1140
cggggctaca caaaattct cttcatccat gtacgcgtag atggatccaa aaagaagtga  1200
```

<210> SEQ ID NO 15
<211> LENGTH: 804
<212> TYPE: DNA
<213> ORGANISM: Nicotiana sp.

<400> SEQUENCE: 15

```
atggtgtccc tcatctccac tgcaattctc ccccacattt cttcctcatt catgggtaat      60
tcgagaaact tgaagtcaag ttcaaatatt tttccttcaa ttaaactcag taaccagaaa     120
actaccccaa gaacaagaac cccatttctt attttcaata aagctgcaag ctttgatgtt     180
tctgctgctg attcagcaaa ttctggagt gttagattta ggcttaataa cttgggccca      240
caaccagggg caacaaagaa taggaagaga aaggaagag gcatgcagc tggacaagga       300 ggtagttgtg gttttgggat gagaggtcaa aaatcaaggt ctggacctgg tgttagaaag     360
ggttttgaag gaggtcaaat gccactttat aggagacttc ctaagttgag aggaattgct    420
ggaggcatgt ctgctggact tccgaaatat gtacctgtga acttaaaaga catagaagag    480
gcaggatttc aagaagggga gagggtgtcg cttgaatccc tcaagcagaa gggtctaata    540
aatccatcag ggagagaaag gagacttccg ctaaagatct taggcgatgg tgaactaagc    600
gtgaagctca actttaaggc gcgcgccttt tcaacatcag caaggaaaa actagaggct     660 gctggttgtt cattaaccgt tctaccgggc agaagaagt gggtaaaacc atcagttgcc     720
aaaaaccttg ctagagctga ggaatatttt gccaagaaaa gagctgccgc tgcatctgaa    780
gcagctgacc cttcttctgc gtaa                                            804
```

<210> SEQ ID NO 16
<211> LENGTH: 183
<212> TYPE: DNA
<213> ORGANISM: Nicotiana sp.

<400> SEQUENCE: 16

```
atggagagtg tggaatttgg aatgccaatc accaatcaga atatcaaagc agttattttt     60
gatatgttca tggcaggagc ggaaacatca tccacaacac ttatttgggt aatggcagaa    120
ttgataagaa atccaagcgt catggctaaa gcacaacgtg aagttagagg atcggagtcc    180
taa                                                                  183
```

<210> SEQ ID NO 17
<211> LENGTH: 471
<212> TYPE: DNA
<213> ORGANISM: Nicotiana sp.

<400> SEQUENCE: 17

```
atgggtcatg actgccatgg gattgagaac aagaaatcag ttgctgtagt tggcctgaag     60
atcctaatta atcataagct ttctcaggcc aaagcaaatc ctaataatgt ttcaagattc    120
actagagtca aacccatctt ccacacgaat tatactgaat ctagcagcag tgaacaaaat    180
tcttgcttcc tcaaatattg ttgcctttgc aacaagactc tgaggcttga caaacaagtt    240
tacatgtata agggtgatat gggtttctgc agtttagagt gtaggcacag gcagattat     300 ttggatgaaa ttaagaaat tgagaattgt actaagaaaa tgttgcgatc ttttcgccaa    360
tgtggagacg tggtcggtg cagtgagact tcgacattat tggaggagta ccatcagcgg    420 cgcaaccct tgtcatattc caagaatcga actatattca cattctcata a             471
```

<210> SEQ ID NO 18
<211> LENGTH: 170
<212> TYPE: PRT
<213> ORGANISM: Nicotiana sp.

<400> SEQUENCE: 18

```
Met Glu Glu Val Trp Lys Asn Ile Asn Leu Ser Ser Leu Asn Asp Asp
1               5                   10                  15
```

Thr Thr Thr Ser Ser Arg Asp His Ile Asp Pro Gln Gln Asn Ile Ser
            20                  25                  30

Asn Ser Thr Asn Phe Gly Gly Met Ile Leu Gln Asp Phe Leu Ala Arg
        35                  40                  45

Pro Phe Ala Asn Asn Pro Lys Thr Ala Ala Lys Gly Tyr Val Pro Pro
    50                  55                  60

Ile Phe Pro Pro Ala Ala Ala Ala Val Thr Val Leu Thr Leu Asn
65                  70                  75                  80

Ser Gly Pro Gly Leu His Phe Phe Gly Asn Leu Arg Gln Asn Ser Ser
                85                  90                  95

Ser Glu Gln Gln Lys Ser Ile Ser Asn Thr Ser Phe Glu Asp Leu Ala
            100                 105                 110

Ser Pro Val Gly Gly Asn Thr Asn Gly Arg Lys Arg Cys Ser Glu Ser
        115                 120                 125

Asp Asp Asn Asn Ser Ser Asp Gln Lys Asn Lys Arg Met Ile Lys Asn
    130                 135                 140

Arg Glu Ser Ala Ala Arg Ser Arg Ala Arg Lys Gln Glu Ser Ala Ala
145                 150                 155                 160

Ser Leu Phe Thr Leu Pro Thr Cys Val Phe
                165                 170

<210> SEQ ID NO 19
<211> LENGTH: 182
<212> TYPE: PRT
<213> ORGANISM: Nicotiana sp.

<400> SEQUENCE: 19

Met Glu Asn Gln Ser Met Pro Phe Leu Gly Ser Thr Ser Cys Val Arg
1               5                   10                  15

Thr Ile Ser Ser Asp Ser Phe Ser Asn Ser Ile Asn Ile Gly Tyr Asn
            20                  25                  30

Ser Met Asn Gly Trp Thr Ser Gly Leu Lys Thr Glu Ile Ser Asn Ser
        35                  40                  45

Thr Ala Arg Glu Gln Asn Ile Thr Asn Ile Lys Asn Ser Leu Met Gly
    50                  55                  60

Val Val Ser Ser Glu Ile His Thr Thr Asn Ile Ile Ser Ser Leu Lys
65                  70                  75                  80

Lys Lys Gly Asp Lys Lys Ile Lys Lys Pro Arg Phe Ala Phe Gln Thr
                85                  90                  95

Arg Ser Gln Val Asp Ile Leu Asp Asp Gly Tyr Arg Trp Arg Lys Tyr
            100                 105                 110

Gly Gln Lys Ala Val Lys Asn Asn Tyr Pro Arg Ser Tyr Tyr Lys
        115                 120                 125

Cys Thr His Gln Gly Cys Asn Val Lys Lys Gln Val Gln Arg Leu Ser
    130                 135                 140

Lys Asp Glu Gly Val Val Val Thr Thr Tyr Glu Gly Met His Thr His
145                 150                 155                 160

Pro Ile Asp Lys Pro Thr Asp Asn Phe Glu Gln Ile Leu His Gln Met
                165                 170                 175

His Ile Ile Pro Pro His
            180

<210> SEQ ID NO 20
<211> LENGTH: 227
<212> TYPE: PRT
<213> ORGANISM: Nicotiana sp.

<400> SEQUENCE: 20

```
Met Asp Tyr Ala Ser Leu Glu Thr Arg Thr His Asp Pro Leu Asn Tyr
1               5                   10                  15

Ile Asn Asn Ser Gln Val Asn Lys Arg Leu Pro Lys Arg Ile Leu
            20                  25                  30

Gly Thr Thr Asp Asn Asn Ile Pro Asp Lys Lys Asp Glu Thr Ala Ala
            35                  40                  45

Ala Ala Ala Thr Pro Asp Asp Phe Lys Leu Thr Arg Ile Met His Arg
50                  55                  60

Asp Ile Glu Arg Gln Arg Arg Glu Met Ser Ala Leu Tyr Ser Ser
65                  70                  75                  80

Leu Arg Ser Leu Leu Pro Leu Gln Tyr Val Lys Gly Lys Arg Ser Val
                85                  90                  95

Ser Asp His Met His Glu Ala Val Asn Tyr Ile Lys Glu Met Gln Ala
            100                 105                 110

Asn Met Lys Glu Leu Glu Lys Arg Arg Asp Leu Leu Ile Lys Ser Ser
            115                 120                 125

Leu Pro Asn Ser Ile Arg Ser Asn Asn Phe Thr Val Ser Pro Asp Cys
130                 135                 140

Val Thr Val Ser Pro Cys Leu Gln Gly Gly Ile Glu Ile Leu Ile Ser
145                 150                 155                 160

Val Asp Cys Lys Ala Gln Ser Phe Pro Leu Ser Arg Val Leu Arg Glu
                165                 170                 175

Leu Leu Lys Gln Gly Ile Asn Val Val Ser Cys Val Ser Ala Lys Val
            180                 185                 190

Asn Gln Arg Ser Leu His Thr Ile Gln Ile Glu Val Cys Asp Met Asn
            195                 200                 205

Asn Ile Asp His Gln Ala Leu Gln Gln Lys Val Ile Asp Leu Ile Asn
210                 215                 220

Val Asp Leu
225
```

<210> SEQ ID NO 21
<211> LENGTH: 319
<212> TYPE: PRT
<213> ORGANISM: Nicotiana sp.

<400> SEQUENCE: 21

```
Met Glu Leu Val Glu Asn Ile Ala Ala Asn Thr Asn Ile Lys Ala Glu
1               5                   10                  15

Asp Glu Glu Glu Met Met Gln Leu Pro Gly Phe Arg Phe His Pro Thr
            20                  25                  30

Asp Glu Glu Leu Val Ser Phe Tyr Leu Lys Arg Lys Val Glu Asn Lys
            35                  40                  45

Lys Ile Lys Ile Asp Leu Ile Lys Glu Val Asp Ile Tyr Lys His Asp
        50                  55                  60

Pro Trp Asp Leu Pro Lys Gly Asn Thr Val Gly Asp Asn Cys Lys Glu
65                  70                  75                  80

Trp Tyr Phe Phe Ser Met Arg Gly Arg Lys Tyr Arg Asn Ser Val Arg
                85                  90                  95

Pro Asn Arg Val Thr Gly Ser Gly Phe Trp Lys Ala Thr Gly Ile Asp
            100                 105                 110

Lys Pro Ile Tyr Ser Ser Thr Thr Thr Ser Gln Ser Thr Asp Arg
            115                 120                 125
```

```
Glu Cys Ile Gly Leu Lys Lys Ser Leu Val Tyr Tyr Arg Gly Ser Ala
            130                 135                 140

Gly Lys Gly Thr Lys Thr Asp Trp Met Met His Glu Phe Arg Leu Pro
145                 150                 155                 160

Pro Asn Trp Lys Thr Ser Asn Gln Gln Leu Pro Asn Pro Lys Asn Ile
                165                 170                 175

Ile Pro Glu Ala Glu Val Trp Thr Leu Cys Arg Ile Phe Lys Arg Thr
            180                 185                 190

Ser Asn Tyr Lys Arg Phe Thr Pro Asp Trp Lys Gln Pro Val Ile Lys
                195                 200                 205

Gln Ser Phe Gly Asp Ala Ser Ser Lys Ala Cys Ser Leu Gln Ser Glu
    210                 215                 220

Thr Ser Asp Asp His Ser Ile Asn Ile Asn Phe Asn Lys Met Glu Phe
225                 230                 235                 240

Pro His Lys Lys Asn Asn Thr Ala Thr Gly Gly Asn Tyr Gln Val Asp
                245                 250                 255

Gln Lys Thr Thr His Tyr Gln Asn Ser Gln Pro Ile Ile Thr Met Pro
            260                 265                 270

Gln Ser Ser Ile Thr Ser Ser Asn Ser Ser Phe Trp Asn Thr Ser Ala
    275                 280                 285

Glu Glu Glu Tyr Leu Phe Ser Asp Gly Asn Trp Asp Glu Leu Lys Ser
290                 295                 300

Val Val Asp Leu Ala Ile Asp Pro Arg Ser Leu Phe Gly Phe Arg
305                 310                 315

<210> SEQ ID NO 22
<211> LENGTH: 751
<212> TYPE: PRT
<213> ORGANISM: Nicotiana sp.

<400> SEQUENCE: 22

Met Ala Pro Lys Thr Pro Ser Leu Pro Leu Tyr Glu Ile Lys Tyr Arg
1               5                   10                  15

Lys Asn Ile Ile Ser Arg Gly Ile Glu Leu Phe Ile Leu Phe Leu Leu
            20                  25                  30

Phe Ser Leu Leu Ala Tyr Arg Leu Leu Ser Leu Lys Asn His Gly Phe
        35                  40                  45

Ser Leu Pro Phe Phe Leu Ala Leu Ile Cys Glu Ser Trp Phe Thr Phe
    50                  55                  60

Leu Trp Ile Leu Thr Ile Asn Ala Lys Trp Asn Gln Val Glu Pro Lys
65                  70                  75                  80

Thr Tyr Pro Leu Arg Leu Leu Glu Arg Thr Ala Glu Phe Pro Ala Val
                85                  90                  95

Asp Met Phe Ile Thr Thr Ala Asp Pro Ile Leu Glu Pro Pro Leu Ile
            100                 105                 110

Thr Val Asn Thr Met Leu Ser Leu Leu Ala Val Asp Tyr Pro Ala Asn
        115                 120                 125

Lys Leu Ala Cys Tyr Val Ser Asp Asp Gly Ala Ser Pro Ile Thr Tyr
    130                 135                 140

Tyr Ser Leu Val Glu Ala Ser Lys Phe Ala Lys Leu Trp Val Pro Phe
145                 150                 155                 160

Cys Lys Lys Tyr Asn Ile Ala Leu Arg Ala Pro Phe Arg Tyr Phe Ser
                165                 170                 175

Ala Asn Ser Leu Pro Pro Gln Asp Thr Ser Gln Gly Phe Pro Glu Asp
```

```
                180                 185                 190
Trp Lys Arg Met Lys Asp Glu Tyr Lys Gln Leu Cys Glu Lys Ile Glu
            195                 200                 205
Asp Ala Ser Thr Gln Glu Ala Glu Ala Cys Asp Phe Ser Gly Asp Phe
        210                 215                 220
Ala Val Phe Ser Lys Ile Glu Arg Lys Asn His Pro Thr Ile Ile Lys
225                 230                 235                 240
Val Ile Leu Glu Asn Lys Glu Gly Ile Ala Asp Gly Leu Pro His Leu
                245                 250                 255
Val Tyr Ile Ser Arg Glu Lys Arg Pro Lys His Pro His Phe Lys
            260                 265                 270
Ala Gly Ala Met Asn Val Leu Thr Arg Val Ser Gly Leu Met Thr Asn
        275                 280                 285
Ala Pro Phe Met Leu Asn Val Asp Cys Asp Met Tyr Ala Asn Asn Pro
290                 295                 300
Gln Val Val Gln His Ala Met Cys Tyr Phe Leu Gly Ala Lys Asp Glu
305                 310                 315                 320
Lys Asp Cys Gly Phe Val Gln Phe Pro Gln Tyr Phe Tyr Asp Gly Leu
                325                 330                 335
Lys Asp Asp Pro Tyr Gly Asn Gln Leu Lys Val Leu His Glu Tyr Leu
            340                 345                 350
Gly Arg Gly Phe Ala Gly Ile Gln Gly Pro Phe Tyr Gln Gly Thr Gly
        355                 360                 365
Cys Phe His Arg Arg Lys Ile Ile Tyr Gly Leu Ser Pro Asn Glu Lys
    370                 375                 380
Ile Asn Thr Gly Glu Leu Arg Asp Glu Tyr Leu Gln Lys Thr Tyr Gly
385                 390                 395                 400
Lys Ser Gln Lys Leu Leu Ala Ser Val Ala Gln Thr Leu Ser Ala Gly
                405                 410                 415
Ser Asn Asn Ile Glu Gln Val Asn Ser Asp Ser Leu Ser Ser Phe Ile
            420                 425                 430
Glu Glu Ala Gln Gln Ile Gly Ser Cys Gly Tyr Glu Phe Gly Thr Ala
        435                 440                 445
Trp Gly Gln Lys Leu Gly Trp Leu Tyr Gly Cys Ala Thr Glu Asp Val
    450                 455                 460
Leu Thr Gly Leu Leu Ile Gln Gly Lys Gly Trp Arg Ser Ala Tyr Cys
465                 470                 475                 480
Ala Pro Asp Pro Pro Ala Phe Leu Gly Thr Ala Pro Ser Gly Gly Pro
                485                 490                 495
Ala Ser Met Thr Gln Gln Lys Arg Trp Ala Asn Gly Leu Phe Glu Ile
            500                 505                 510
Leu Phe Phe Ser Lys Ser Pro Ile Ile Gly Thr Leu Phe Gly Lys Leu
        515                 520                 525
Gln Leu Arg Gln Cys Met Ala Tyr Leu Tyr Ile Gln Leu Trp Ala Leu
    530                 535                 540
Arg Ser Ile Phe Glu Val Cys Tyr Ala Ile Leu Pro Pro Tyr Cys Leu
545                 550                 555                 560
Ile Thr Asn Ser Ser Phe Leu Pro Lys Ala Asn Glu Pro Ser Met Val
                565                 570                 575
Ile Pro Ala Ser Ile Phe Ile Ile Tyr Asn Leu Tyr Gly Leu Ser Glu
            580                 585                 590
Tyr Val Arg Ala Asn Glu Pro Ile Lys Ala Trp Leu Asn Asn Gln Arg
        595                 600                 605
```

```
Met Trp Arg Val Asn Ala Met Thr Ala Trp Leu Phe Gly Ile Leu Gly
            610                 615                 620

Ala Thr Thr Lys Leu Leu Gly Ile Ser Glu Thr Ala Phe Glu Val Thr
625                 630                 635                 640

Lys Lys Asp Gln Gly Asn Asp Gly Asp Thr Asn Asn Ser Asn Ile
                    645                 650                 655

Gly Arg Phe Thr Phe Asp Asp Ser Pro Ile Phe Val Pro Gly Thr Ala
                660                 665                 670

Ile Leu Leu Leu Asn Leu Ser Ser Leu Phe Ile Gly Met Leu Asp Phe
                675                 680                 685

Lys Gln Gly Lys Asp Cys Glu Trp Gly Leu Gly Glu Val Ile Cys Ile
            690                 695                 700

Met Trp Val Leu Phe Ile Phe Trp Ser Phe Leu Lys Gly Leu Phe Ala
705                 710                 715                 720

Lys Gly Lys Tyr Gly Ile Pro Ala Thr Thr Ile Leu Lys Ser Gly Ala
                725                 730                 735

Leu Ala Leu Leu Leu Val His Leu Phe Lys Phe Thr Asn Lys Leu
                740                 745                 750

<210> SEQ ID NO 23
<211> LENGTH: 158
<212> TYPE: PRT
<213> ORGANISM: Nicotiana sp.

<400> SEQUENCE: 23

Met Asn Glu Asn Gly Ser Thr Lys Leu Leu Gln Ala Gln Thr Gln Thr
1               5                   10                  15

Trp Asn His Ile Tyr Asn Phe Val Ser Ser Ala Ala Lys Cys Ala
                20                  25                  30

Val Gln Leu Gly Ile Pro Asp Val Leu Leu Ala Pro Leu Lys Ser
            35                  40                  45

Tyr Leu Leu Asn Phe Phe Met Val Lys Gln Trp Ile Leu His Asn Trp
50                  55                  60

Gly Asp Glu Asp Cys Val Lys Ile Leu Lys Lys Cys Lys Glu Ser Ile
65                  70                  75                  80

Pro Ser Arg Glu Lys Gly Gly Lys Val Ile Ile Gly Ile Val Leu
                85                  90                  95

Glu Asn Pro Lys Glu Lys Asp Asp Ser Val Arg Ala Gln His Asn Met
                100                 105                 110

Asp Leu Val Met Met Val Leu Phe Gly Ala Lys Glu Arg Thr Lys Lys
            115                 120                 125

Glu Trp Glu Lys Leu Phe Thr Glu Ala Gly Phe Asn Glu Tyr Glu Ile
130                 135                 140

Thr Pro Thr Leu Gly Thr Arg Ser Leu Ile Glu Ile Tyr Pro
145                 150                 155

<210> SEQ ID NO 24
<211> LENGTH: 201
<212> TYPE: PRT
<213> ORGANISM: Nicotiana sp.

<400> SEQUENCE: 24

Met Asp Arg Lys Ile Val Phe Leu Val Ser Phe Leu Cys Ile Val Val
1               5                   10                  15

Ala Ser Val Thr Gly Gln Thr Pro Ala Ala Ala Pro Ala Lys Ala Pro
                20                  25                  30
```

Val Gly Ala Lys Ala Ser Thr Pro Ala Ala Pro Thr Lys Pro
        35                  40                  45

Lys Thr Pro Ala Pro Ala Thr Ala Pro Ala Ser Ala Pro Pro Thr Ala
50                  55                  60

Val Ser Thr Pro Pro Ala Ala Ala Pro Ala Thr Ala Pro Thr Thr Pro
65                  70                  75                  80

Val Val Thr Pro Pro Val Ser Ala Pro Ala Lys Thr Pro Ala Ser
                    85                  90                  95

Ser Pro Pro Ala Ala Val Pro Val Ser Ser Pro Pro Ala Val Thr
                100                 105                 110

Pro Val Gln Ser Pro Pro Ala Pro Ala Pro Val Ala Ala Thr Pro Pro
                115                 120                 125

Ala Ala Ser Ala Pro Pro Ala Pro Val Pro Val Ser Ala Ser Ser Pro
130                 135                 140

Ala Pro Ser Pro Asp Met Met Ser Pro Pro Ala Pro Pro Thr Glu Ala
145                 150                 155                 160

Pro Gly Pro Ser Met Asp Ser Asp Ser Pro Ser Pro Ser Leu Asn Asp
                165                 170                 175

Glu Ser Gly Ala Glu Lys Leu Lys Met Leu Gly Ser Leu Val Ala Gly
            180                 185                 190

Trp Ala Val Met Ser Trp Phe Leu Phe
            195                 200

<210> SEQ ID NO 25
<211> LENGTH: 513
<212> TYPE: PRT
<213> ORGANISM: Nicotiana sp.

<400> SEQUENCE: 25

Met Glu Lys Glu Lys Lys Ile Asp Met Glu Glu Lys His Glu Lys Glu
1               5                   10                  15

Leu Lys Glu Lys Glu Lys Lys Asp Lys Val Lys Asn Thr Gly Ser Glu
                20                  25                  30

Glu Glu Ser Glu Glu Thr Glu Asp Glu Lys Asp Gly Ala Thr Lys Asn
            35                  40                  45

Val Lys Glu Lys Lys Tyr Lys Lys Glu Lys Lys Glu Lys Lys Asp Lys
50                  55                  60

Glu Lys Lys Asp Lys Ser Lys Glu Glu Glu Ser Glu Glu Glu Thr Glu
65                  70                  75                  80

Glu Glu Lys Asp Asp Gly Lys Gly Lys Lys Asp Lys Lys Lys Lys His
                85                  90                  95

Lys Thr Asp Met Lys Glu Lys Lys Asp Lys Glu Met Lys Asp Lys Ser
                100                 105                 110

Lys His Glu Ser Glu Lys Glu Asp Ser Lys Glu Ile Glu Glu Glu Lys
            115                 120                 125

Asp Asp Gly Glu Gly Glu Lys Lys Asp Lys Glu Lys Lys Leu Lys Lys
130                 135                 140

Gly Lys Lys Asp Arg Lys Glu Lys Glu Lys Lys Asp Lys Ser Ile Glu
145                 150                 155                 160

Glu Ser Lys Glu Glu Lys Asp Asp Asp Lys Gly Glu Lys Lys Asp Lys
                165                 170                 175

Glu Gln Lys Asp Lys Lys Glu Lys Lys Asn Lys Glu Glu Lys Gly Lys
            180                 185                 190

Ser Lys Gly Glu Ser Glu Glu Glu Thr Glu Glu Glu Lys Asp Asp Glu

```
                195                 200                 205
Lys Gly Lys Asn Lys Glu Ser Asp Glu Glu Asp Glu Arg Gln Thr Glu
210                 215                 220
Glu Glu Glu Asn Asp Glu Lys Gly Val Lys Lys Asp Lys Glu Lys Lys
225                 230                 235                 240
Asn Lys Glu Lys Lys Glu Lys Lys Asp Asn Glu Lys Lys Asp Lys Ser
                245                 250                 255
Lys Glu Glu Thr Glu Glu Glu Lys Asp Asp Glu Lys Gly Glu Lys Lys
                260                 265                 270
Asp Lys Glu Lys Lys Cys Lys Lys Asn Lys Lys Glu Lys Lys Asp Lys
                275                 280                 285
Glu Thr Lys Asp Lys Ser Lys Glu Val Ser Asp Glu Glu Glu Lys
                290                 295                 300
Asp Asp Glu Glu Gly Lys Lys Asp Lys Lys Lys His Asn Lys
305                 310                 315                 320
Asp Lys Lys Glu Thr Lys Asp Lys Glu Lys Lys Tyr Lys Ser Lys Glu
                325                 330                 335
Glu Ser Glu Glu Glu Asp Lys Lys Glu Thr Glu Glu Lys Asp Asp
                340                 345                 350
Asp Glu Glu Gly Gln Lys Lys Glu Lys Glu Lys Lys Asn Lys Lys Asp
                355                 360                 365
Lys Lys Glu Lys Lys Asp Lys Lys Lys Val Lys Ser Lys Glu Glu
                370                 375                 380
Ser Asp Glu Glu Asp Lys Gln Asp Lys Val Asn Glu Val Glu Val Ala
385                 390                 395                 400
Thr Arg Glu Ile Lys Ile Glu Asp Asp Lys Lys Ile Ser Asp Gly Glu
                405                 410                 415
Ala Asp Glu Lys Gly Lys Arg Lys Glu Lys Gly Lys Asp Ser Lys Asp
                420                 425                 430
Glu Lys Gln Lys Asp Ala Lys Lys Asp Lys Ala Glu Lys Thr Arg Lys
                435                 440                 445
Leu Glu Asp Lys Tyr Lys Ser Asn Gly Lys Leu Lys Ser Lys Leu Glu
                450                 455                 460
Lys Ile Asn Ala Lys Leu Glu Ala Leu Gln Gln Lys Lys Ala Asp Ile
465                 470                 475                 480
Met Lys Thr Ile Lys Glu Ala Glu Asp Lys Asn Leu Ala Val Val Glu
                485                 490                 495
Ser Pro Lys Glu Ala Asp Leu Lys Ala His Asp Gly Val Met Thr Glu
                500                 505                 510
Gln

<210> SEQ ID NO 26
<211> LENGTH: 334
<212> TYPE: PRT
<213> ORGANISM: Nicotiana sp.

<400> SEQUENCE: 26

Met Ser Gly Gln Asn Asp Glu Ile Ala Leu Ile Asp Pro Asn Val Asp
1               5                   10                  15

Pro Tyr Arg Tyr Leu Gly Ile Arg Arg Asn Thr Asp Ser Ile Ile
                20                  25                  30

Arg Leu Pro Glu Ser Thr Leu Pro Phe Ala Thr Thr Ile Pro Asp Leu
                35                  40                  45

Ser Leu Val Phe Thr Lys Asp Leu Ile Ile Asn Pro Thr Lys Asn Thr
```

```
                50                  55                  60
Leu Ala Arg Ile Val Ile Pro Arg Lys Val Leu Asn Ser Asn Asn Ile
 65                  70                  75                  80

Asn Thr Thr Thr Lys Leu Pro Leu Ile Val Tyr Phe His Gly Gly Gly
                    85                  90                  95

Phe Val Ile Ala Ala Ser Val Asp Thr Pro Phe Leu Gln Thr Phe Tyr
                100                 105                 110

Glu Thr Leu Val Ala Glu Ile Pro Ala Ile Val Ser Val Asp Tyr
            115                 120                 125

Arg Tyr Ala Pro Glu Asn Arg Leu Pro Ala Ala Tyr Asp Asp Cys Ile
            130                 135                 140

Glu Ser Leu His Trp Ile Lys Asn Asn Pro Asp Glu Leu Leu Lys Lys
145                 150                 155                 160

Tyr Ala Asp Phe Ser Lys Cys Phe Leu Met Gly Thr Ser Ala Gly Gly
                165                 170                 175

Asn Ile Thr Tyr His Val Gly Leu Gln Val Ala Gly Ile Ser Glu Tyr
                180                 185                 190

Leu Lys Pro Leu Glu Ile Lys Gly Leu Ile Leu His His Ala Phe Phe
            195                 200                 205

Gly Gly Asn Glu Arg Thr Gln Ser Glu Leu Arg Leu Ala Phe Asn Lys
            210                 215                 220

Ile Leu Ser Leu Asn Val Ser Asp Ile Met Trp Glu Leu Gly Leu Pro
225                 230                 235                 240

Ile Gly Ser Asp Arg Asp His Pro Tyr Cys Asn Pro Met Gly Glu Ile
                245                 250                 255

Lys Ser Asn Asp Asn Leu Phe Asp Gln Val Lys Ile Gln Gly Trp Lys
                260                 265                 270

Val Leu Leu Ile Gly Cys Asp Gly Asp Pro Leu Ile Asp Arg Gln Thr
            275                 280                 285

Glu Leu Ser Lys Met Leu Lys Glu Lys Gly Val Gln Val Val Asp Ile
            290                 295                 300

Phe Ser Glu Gly Gly Phe His Ala Cys Glu Phe Phe Asp Pro Asn Lys
305                 310                 315                 320

Leu Lys Glu Leu Ala Val Val Ile Met Glu Phe Val Arg Gly
                325                 330

<210> SEQ ID NO 27
<211> LENGTH: 386
<212> TYPE: PRT
<213> ORGANISM: Nicotiana sp.

<400> SEQUENCE: 27

Met Gly Ser Tyr Lys Glu Glu Lys Thr Asp Gln Gln Pro Lys Trp
 1               5                  10                  15

Leu Trp Val Asn Gly Pro Ile Ile Val Gly Ala Gly Pro Ser Gly Leu
                20                  25                  30

Ala Val Ser Ala Cys Leu Lys Glu Asn Gly Val Pro Ser Leu Ile Leu
            35                  40                  45

Glu Arg Ser Asp Cys Ile Ala Ser Leu Trp Gln Gln Lys Thr Tyr Asp
            50                  55                  60

Arg Leu Lys Leu His Leu Pro Lys Gln Phe Cys Gln Leu Pro Leu Phe
 65                  70                  75                  80

Gly Phe Pro Glu Asn Phe Pro Lys Tyr Pro Ser Lys Lys Leu Phe Ile
                85                  90                  95
```

```
Ser Tyr Leu Glu Asp Tyr Ala Lys His Phe Gly Ile Val Pro Lys Phe
            100                 105                 110

Lys Gln Ser Val Lys Val Ala Glu Phe Asp His Val Ser Gly Phe Trp
        115                 120                 125

Lys Val Glu Thr Gln Asp Phe Leu Tyr Leu Ser Lys Trp Leu Ile Val
    130                 135                 140

Ala Thr Gly Glu Asn Ala Glu Pro Val Ile Pro Glu Ile Gln Gly Ile
145                 150                 155                 160

Asp Lys Phe Lys Gly Ala Val Leu His Thr Ser Val Tyr Lys Ser Gly
                165                 170                 175

Thr Glu Phe Asn Asn Gln Arg Val Leu Val Ile Gly Cys Gly Asn Ser
            180                 185                 190

Gly Met Glu Val Ser Leu Asp Leu Cys Arg His Asn Ala Ile Pro His
        195                 200                 205

Met Val Val Arg Asn Ser Val His Ile Leu Pro Arg Glu Met Leu Gly
    210                 215                 220

Ile Ser Thr Phe Ser Ile Ala Met Ala Leu Leu Lys Trp Leu Pro Ile
225                 230                 235                 240

Arg Val Val Asp Lys Leu Leu Leu Leu Val Ala Asn Leu Thr Leu Gly
                245                 250                 255

Ser Thr Asp Lys Leu Gly Leu Arg Arg Pro Lys Thr Gly Pro Leu Glu
            260                 265                 270

Leu Lys Asn Ala Thr Gly Lys Thr Pro Val Leu Asp Val Gly Ala Leu
        275                 280                 285

Ser Gln Ile Arg Asn Gly Lys Ile Gln Ile Met His Gly Val Lys Glu
    290                 295                 300

Ile Thr Lys Ile Gly Ala Lys Phe Ile Asp Gly Lys Glu Gly Glu Tyr
305                 310                 315                 320

Asp Ser Ile Ile Leu Ala Thr Gly Tyr Lys Ser Asn Val Pro Ser Trp
                325                 330                 335

Leu Lys Gly Thr Asp Phe Phe Thr Glu Gln Gly Met Pro Lys Thr Pro
            340                 345                 350

Phe Pro Asn Gly Trp Lys Gly Glu Asn Gly Leu Tyr Thr Val Gly Phe
        355                 360                 365

Thr Arg Arg Gly Leu Leu Gly Thr Ala Asn Asp Ala Lys Lys Leu Pro
    370                 375                 380

Gly Thr
385

<210> SEQ ID NO 28
<211> LENGTH: 475
<212> TYPE: PRT
<213> ORGANISM: Nicotiana sp.

<400> SEQUENCE: 28

Met Asp Ser Ser Gln Leu His Val Ala Ile Val Ser Ser Pro Gly Met
1               5                   10                  15

Gly His Leu Ile Pro Val Leu Val Leu Gly Asn Gln Leu Ala Thr Tyr
            20                  25                  30

His Asn Ile Lys Ile Thr Met Leu Ala Ile Thr Thr Ser Ser Ser Ser
        35                  40                  45

Ala Glu Thr Glu Phe Leu Lys Lys Ser Thr Leu Thr Asn Glu Lys Lys
    50                  55                  60

Thr Ile Glu Ile Ile Pro Val Pro Ser Asn Asp Ile Ser His Leu Ile
65                  70                  75                  80
```

```
Asn Ser Ser Thr Lys Val Phe Thr Lys Leu Arg Leu Val Arg Glu
                 85                  90                  95

Thr Leu Pro Lys Ile Arg Ser Ala Ile Ala Ser Met Thr His Arg Pro
            100                 105                 110

Asp Ala Leu Ile Val Asp Ile Phe Gly Thr Gln Ile Leu Pro Ile Ala
            115                 120                 125

Glu Glu Phe Asn Ile Pro Lys Tyr Ala Tyr His Leu Thr Thr Ala Trp
130                 135                 140

Thr Leu Ala Leu Ala Ile Tyr Cys Gln Val Leu Glu Lys Glu Ile Glu
145                 150                 155                 160

Gly Glu Tyr Val Asp Leu Lys Glu Pro Leu Lys Ile Pro Gly Cys Lys
                165                 170                 175

Ala Leu Arg Pro Asp Asn Val Leu Asp Gln Leu Leu Asp Arg Ser Asp
            180                 185                 190

Gln Gln Tyr Glu Glu Tyr Val Lys Pro Gly Met Glu Tyr Thr Asp Phe
            195                 200                 205

Asp Gly Ile Leu Ile Asn Thr Trp Glu Asp Leu Glu Pro Glu Thr Ile
            210                 215                 220

Asn Ala Leu Lys Tyr Asn Glu Lys Leu Arg Leu Leu Lys Val Pro
225                 230                 235                 240

Val Phe Pro Ile Gly Pro Leu Arg Arg Lys Val Glu Thr Thr Ser Asn
                245                 250                 255

Asp Glu Val Ile Gln Trp Leu Asp Lys Gln Asn Asn Glu Ser Val Leu
            260                 265                 270

Phe Ala Ser Phe Gly Ser Gly Gly Thr Leu Ser Thr Lys Gln Met Thr
            275                 280                 285

Glu Leu Ala Trp Gly Leu Glu Leu Ser Gln Gln Lys Phe Val Trp Val
290                 295                 300

Val Arg Pro Pro Ser Asp Gly Asp Ala Asp Ser Ala Tyr Leu Asn Ser
305                 310                 315                 320

Thr Gly Lys Glu Thr Arg Gly Met Ser Glu Tyr Leu Pro Glu Gly Phe
                325                 330                 335

Leu Thr Arg Thr Lys Asp Met Gly Leu Val Val Pro Met Trp Ala Asn
            340                 345                 350

Gln Val Glu Ile Leu Gly His Ser Ser Leu Gly Gly Phe Leu Thr His
            355                 360                 365

Cys Gly Trp Asn Ser Thr Met Glu Ser Leu Thr Asn Gly Val Pro Met
370                 375                 380

Ile Ala Trp Pro Leu His Ala Glu Gln Lys Met Asn Ala Ala Met Leu
385                 390                 395                 400

Thr Glu Glu Leu Gly Val Ala Ile Arg Pro Ala Val Leu Pro Thr Lys
                405                 410                 415

Lys Leu Val Lys Arg Glu Glu Ile Gln Gly Met Val Arg Ile Leu Met
            420                 425                 430

Gln Thr Lys Glu Gly Lys Pro Ile Glu Lys Ala Lys Leu Lys
            435                 440                 445

Met Ser Ala Glu Asn Ala Leu Ser Glu Gly Gly Ser Ser Tyr Asn Ser
450                 455                 460

Ile Cys Glu Leu Val Lys Asp Ile Gln Ser Arg
465                 470                 475

<210> SEQ ID NO 29
<211> LENGTH: 184
```

<212> TYPE: PRT
<213> ORGANISM: Nicotiana sp.

<400> SEQUENCE: 29

```
Met Ala Ser Phe His Ser Leu Lys Thr Leu Ala Ile Val Ala Leu Ala
1               5                   10                  15

Ile Ser Ser Phe Val Gln Val Thr Leu Gly Gly Ile Ala Cys Glu Asn
            20                  25                  30

Leu Asn Glu Asp Ser Cys Ala Phe Ala Ile Ser Ser Asn Gly Lys Arg
        35                  40                  45

Cys Val Leu Glu Lys His Leu Arg Arg Ser Gly Glu Gly Tyr Thr
    50                  55                  60

Cys Arg Thr Ser Glu Ile Glu Ala Asp Lys Leu Lys Asp Trp Ile Glu
65                  70                  75                  80

Thr Asp Glu Cys Ile Glu Ala Cys Gly Val Asp Arg Asn Ala Leu Gly
                85                  90                  95

Ile Ser Ser Asp Ala Leu Leu Glu Ser Arg Phe Thr Asn Lys Leu Cys
            100                 105                 110

Ser Pro Ala Cys Tyr Lys His Cys Pro Asn Ile Val Asp Leu Tyr Phe
        115                 120                 125

Asn Leu Ala Ala Gly Glu Gly Val Tyr Leu Pro Lys Leu Cys Ala Glu
    130                 135                 140

Gln Gly Lys Ser Ala Arg Arg Glu Ile Ala Glu Ile Arg Ser Ser Gly
145                 150                 155                 160

Leu Val Ala Pro Ala Pro Glu Ser Glu Val Lys Pro Ser Asn Phe Met
                165                 170                 175

Ile Ala Pro Ala Met Pro Pro Phe
            180
```

<210> SEQ ID NO 30
<211> LENGTH: 205
<212> TYPE: PRT
<213> ORGANISM: Nicotiana sp.

<400> SEQUENCE: 30

```
Met Gly Leu Ser Ala Arg Phe Leu Gly Cys Phe Leu Leu Ile Val Leu
1               5                   10                  15

Phe Val Asp Cys Val Val Phe Ala Asp Val Asn Gly Ala Glu Asp Glu
            20                  25                  30

Lys Phe Leu Leu Gly His Lys Arg Pro Thr Tyr Gly Lys Arg Phe Gly
        35                  40                  45

Arg Gly Ile Tyr Gly Lys Gly Phe Gly Gly Gly Gly Leu Gly Gly
    50                  55                  60

Gly Gly Gly Leu Gly Gly Gly Ala Gly Gly Leu Gly Gly Gly
65                  70                  75                  80

Gly Leu Gly Gly Gly Gly Leu Gly Gly Gly Gly Leu Gly Gly
                85                  90                  95

Gly Gly Gly Leu Gly Gly Gly Gly Phe Gly Gly Ala Gly Gly
            100                 105                 110

Gly Leu Gly Gly Gly Gly Leu Gly Gly Gly Gly Ala Gly Gly
        115                 120                 125

Gly Gly Gly Leu Gly Gly Ala Gly Gly Phe Gly Ala Gly Gly
    130                 135                 140

Gly Ala Gly Gly Gly Leu Gly Gly Gly Gly Gly Gly Phe Gly Gly
145                 150                 155                 160
```

Gly Gly Gly Gly Ile Gly Gly Ala Gly Gly Phe Gly Ala
            165                 170                 175

Gly Gly Gly Val Gly Gly Gly Leu Gly Gly Gly Gly
        180                 185                 190

Gly Phe Gly Gly Gly Gly Ile Gly Gly Lys His
        195                 200                 205

<210> SEQ ID NO 31
<211> LENGTH: 399
<212> TYPE: PRT
<213> ORGANISM: Nicotiana sp.

<400> SEQUENCE: 31

Met Ala Thr Met Glu Ile Gly Asn Leu Gly Leu Arg Phe Arg Pro Gln
1               5                   10                  15

Ile Ala Ile Asn Pro Thr Arg Asn Asn Tyr Cys Lys Gln Phe Leu Gly
            20                  25                  30

Gln Lys Lys Gln Asn Lys Lys Arg Phe Leu Val Cys Ser Val Val Asp
        35                  40                  45

Gln Lys Glu Ala Lys Val Ser Ser Phe Ser Asn Glu Glu Asn Ala Leu
    50                  55                  60

Ile Glu Ala Leu Ile Gly Ile Gln Gly Arg Gly Arg Ser Ala Ser Pro
65                  70                  75                  80

Gln Gln Leu Gln Glu Val Glu Arg Ala Val Lys Val Leu Glu Gly Ser
                85                  90                  95

Asp Gly Val Ser Glu Pro Thr Ser Ser Ser Leu Ile Glu Gly Arg Trp
            100                 105                 110

Gln Leu Met Phe Thr Thr Arg Pro Gly Ser Ala Ser Pro Ile Gln Arg
        115                 120                 125

Thr Phe Val Gly Val Asp Ser Phe Ser Val Phe Gln Glu Val Phe Leu
    130                 135                 140

Arg Thr Asn Asp Pro Arg Val Ser Asn Ile Val Lys Phe Ser Glu Ala
145                 150                 155                 160

Ile Gly Glu Leu Lys Val Glu Ala Leu Ala Thr Ile Lys Asp Gly Lys
                165                 170                 175

Arg Ile Leu Phe Gln Phe Asp Arg Ala Ala Phe Ser Phe Lys Phe Leu
            180                 185                 190

Pro Val Lys Val Pro Tyr Pro Val Pro Phe Arg Leu Leu Gly Asp Glu
        195                 200                 205

Ala Lys Gly Trp Leu Asp Thr Thr Tyr Leu Ser Pro Ser Gly Asn Leu
    210                 215                 220

Arg Ile Ser Arg Gly Asn Lys Gly Thr Thr Phe Val Leu Gln Lys Glu
225                 230                 235                 240

Ala Glu Pro Arg Gln Lys Leu Leu Ser Ser Ile Ser Thr Gly Thr Ser
                245                 250                 255

Val Glu Lys Ala Ile Asp Glu Phe Ile Ser Leu Asn Gln Asn Val Ala
            260                 265                 270

Asn Pro Glu Leu Glu Leu Leu Glu Gly Glu Trp Gln Met Ile Trp Ser
        275                 280                 285

Ser Gln Val Glu Thr Asp Ser Trp Val Glu Asn Ala Gly Asn Gly Leu
    290                 295                 300

Met Gly Met Gln Ile Val Lys Pro Asn Gly Gln Leu Lys Phe Leu Val
305                 310                 315                 320

Glu Ile Phe Phe Gly Ile Arg Phe Ser Met Thr Gly Lys Tyr Glu Lys
                325                 330                 335

```
Ser Gly Ser Asn Thr Tyr Asn Val Ile Met Asp Asp Gly Ala Phe Val
            340                 345                 350

Ala Gly Val Tyr Gly Ile Pro Val Glu Met Glu Ser Lys Phe Thr Ile
            355                 360                 365

Glu Ile Leu Tyr Thr Asp Asp Lys Ile Arg Ile Ser Arg Gly Tyr Asn
            370                 375                 380

Lys Ile Leu Phe Ile His Val Arg Val Asp Gly Ser Lys Lys Lys
385                 390                 395

<210> SEQ ID NO 32
<211> LENGTH: 267
<212> TYPE: PRT
<213> ORGANISM: Nicotiana sp.

<400> SEQUENCE: 32

Met Val Ser Leu Ile Ser Thr Ala Ile Leu Pro His Ile Ser Ser Ser
1               5                   10                  15

Phe Met Gly Asn Ser Arg Asn Leu Lys Ser Ser Asn Ile Phe Pro
            20                  25                  30

Ser Ile Lys Leu Ser Asn Gln Lys Thr Thr Pro Arg Thr Arg Thr Pro
            35                  40                  45

Phe Leu Ile Phe Asn Lys Ala Ala Ser Phe Asp Val Ser Ala Ala Asp
50                  55                  60

Ser Ala Asn Ser Gly Ser Val Arg Phe Arg Leu Asn Asn Leu Gly Pro
65                  70                  75                  80

Gln Pro Gly Ala Thr Lys Asn Arg Lys Arg Lys Gly Arg Gly His Ala
            85                  90                  95

Ala Gly Gln Gly Gly Ser Cys Gly Phe Gly Met Arg Gly Gln Lys Ser
            100                 105                 110

Arg Ser Gly Pro Gly Val Arg Lys Gly Phe Glu Gly Gly Gln Met Pro
            115                 120                 125

Leu Tyr Arg Arg Leu Pro Lys Leu Arg Gly Ile Ala Gly Gly Met Ser
            130                 135                 140

Ala Gly Leu Pro Lys Tyr Val Pro Val Asn Leu Lys Asp Ile Glu Glu
145                 150                 155                 160

Ala Gly Phe Gln Glu Gly Glu Val Ser Leu Glu Ser Leu Lys Gln
            165                 170                 175

Lys Gly Leu Ile Asn Pro Ser Gly Arg Glu Arg Leu Pro Leu Lys
            180                 185                 190

Ile Leu Gly Asp Gly Glu Leu Ser Val Lys Leu Asn Phe Lys Ala Arg
            195                 200                 205

Ala Phe Ser Thr Ser Ala Lys Glu Lys Leu Glu Ala Ala Gly Cys Ser
210                 215                 220

Leu Thr Val Leu Pro Gly Arg Lys Lys Trp Val Lys Pro Ser Val Ala
225                 230                 235                 240

Lys Asn Leu Ala Arg Ala Glu Glu Tyr Phe Ala Lys Lys Arg Ala Ala
            245                 250                 255

Ala Ala Ser Glu Ala Ala Asp Pro Ser Ser Ala
            260                 265

<210> SEQ ID NO 33
<211> LENGTH: 60
<212> TYPE: PRT
<213> ORGANISM: Nicotiana sp.

<400> SEQUENCE: 33
```

```
Met Glu Ser Val Glu Phe Gly Met Pro Ile Thr Asn Gln Asn Ile Lys
1               5                   10                  15

Ala Val Ile Phe Asp Met Phe Met Ala Gly Ala Glu Thr Ser Ser Thr
                20                  25                  30

Thr Leu Ile Trp Val Met Ala Glu Leu Ile Arg Asn Pro Ser Val Met
            35                  40                  45

Ala Lys Ala Gln Arg Glu Val Arg Gly Ser Glu Ser
        50                  55                  60

<210> SEQ ID NO 34
<211> LENGTH: 156
<212> TYPE: PRT
<213> ORGANISM: Nicotiana sp.

<400> SEQUENCE: 34

Met Gly His Asp Cys His Gly Ile Glu Asn Lys Lys Ser Val Ala Val
1               5                   10                  15

Val Gly Leu Lys Ile Leu Ile Asn His Lys Leu Ser Gln Ala Lys Ala
                20                  25                  30

Asn Pro Asn Asn Val Ser Arg Phe Thr Arg Val Lys Pro Ile Phe His
                35                  40                  45

Thr Asn Tyr Thr Glu Ser Ser Ser Glu Gln Asn Ser Cys Phe Leu
    50                  55                  60

Lys Tyr Cys Cys Leu Cys Asn Lys Thr Leu Arg Leu Asp Lys Gln Val
65                  70                  75                  80

Tyr Met Tyr Lys Gly Asp Met Gly Phe Cys Ser Leu Glu Cys Arg His
                85                  90                  95

Arg Gln Ile Tyr Leu Asp Glu Ile Lys Glu Ile Glu Asn Cys Thr Lys
                100                 105                 110

Lys Met Leu Arg Ser Phe Arg Gln Cys Gly Asp Gly Arg Cys Ser
            115                 120                 125

Glu Thr Ser Thr Leu Leu Glu Glu Tyr His Gln Arg Arg Asn Pro Leu
        130                 135                 140

Ser Tyr Ser Lys Asn Arg Thr Ile Phe Thr Phe Ser
145                 150                 155
```